US 11,865,179 B2

(12) United States Patent
Cacace et al.

(10) Patent No.: US 11,865,179 B2
(45) Date of Patent: *Jan. 9, 2024

(54) PROGESTERONE FORMULATIONS HAVING A DESIRABLE PK PROFILE

(71) Applicant: TherapeuticsMD, Inc., Boca Raton, FL (US)

(72) Inventors: Janice Cacace, St. Petersburg, FL (US); Peter H. R. Persicaner, Boca Raton, FL (US); Thorsteinn Thorsteinsson, West Palm Beach, FL (US); Frederick Sancilio, Palm Beach Gardens, FL (US); Julia Amadio, Boca Raton, FL (US); Brian Bernick, Boca Raton, FL (US); Neda Irani, Palm Beach Gardens, FL (US)

(73) Assignee: TherapeuticsMD, Inc., Boca Raton, FL (US)

( * ) Notice: Subject to any disclaimer, the term of this patent is extended or adjusted under 35 U.S.C. 154(b) by 63 days.

This patent is subject to a terminal disclaimer.

(21) Appl. No.: 17/348,140

(22) Filed: Jun. 15, 2021

(65) Prior Publication Data
US 2022/0040307 A1 Feb. 10, 2022

Related U.S. Application Data

(63) Continuation of application No. 16/578,148, filed on Sep. 20, 2019, now Pat. No. 11,033,626, which is a
(Continued)

(51) Int. Cl.
*A61K 47/14* (2017.01)
*A61K 31/57* (2006.01)
*A61K 9/48* (2006.01)

(52) U.S. Cl.
CPC ............ *A61K 47/14* (2013.01); *A61K 9/4825* (2013.01); *A61K 9/4858* (2013.01); *A61K 31/57* (2013.01)

(58) Field of Classification Search
CPC . A61K 31/57; A61K 9/00; A61K 9/10; A61K 47/14
See application file for complete search history.

(56) References Cited

U.S. PATENT DOCUMENTS

| 1,967,351 A | 7/1934 | Doisy |
| 2,232,438 A | 2/1941 | Butenandt |

(Continued)

FOREIGN PATENT DOCUMENTS

| BR | PI1001367 A2 | 7/2012 |
| CN | 102258455 A | 11/2011 |

(Continued)

OTHER PUBLICATIONS

US 6,214,374 B1, 04/2001, Schmirler et al. (withdrawn)
(Continued)

*Primary Examiner* — Shengjun Wang
(74) *Attorney, Agent, or Firm* — Sterne Kessler Goldstein & Fox P.L.L.C.

(57) ABSTRACT

This disclosure provides progesterone formulations, methods of using these formulations, and their related pharmacokinetic parameters. In particular embodiments, the formulations disclosed herein allow for a reduction in the amount of progesterone administered to a patient in need thereof, while still providing the benefits of a larger dosage amount.

14 Claims, 10 Drawing Sheets

Related U.S. Application Data continuation of application No. 15/454,898, filed on Mar. 9, 2017, now Pat. No. 10,471,148, which is a continuation of application No. 14/671,655, filed on Mar. 27, 2015, now abandoned, which is a continuation-in-part of application No. 14/125,547, filed as application No. PCT/US2013/046442 on Jun. 18, 2013, now Pat. No. 10,052,386, said application No. 14/671,655 is a continuation-in-part of application No. 13/843,428, filed on Mar. 15, 2013, now Pat. No. 9,301,920, said application No. PCT/US2013/046442 is a continuation of application No. 13/843,362, filed on Mar. 15, 2013, now abandoned, and a continuation of application No. PCT/US2013/023309, filed on Jan. 25, 2013, and a continuation of application No. 13/684,002, filed on Nov. 21, 2012, now Pat. No. 8,633,178.

(60) Provisional application No. 61/972,068, filed on Mar. 28, 2014, provisional application No. 61/662,265, filed on Jun. 20, 2012, provisional application No. 61/661,302, filed on Jun. 18, 2012.

(56) References Cited

U.S. PATENT DOCUMENTS

| | | |
|---|---|---|
| 2,379,832 A | 7/1945 | Serini et al. |
| 2,649,399 A | 8/1953 | Beall et al. |
| 3,198,707 A | 8/1965 | Nomine et al. |
| 3,478,070 A | 11/1969 | Reinhardt et al. |
| 3,526,648 A | 9/1970 | Daniel et al. |
| 3,710,795 A | 1/1973 | Higuchi et al. |
| 3,729,560 A | 4/1973 | Hagerman |
| 3,729,566 A | 4/1973 | Youngdale et al. |
| 3,755,573 A | 8/1973 | Berman |
| 3,755,575 A | 8/1973 | Lerner |
| 3,903,880 A | 9/1975 | Higuchi et al. |
| 3,916,898 A | 11/1975 | Robinson |
| 3,916,899 A | 11/1975 | Theeuwes et al. |
| 3,921,636 A | 11/1975 | Zaffaroni |
| 3,923,997 A | 12/1975 | Meuly |
| 3,948,254 A | 4/1976 | Zaffaroni |
| 3,971,367 A | 7/1976 | Zaffaroni |
| 3,977,404 A | 8/1976 | Theeuwes |
| 3,993,072 A | 11/1976 | Zaffaroni |
| 4,008,719 A | 2/1977 | Theeuwes et al. |
| 4,012,496 A | 3/1977 | Schopflin et al. |
| 4,014,334 A | 3/1977 | Theeuwes et al. |
| 4,014,987 A | 3/1977 | Heller et al. |
| 4,016,251 A | 4/1977 | Higuchi et al. |
| 4,071,623 A | 1/1978 | Van Der Vies |
| 4,093,709 A | 6/1978 | Choi et al. |
| 4,154,820 A | 5/1979 | Simoons |
| 4,155,991 A | 5/1979 | Hartmann et al. |
| 4,196,188 A | 4/1980 | Besins |
| 4,215,691 A | 8/1980 | Wong |
| 4,237,885 A | 12/1980 | Pharriss et al. |
| 4,310,510 A | 1/1982 | Sherman et al. |
| 4,327,725 A | 5/1982 | Cortese et al. |
| 4,372,951 A | 2/1983 | Vorys |
| 4,384,096 A | 5/1983 | Sonnabend |
| 4,393,871 A | 7/1983 | Vorhauer et al. |
| 4,402,695 A | 9/1983 | Wong |
| 4,423,151 A | 12/1983 | Baranczuk |
| 4,449,980 A | 5/1984 | Millar et al. |
| 4,610,687 A | 9/1986 | Fogwell |
| 4,629,449 A | 12/1986 | Wong |
| 4,732,763 A | 3/1988 | Beck et al. |
| 4,738,957 A | 4/1988 | Laurent et al. |
| 4,756,907 A | 7/1988 | Beck et al. |
| 4,762,717 A | 8/1988 | Crowley, Jr. |
| 4,788,062 A | 11/1988 | Gale et al. |
| 4,816,257 A | 3/1989 | Buster et al. |
| 4,822,616 A | 4/1989 | Zimmermann et al. |
| 4,865,848 A | 9/1989 | Cheng et al. |
| 4,900,734 A | 2/1990 | Maxson et al. |
| 4,906,475 A | 3/1990 | Kim |
| 4,942,158 A | 7/1990 | Sarpotdar et al. |
| 4,961,931 A | 10/1990 | Wong |
| 5,030,629 A | 7/1991 | Rajadhyaksha |
| 5,064,654 A | 11/1991 | Berner et al. |
| 5,108,995 A | 4/1992 | Casper |
| 5,128,138 A | 7/1992 | Blank |
| 5,130,137 A | 7/1992 | Crowley, Jr. |
| 5,140,021 A | 8/1992 | Maxson et al. |
| 5,211,952 A | 5/1993 | Spicer et al. |
| 5,252,334 A | 10/1993 | Chiang et al. |
| 5,280,023 A | 1/1994 | Ehrlich et al. |
| 5,288,496 A | 2/1994 | Lewis |
| 5,340,584 A | 8/1994 | Spicer et al. |
| 5,340,585 A | 8/1994 | Pike et al. |
| 5,340,586 A | 8/1994 | Pike et al. |
| 5,362,497 A | 11/1994 | Yamada et al. |
| 5,382,573 A | 1/1995 | Casper |
| 5,393,528 A | 2/1995 | Staab |
| 5,393,529 A | 2/1995 | Hoffmann et al. |
| 5,419,910 A | 5/1995 | Lewis |
| 5,468,736 A | 11/1995 | Hodgen |
| 5,474,783 A | 12/1995 | Miranda et al. |
| 5,480,776 A | 1/1996 | Dullien |
| 5,514,673 A | 5/1996 | Heckenmueller et al. |
| 5,516,528 A | 5/1996 | Hughes et al. |
| 5,527,534 A | 6/1996 | Myhling |
| 5,529,782 A | 6/1996 | Staab |
| 5,538,736 A | 7/1996 | Hoffmann et al. |
| 5,543,150 A | 8/1996 | Bologna et al. |
| 5,547,948 A | 8/1996 | Barcomb |
| 5,556,635 A | 9/1996 | Istin et al. |
| 5,565,199 A | 10/1996 | Page et al. |
| 5,567,831 A | 10/1996 | Li |
| 5,569,652 A | 10/1996 | Beier et al. |
| 5,580,572 A | 12/1996 | Mikler et al. |
| 5,582,592 A | 12/1996 | Kendrick |
| 5,585,370 A | 12/1996 | Casper |
| 5,595,759 A | 1/1997 | Wright et al. |
| 5,595,970 A | 1/1997 | Garfield et al. |
| 5,605,702 A | 2/1997 | Teillaud et al. |
| 5,607,691 A | 3/1997 | Hale et al. |
| 5,607,693 A | 3/1997 | Bonte et al. |
| 5,609,617 A | 3/1997 | Shealy et al. |
| 5,620,705 A | 4/1997 | Dong et al. |
| 5,626,866 A | 5/1997 | Ebert et al. |
| 5,629,021 A | 5/1997 | Wright |
| 5,633,011 A | 5/1997 | Dong et al. |
| 5,633,242 A | 5/1997 | Oettel et al. |
| 5,639,743 A | 6/1997 | Kaswan et al. |
| 5,653,983 A | 8/1997 | Meybeck et al. |
| 5,656,286 A | 8/1997 | Miranda et al. |
| 5,660,839 A | 8/1997 | Allec et al. |
| 5,662,927 A | 9/1997 | Ehrlich et al. |
| 5,663,160 A | 9/1997 | Meybeck et al. |
| 5,676,968 A | 10/1997 | Lipp et al. |
| 5,677,292 A | 10/1997 | Li et al. |
| 5,686,097 A | 11/1997 | Taskovich et al. |
| 5,693,335 A | 12/1997 | Xia et al. |
| 5,694,947 A | 12/1997 | Lehtinen et al. |
| 5,700,480 A | 12/1997 | Hille et al. |
| 5,709,844 A | 1/1998 | Arbeit et al. |
| 5,719,197 A | 2/1998 | Kanios et al. |
| 5,735,801 A | 4/1998 | Caillouette |
| 5,739,176 A | 4/1998 | Dunn et al. |
| 5,744,463 A | 4/1998 | Bair |
| 5,747,058 A | 5/1998 | Tipton et al. |
| 5,762,614 A | 6/1998 | Caillouette |
| 5,770,176 A | 6/1998 | Nargessi |
| 5,770,219 A | 6/1998 | Chiang et al. |
| 5,770,220 A | 6/1998 | Meconi et al. |
| 5,770,227 A | 6/1998 | Dong et al. |
| 5,776,495 A | 7/1998 | Duclos et al. |
| 5,780,044 A | 7/1998 | Yewey et al. |
| 5,780,050 A | 7/1998 | Jain et al. |
| 5,788,980 A | 8/1998 | Nabahi |

(56) References Cited

U.S. PATENT DOCUMENTS

| | | |
|---|---|---|
| 5,788,984 A | 8/1998 | Guenther et al. |
| 5,789,442 A | 8/1998 | Garfield et al. |
| 5,811,416 A | 9/1998 | Chwalisz et al. |
| 5,811,547 A | 9/1998 | Nakamichi et al. |
| 5,814,329 A | 9/1998 | Shah |
| 5,820,878 A | 10/1998 | Hirano et al. |
| 5,827,200 A | 10/1998 | Caillouette |
| 5,840,327 A | 11/1998 | Gale et al. |
| 5,843,468 A | 12/1998 | Burkoth et al. |
| 5,843,979 A | 12/1998 | Wille et al. |
| 5,858,394 A | 1/1999 | Lipp et al. |
| 5,863,552 A | 1/1999 | Yue |
| 5,866,603 A | 2/1999 | Li et al. |
| 5,882,676 A | 3/1999 | Lee et al. |
| 5,885,612 A | 3/1999 | Meconi et al. |
| 5,888,533 A | 3/1999 | Dunn |
| 5,891,462 A | 4/1999 | Carrara |
| 5,891,868 A | 4/1999 | Cummings et al. |
| 5,898,038 A | 4/1999 | Yallampalli et al. |
| 5,902,603 A | 5/1999 | Chen et al. |
| 5,904,931 A | 5/1999 | Lipp et al. |
| 5,906,830 A | 5/1999 | Farinas et al. |
| 5,912,010 A | 6/1999 | Wille et al. |
| 5,916,176 A | 6/1999 | Caillouette |
| RE36,247 E | 7/1999 | Plunkett et al. |
| 5,919,477 A | 7/1999 | Bevan et al. |
| 5,922,349 A | 7/1999 | Elliesen et al. |
| 5,928,666 A | 7/1999 | Farinas et al. |
| 5,942,243 A | 8/1999 | Shah |
| 5,952,000 A | 9/1999 | Venkateshwaran et al. |
| 5,958,446 A | 9/1999 | Miranda et al. |
| 5,962,445 A | 10/1999 | Stewart |
| 5,968,919 A | 10/1999 | Samour et al. |
| 5,972,372 A | 10/1999 | Saleh et al. |
| 5,985,311 A | 11/1999 | Cordes et al. |
| 5,985,850 A | 11/1999 | Falk et al. |
| 5,985,861 A | 11/1999 | Levine et al. |
| 5,989,568 A | 11/1999 | Breton et al. |
| 5,993,856 A | 11/1999 | Ragavan et al. |
| 6,001,846 A | 12/1999 | Edwards et al. |
| 6,007,835 A | 12/1999 | Bon-Lapillonne et al. |
| 6,010,715 A | 1/2000 | Wick et al. |
| 6,013,276 A | 1/2000 | Math et al. |
| 6,022,562 A | 2/2000 | Autant et al. |
| 6,024,974 A | 2/2000 | Li |
| 6,024,976 A | 2/2000 | Miranda et al. |
| 6,028,057 A | 2/2000 | Burns |
| 6,030,948 A | 2/2000 | Mann |
| 6,039,968 A | 3/2000 | Nabahi |
| 6,040,340 A | 3/2000 | Chwalisz et al. |
| 6,056,972 A | 5/2000 | Hermsmeyer |
| 6,060,077 A | 5/2000 | Meignant |
| 6,068,853 A | 5/2000 | Giannos et al. |
| 6,074,625 A | 6/2000 | Hawthorne et al. |
| 6,077,531 A | 6/2000 | Salin-Drouin |
| 6,080,118 A | 6/2000 | Blythe |
| 6,083,178 A | 7/2000 | Caillouette |
| 6,086,916 A | 7/2000 | Agnus et al. |
| 6,087,352 A | 7/2000 | Trout |
| 6,090,404 A | 7/2000 | Meconi et al. |
| 6,096,338 A | 8/2000 | Lacy et al. |
| 6,106,848 A | 8/2000 | Preuilh et al. |
| 6,117,446 A | 9/2000 | Place |
| 6,117,450 A | 9/2000 | Dittgen et al. |
| 6,124,362 A | 9/2000 | Bradbury et al. |
| 6,133,251 A | 10/2000 | Dittgen et al. |
| 6,133,320 A | 10/2000 | Yallampalli et al. |
| 6,139,868 A | 10/2000 | Hoffmann |
| 6,139,873 A | 10/2000 | Hughes, Jr. et al. |
| 6,149,935 A | 11/2000 | Chiang et al. |
| 6,153,216 A | 11/2000 | Cordes et al. |
| 6,165,491 A | 12/2000 | Grasset et al. |
| 6,165,975 A | 12/2000 | Adams et al. |
| 6,187,323 B1 | 2/2001 | Aiache et al. |
| 6,187,339 B1 | 2/2001 | De Haan et al. |
| 6,190,331 B1 | 2/2001 | Caillouette |
| 6,201,072 B1 | 3/2001 | Rathi et al. |
| 6,217,886 B1 | 4/2001 | Önyüksel et al. |
| 6,225,297 B1 | 5/2001 | Stockemann et al. |
| 6,227,202 B1 | 5/2001 | Matapurkar |
| 6,228,383 B1 | 5/2001 | Hansen et al. |
| 6,228,852 B1 | 5/2001 | Shaak |
| 6,242,509 B1 | 6/2001 | Berger et al. |
| 6,245,811 B1 | 6/2001 | Horrobin et al. |
| 6,262,115 B1 | 7/2001 | Guittard et al. |
| 6,264,980 B1 | 7/2001 | Hille |
| 6,267,984 B1 | 7/2001 | Beste et al. |
| 6,274,165 B1 | 8/2001 | Meconi et al. |
| 6,277,418 B1 | 8/2001 | Markaverich et al. |
| 6,283,927 B1 | 9/2001 | Caillouette |
| 6,287,588 B1 | 9/2001 | Shih et al. |
| 6,287,693 B1 | 9/2001 | Savoir et al. |
| 6,294,188 B1 | 9/2001 | Ragavan et al. |
| 6,294,192 B1 | 9/2001 | Patel et al. |
| 6,294,550 B1 | 9/2001 | Place et al. |
| 6,299,900 B1 | 10/2001 | Reed et al. |
| 6,303,132 B1 | 10/2001 | Nelson |
| 6,303,588 B1 | 10/2001 | Danielov |
| 6,306,841 B1 | 10/2001 | Place et al. |
| 6,306,914 B1 | 10/2001 | De Ziegler et al. |
| 6,309,669 B1 | 10/2001 | Setterstrom et al. |
| 6,309,848 B1 | 10/2001 | Howett et al. |
| 6,312,703 B1 | 11/2001 | Orthoefer |
| 6,328,987 B1 | 12/2001 | Marini |
| 6,342,491 B1 | 1/2002 | Dey et al. |
| 6,344,211 B1 | 2/2002 | Hille |
| 6,372,209 B1 | 4/2002 | Chrisope |
| 6,372,245 B1 | 4/2002 | Bowman et al. |
| 6,372,246 B1 | 4/2002 | Wei et al. |
| 6,387,390 B1 | 5/2002 | Deaver et al. |
| 6,402,705 B1 | 6/2002 | Caillouette |
| 6,416,778 B1 | 7/2002 | Ragavan et al. |
| 6,420,352 B1 | 7/2002 | Knowles |
| 6,423,039 B1 | 7/2002 | Rathbone et al. |
| 6,423,683 B1 | 7/2002 | Heaton et al. |
| 6,432,438 B1 | 8/2002 | Shukla |
| 6,436,633 B1 | 8/2002 | Kreider et al. |
| 6,440,454 B1 | 8/2002 | Santoro et al. |
| 6,444,224 B1 | 9/2002 | Rathbone et al. |
| 6,444,234 B1 | 9/2002 | Kirby et al. |
| 6,451,300 B1 | 9/2002 | Dunlop et al. |
| 6,451,339 B2 | 9/2002 | Patel et al. |
| 6,451,779 B1 | 9/2002 | Hesch |
| 6,455,246 B1 | 9/2002 | Howett et al. |
| 6,455,517 B1 | 9/2002 | Tanabe et al. |
| 6,465,004 B1 | 10/2002 | Rossi-Montero et al. |
| 6,465,005 B1 | 10/2002 | Biali et al. |
| 6,465,006 B1 | 10/2002 | Zhang et al. |
| 6,468,526 B2 | 10/2002 | Chrisope |
| 6,469,016 B1 | 10/2002 | Place et al. |
| 6,472,434 B1 | 10/2002 | Place et al. |
| 6,479,232 B1 | 11/2002 | Howett et al. |
| 6,495,160 B2 | 12/2002 | Esposito et al. |
| 6,500,814 B1 | 12/2002 | Hesch |
| 6,503,896 B1 | 1/2003 | Tanabe et al. |
| 6,511,969 B1 | 1/2003 | Hermsmeyer |
| 6,521,250 B2 | 2/2003 | Meconi et al. |
| 6,526,980 B1 | 3/2003 | Tracy et al. |
| 6,528,094 B1 | 3/2003 | Savoir et al. |
| 6,531,149 B1 | 3/2003 | Kirstgen et al. |
| 6,537,580 B1 | 3/2003 | Savoir et al. |
| 6,538,039 B2 | 3/2003 | Laurent |
| 6,544,196 B2 | 4/2003 | Caillouette |
| 6,544,553 B1 | 4/2003 | Hsia et al. |
| 6,548,053 B1 | 4/2003 | Stewart et al. |
| 6,548,491 B2 | 4/2003 | Tanabe et al. |
| 6,551,611 B2 | 4/2003 | Elliesen et al. |
| 6,555,131 B1 | 4/2003 | Wolff et al. |
| 6,562,367 B1 | 5/2003 | Wolff et al. |
| 6,562,370 B2 | 5/2003 | Luo et al. |
| 6,562,790 B2 | 5/2003 | Chein et al. |
| 6,569,463 B2 | 5/2003 | Patel et al. |
| 6,583,129 B1 | 6/2003 | Mazer et al. |
| 6,586,006 B2 | 7/2003 | Roser et al. |

(56) References Cited

U.S. PATENT DOCUMENTS

| | | | |
|---|---|---|---|
| 6,589,549 | B2 | 7/2003 | Shih et al. |
| 6,593,317 | B1 | 7/2003 | De Ziegler et al. |
| 6,599,519 | B1 | 7/2003 | Seo et al. |
| 6,610,652 | B2 | 8/2003 | Heaton et al. |
| 6,610,670 | B2 | 8/2003 | Backensfeld et al. |
| 6,610,674 | B1 | 8/2003 | Schreiber |
| 6,635,274 | B1 | 10/2003 | Masiz et al. |
| 6,638,528 | B1 | 10/2003 | Kanios |
| 6,638,536 | B2 | 10/2003 | Savoir et al. |
| 6,645,528 | B1 | 11/2003 | Straub et al. |
| 6,649,155 | B1 | 11/2003 | Dunlop et al. |
| 6,653,298 | B2 | 11/2003 | Potter et al. |
| 6,656,929 | B1 | 12/2003 | Agnus et al. |
| 6,660,726 | B2 | 12/2003 | Hill et al. |
| 6,663,608 | B2 | 12/2003 | Rathbone et al. |
| 6,663,895 | B2 | 12/2003 | Savoir et al. |
| 6,682,757 | B1 | 1/2004 | Wright |
| 6,692,763 | B1 | 2/2004 | Cummings et al. |
| 6,708,822 | B1 | 3/2004 | Muni |
| 6,720,001 | B2 | 4/2004 | Chen et al. |
| 6,737,081 | B2 | 5/2004 | Savoir et al. |
| 6,740,333 | B2 | 5/2004 | Beckett et al. |
| 6,743,448 | B2 | 6/2004 | Kryger |
| 6,743,815 | B2 | 6/2004 | Huebner et al. |
| 6,747,018 | B2 | 6/2004 | Tanabe et al. |
| 6,750,291 | B2 | 6/2004 | Kim et al. |
| 6,756,208 | B2 | 6/2004 | Griffin et al. |
| 6,776,164 | B2 | 8/2004 | Bunt et al. |
| 6,787,152 | B2 | 9/2004 | Kirby et al. |
| 6,805,877 | B2 | 10/2004 | Massara et al. |
| 6,809,085 | B1 | 10/2004 | Elson et al. |
| 6,818,226 | B2 | 11/2004 | Reed et al. |
| 6,821,524 | B2 | 11/2004 | Marini |
| 6,841,716 | B1 | 1/2005 | Tsutsumi |
| 6,844,334 | B2 | 1/2005 | Hill et al. |
| 6,855,703 | B1 | 2/2005 | Hill et al. |
| 6,860,859 | B2 | 3/2005 | Mehrotra et al. |
| 6,866,865 | B2 | 3/2005 | Hsia et al. |
| 6,869,969 | B2 | 3/2005 | Huebner et al. |
| 6,878,518 | B2 | 4/2005 | Whitehead |
| 6,901,278 | B1 | 5/2005 | Notelovitz |
| 6,905,705 | B2 | 6/2005 | Palm et al. |
| 6,911,211 | B2 | 6/2005 | Eini et al. |
| 6,911,438 | B2 | 6/2005 | Wright |
| 6,923,988 | B2 | 8/2005 | Patel et al. |
| 6,924,274 | B2 | 8/2005 | Lardy et al. |
| 6,932,983 | B1 | 8/2005 | Straub et al. |
| 6,939,558 | B2 | 9/2005 | Massara et al. |
| 6,943,021 | B2 | 9/2005 | Klausner et al. |
| 6,958,327 | B1 | 10/2005 | Hillisch et al. |
| 6,960,337 | B2 | 11/2005 | Daniels et al. |
| 6,962,691 | B1 | 11/2005 | Lulla et al. |
| 6,962,908 | B2 | 11/2005 | Aloba et al. |
| 6,967,194 | B1 | 11/2005 | Matsuo et al. |
| 6,974,569 | B2 | 12/2005 | Dunlop et al. |
| 6,977,250 | B2 | 12/2005 | Rodriguez |
| 6,978,945 | B2 | 12/2005 | Wong et al. |
| 6,995,149 | B1 | 2/2006 | Endrikat et al. |
| 7,004,321 | B1 | 2/2006 | Palm et al. |
| 7,005,429 | B2 | 2/2006 | Dey et al. |
| 7,011,846 | B2 | 3/2006 | Shojaei et al. |
| 7,018,992 | B2 | 3/2006 | Koch et al. |
| 7,030,104 | B2 | 4/2006 | Gray et al. |
| 7,030,157 | B2 | 4/2006 | Huazhu et al. |
| RE39,104 | E | 5/2006 | Duclos et al. |
| 7,074,779 | B2 | 7/2006 | Sui et al. |
| 7,083,590 | B1 | 8/2006 | Bunt et al. |
| 7,091,213 | B2 | 8/2006 | Metcalf et al. |
| 7,094,228 | B2 | 8/2006 | Zhang et al. |
| 7,097,853 | B1 | 8/2006 | Garbe et al. |
| 7,101,342 | B1 | 9/2006 | Caillouette |
| 7,105,573 | B2 | 9/2006 | Krajcik et al. |
| 7,135,190 | B2 | 11/2006 | Piao et al. |
| 7,153,522 | B1 | 12/2006 | Ikeura et al. |
| 7,163,681 | B2 | 1/2007 | Giles-Komar et al. |
| 7,163,699 | B2 | 1/2007 | Besse |
| 7,175,850 | B2 | 2/2007 | Cevc |
| 7,179,799 | B2 | 2/2007 | Hill et al. |
| 7,196,074 | B2 | 3/2007 | Blye et al. |
| 7,198,800 | B1 | 4/2007 | Ko |
| 7,198,801 | B2 | 4/2007 | Carrara et al. |
| 7,226,910 | B2 | 6/2007 | Wilson et al. |
| 7,247,625 | B2 | 7/2007 | Zhang et al. |
| 7,250,446 | B2 | 7/2007 | Sangita et al. |
| 7,267,829 | B2 | 9/2007 | Kirby et al. |
| 7,300,926 | B2 | 11/2007 | Prokai et al. |
| 7,303,763 | B2 | 12/2007 | Ho |
| 7,317,037 | B2 | 1/2008 | Fensome et al. |
| 7,329,654 | B2 | 2/2008 | Kanojia et al. |
| 7,335,650 | B2 | 2/2008 | Potter et al. |
| 7,374,779 | B2 | 5/2008 | Chen et al. |
| 7,378,404 | B2 | 5/2008 | Peters et al. |
| 7,381,427 | B2 | 6/2008 | Ancira et al. |
| 7,387,789 | B2 | 6/2008 | Klose et al. |
| 7,388,006 | B2 | 6/2008 | Schmees et al. |
| 7,414,043 | B2 | 8/2008 | Kosemund et al. |
| 7,427,413 | B2 | 9/2008 | Savoir et al. |
| 7,427,609 | B2 | 9/2008 | Leonard |
| 7,429,576 | B2 | 9/2008 | Labrie |
| 7,431,941 | B2 | 10/2008 | Besins et al. |
| 7,456,159 | B2 | 11/2008 | Houze et al. |
| 7,459,445 | B2 | 12/2008 | Hill et al. |
| 7,465,587 | B2 | 12/2008 | Imrich et al. |
| 7,470,433 | B2 | 12/2008 | Carrara et al. |
| 7,485,666 | B2 | 2/2009 | Villanueva et al. |
| 7,497,855 | B2 | 3/2009 | Ausiello et al. |
| 7,498,303 | B2 | 3/2009 | Arnold et al. |
| 7,534,765 | B2 | 5/2009 | Gregg et al. |
| 7,534,780 | B2 | 5/2009 | Wyrwa et al. |
| 7,550,142 | B2 | 6/2009 | Giles-Komar et al. |
| 7,563,565 | B1 | 7/2009 | Matsuo et al. |
| 7,569,274 | B2 | 8/2009 | Besse et al. |
| 7,572,779 | B2 | 8/2009 | Aloba et al. |
| 7,572,780 | B2 | 8/2009 | Hermsmeyer |
| 7,589,082 | B2 | 9/2009 | Savoir et al. |
| 7,671,027 | B2 | 3/2010 | Loumaye |
| 7,674,783 | B2 | 3/2010 | Hermsmeyer |
| 7,687,281 | B2 | 3/2010 | Roth et al. |
| 7,687,485 | B2 | 3/2010 | Levinson et al. |
| 7,694,683 | B2 | 4/2010 | Callister et al. |
| 7,704,983 | B1 | 4/2010 | Hodgen et al. |
| 7,727,720 | B2 | 6/2010 | Dhallan |
| 7,732,408 | B2 | 6/2010 | Josephson et al. |
| 7,749,989 | B2 | 7/2010 | Hill et al. |
| 7,767,656 | B2 | 8/2010 | Shoichet et al. |
| 7,799,769 | B2 | 9/2010 | White et al. |
| 7,815,936 | B2 | 10/2010 | Hasenzahl et al. |
| 7,815,949 | B2 | 10/2010 | Cohen |
| 7,829,115 | B2 | 11/2010 | Besins et al. |
| 7,829,116 | B2 | 11/2010 | Griswold et al. |
| RE42,012 | E | 12/2010 | Deaver et al. |
| 7,850,992 | B2 | 12/2010 | Kim et al. |
| 7,854,753 | B2 | 12/2010 | Kraft et al. |
| 7,858,607 | B2 | 12/2010 | Mamchur |
| RE42,072 | E | 1/2011 | Deaver et al. |
| 7,862,552 | B2 | 1/2011 | McIntyre et al. |
| 7,867,990 | B2 | 1/2011 | Schultz et al. |
| 7,871,643 | B2 | 1/2011 | Lizio et al. |
| 7,879,830 | B2 | 2/2011 | Wiley |
| 7,884,093 | B2 | 2/2011 | Creasy et al. |
| 7,925,519 | B2 | 4/2011 | Greene |
| 7,939,104 | B2 | 5/2011 | Barbera et al. |
| 7,943,602 | B2 | 5/2011 | Bunschoten et al. |
| 7,943,604 | B2 | 5/2011 | Coelingh et al. |
| 7,945,459 | B2 | 5/2011 | Grace et al. |
| 7,960,368 | B2 | 6/2011 | Nickisch et al. |
| 7,989,436 | B2 | 8/2011 | Hill et al. |
| 7,989,487 | B2 | 8/2011 | Welsh et al. |
| 8,022,053 | B2 | 9/2011 | Mueller et al. |
| 8,048,017 | B2 | 11/2011 | Xu |
| 8,048,869 | B2 | 11/2011 | Bunschoten et al. |
| 8,063,030 | B2 | 11/2011 | Ellman |
| 8,071,576 | B2 | 12/2011 | Coelingh et al. |
| 8,071,729 | B2 | 12/2011 | Giles-Komar et al. |

(56) References Cited

U.S. PATENT DOCUMENTS

| | | |
|---|---|---|
| 8,075,916 B2 | 12/2011 | Song et al. |
| 8,075,917 B2 | 12/2011 | Chung et al. |
| 8,076,317 B2 | 12/2011 | Kulmann |
| 8,076,319 B2 | 12/2011 | Leonard |
| 8,080,553 B2 | 12/2011 | Keith et al. |
| 8,088,605 B2 | 1/2012 | Beaudet et al. |
| 8,096,940 B2 | 1/2012 | Josephson et al. |
| 8,101,209 B2 | 1/2012 | Legrand et al. |
| 8,101,773 B2 | 1/2012 | Smith et al. |
| 8,114,152 B2 | 2/2012 | Furst |
| 8,114,434 B2 | 2/2012 | Sasaki et al. |
| 8,114,442 B2 | 2/2012 | Tucker et al. |
| 8,119,741 B2 | 2/2012 | Pavlin |
| 8,121,886 B2 | 2/2012 | Azar |
| 8,124,118 B2 | 2/2012 | Lennernas et al. |
| 8,124,595 B2 | 2/2012 | Boissonneault |
| 8,147,561 B2 | 4/2012 | Binmoeller |
| 8,148,546 B2 | 4/2012 | Schuster et al. |
| 8,158,613 B2 | 4/2012 | Staniforth et al. |
| 8,158,614 B2 | 4/2012 | Lambert et al. |
| 8,163,722 B2 | 4/2012 | Savoir et al. |
| 8,177,449 B2 | 5/2012 | Bayly et al. |
| 8,182,833 B2 | 5/2012 | Hermsmeyer |
| 8,187,615 B2 | 5/2012 | Friedman |
| 8,195,403 B2 | 6/2012 | Ishikawa et al. |
| 8,202,736 B2 | 6/2012 | Mousa et al. |
| 8,217,024 B2 | 7/2012 | Ahmed et al. |
| 8,221,785 B2 | 7/2012 | Chien |
| 8,222,008 B2 | 7/2012 | Theone et al. |
| 8,222,237 B2 | 7/2012 | Nickisch et al. |
| 8,227,454 B2 | 7/2012 | Hill et al. |
| 8,227,509 B2 | 7/2012 | Castro et al. |
| 8,241,664 B2 | 8/2012 | Dudley et al. |
| 8,247,393 B2 | 8/2012 | Ahmed et al. |
| 8,257,724 B2 | 9/2012 | Cromack et al. |
| 8,257,725 B2 | 9/2012 | Cromack et al. |
| 8,268,352 B2 | 9/2012 | Vaya et al. |
| 8,268,806 B2 | 9/2012 | Labrie |
| 8,268,878 B2 | 9/2012 | Armer et al. |
| 8,273,730 B2 | 9/2012 | Fernandez et al. |
| 8,287,888 B2 | 10/2012 | Song et al. |
| 8,288,366 B2 | 10/2012 | Chochinov et al. |
| 8,318,898 B2 | 11/2012 | Fasel et al. |
| 8,324,193 B2 | 12/2012 | Lee-Sepsick et al. |
| 8,329,680 B2 | 12/2012 | Evans et al. |
| 8,337,814 B2 | 12/2012 | Osbakken et al. |
| 8,344,007 B2 | 1/2013 | Tang et al. |
| 8,349,820 B2 | 1/2013 | Zeun et al. |
| 8,353,863 B2 | 1/2013 | Imran |
| 8,357,723 B2 | 1/2013 | Satyam |
| 8,361,995 B2 | 1/2013 | Schramm |
| 8,362,091 B2 | 1/2013 | Tamarkin et al. |
| 8,372,424 B2 | 2/2013 | Berry et al. |
| 8,372,806 B2 | 2/2013 | Bohler et al. |
| 8,377,482 B2 | 2/2013 | Laurie et al. |
| 8,377,994 B2 | 2/2013 | Gray et al. |
| 8,394,759 B2 | 3/2013 | Barathur et al. |
| 8,415,332 B2 | 4/2013 | Diliberti et al. |
| 8,420,111 B2 | 4/2013 | Hermsmeyer |
| 8,435,561 B2 | 5/2013 | Besins et al. |
| 8,435,972 B2 | 5/2013 | Stein et al. |
| 8,449,879 B2 | 5/2013 | Laurent-Applegate et al. |
| 8,450,108 B2 | 5/2013 | Boyce |
| 8,454,945 B2 | 6/2013 | McCook et al. |
| 8,455,468 B2 | 6/2013 | Hoffman et al. |
| 8,461,138 B2 | 6/2013 | Boissonneault |
| 8,476,252 B2 | 7/2013 | Achleitner et al. |
| 8,481,488 B2 | 7/2013 | Carter |
| 8,486,374 B2 | 7/2013 | Tamarkin et al. |
| 8,486,442 B2 | 7/2013 | Matsushita et al. |
| 8,492,368 B2 | 7/2013 | Vanlandingham et al. |
| 8,507,467 B2 | 8/2013 | Matsui et al. |
| 8,512,693 B2 | 8/2013 | Capito et al. |
| 8,512,754 B2 | 8/2013 | Needham |
| 8,518,376 B2 | 8/2013 | Tamarkin et al. |
| 8,536,159 B2 | 9/2013 | Li et al. |
| 8,540,967 B2 | 9/2013 | Barrett et al. |
| 8,541,400 B2 | 9/2013 | Johnsson et al. |
| 8,551,462 B2 | 10/2013 | Goldstein et al. |
| 8,557,281 B2 | 10/2013 | Halliday et al. |
| 8,568,374 B2 | 10/2013 | De Graaff et al. |
| 8,591,951 B2 | 11/2013 | Kohn et al. |
| 8,613,951 B2 | 12/2013 | Zale et al. |
| 8,633,178 B2 * | 1/2014 | Bernick ................. A61K 31/57 424/452 |
| 8,633,180 B2 | 1/2014 | Li et al. |
| 8,636,787 B2 | 1/2014 | Sabaria |
| 8,636,982 B2 | 1/2014 | Tamarkin et al. |
| 8,653,129 B2 | 2/2014 | Fein et al. |
| 8,658,627 B2 | 2/2014 | Voskuhl |
| 8,658,628 B2 | 2/2014 | Baucom |
| 8,663,681 B2 | 3/2014 | Ahmed et al. |
| 8,663,692 B1 | 3/2014 | Mueller et al. |
| 8,663,703 B2 | 3/2014 | Lerner et al. |
| 8,664,207 B2 | 3/2014 | Li et al. |
| 8,669,293 B2 | 3/2014 | Levy et al. |
| 8,679,552 B2 | 3/2014 | Guthery |
| 8,694,358 B2 | 4/2014 | Tryfon |
| 8,697,127 B2 | 4/2014 | Sah |
| 8,697,710 B2 | 4/2014 | Li et al. |
| 8,703,105 B2 | 4/2014 | Tamarkin et al. |
| 8,709,385 B2 | 4/2014 | Tamarkin et al. |
| 8,709,451 B2 | 4/2014 | Rapoport et al. |
| 8,715,735 B2 | 5/2014 | Funke et al. |
| 8,721,331 B2 | 5/2014 | Raghuprasad |
| 8,722,021 B2 | 5/2014 | Friedman et al. |
| 8,734,846 B2 | 5/2014 | Ali et al. |
| 8,735,381 B2 | 5/2014 | Podolski |
| 8,741,336 B2 | 6/2014 | Dipierro et al. |
| 8,741,373 B2 | 6/2014 | Bromley et al. |
| 8,753,661 B2 | 6/2014 | Steinmuller-Nethl et al. |
| 8,784,882 B2 | 7/2014 | Mattern |
| 8,815,261 B2 | 8/2014 | Hanma |
| 8,846,648 B2 * | 9/2014 | Bernick ................. A61K 47/14 424/452 |
| 8,846,649 B2 * | 9/2014 | Bernick ................. A61P 15/12 424/452 |
| 8,933,059 B2 * | 1/2015 | Bernick ................. A61P 15/12 424/452 |
| 8,987,237 B2 * | 3/2015 | Bernick ............... A61K 9/4825 424/452 |
| 8,987,238 B2 * | 3/2015 | Bernick ................. A61K 9/48 424/452 |
| 8,993,548 B2 | 3/2015 | Bernick et al. |
| 8,993,549 B2 | 3/2015 | Bernick et al. |
| 9,006,222 B2 * | 4/2015 | Bernick ................. A61P 5/24 424/452 |
| 9,012,434 B2 * | 4/2015 | Bernick ................. A61K 9/48 424/452 |
| 9,114,145 B2 * | 8/2015 | Bernick ................. A61P 15/00 |
| 9,114,146 B2 * | 8/2015 | Bernick ............... A61K 9/7023 |
| 9,248,136 B2 * | 2/2016 | Bernick ................. A61K 31/57 |
| 10,052,386 B2 * | 8/2018 | Bernick ............... A61K 9/4825 |
| 10,471,148 B2 * | 11/2019 | Cacace ............... A61K 9/4825 |
| 10,639,375 B2 * | 5/2020 | Bernick ............... A61K 31/565 |
| 11,033,626 B2 * | 6/2021 | Cacace ................. A61K 31/57 |
| 2001/0005728 A1 | 6/2001 | Guittard et al. |
| 2001/0009673 A1 | 7/2001 | Lipp et al. |
| 2001/0021816 A1 | 9/2001 | Caillouette |
| 2001/0023261 A1 | 9/2001 | Ryoo et al. |
| 2001/0027189 A1 | 10/2001 | Bennink et al. |
| 2001/0029357 A1 | 10/2001 | Bunt et al. |
| 2001/0031747 A1 | 10/2001 | Deziegler et al. |
| 2001/0032125 A1 | 10/2001 | Bhan et al. |
| 2001/0034340 A1 | 10/2001 | Pickar |
| 2001/0053383 A1 | 12/2001 | Miranda et al. |
| 2001/0056068 A1 | 12/2001 | Chwalisz et al. |
| 2002/0012710 A1 | 1/2002 | Lansky |
| 2002/0026158 A1 | 2/2002 | Rathbone et al. |
| 2002/0028788 A1 | 3/2002 | Bunt et al. |
| 2002/0035070 A1 | 3/2002 | Gardlik et al. |
| 2002/0058648 A1 | 5/2002 | Hammerly |
| 2002/0058926 A1 | 5/2002 | Rathbone et al. |

(56) References Cited

U.S. PATENT DOCUMENTS

| | | |
|---|---|---|
| 2002/0064541 A1 | 5/2002 | Lapidot et al. |
| 2002/0076441 A1 | 6/2002 | Shih et al. |
| 2002/0102308 A1 | 8/2002 | Wei et al. |
| 2002/0107230 A1 | 8/2002 | Waldon et al. |
| 2002/0114803 A1 | 8/2002 | Deaver et al. |
| 2002/0119174 A1 | 8/2002 | Gardlik et al. |
| 2002/0119198 A1 | 8/2002 | Gao et al. |
| 2002/0132801 A1 | 9/2002 | Heil et al. |
| 2002/0137749 A1 | 9/2002 | Levinson et al. |
| 2002/0142017 A1 | 10/2002 | Simonnet |
| 2002/0151530 A1 | 10/2002 | Leonard et al. |
| 2002/0156394 A1 | 10/2002 | Mehrotra et al. |
| 2002/0169150 A1 | 11/2002 | Pickar |
| 2002/0169205 A1 | 11/2002 | Chwalisz et al. |
| 2002/0173510 A1 | 11/2002 | Levinson et al. |
| 2002/0193356 A1 | 12/2002 | Van Beek et al. |
| 2002/0193758 A1 | 12/2002 | Sandberg |
| 2002/0197286 A1 | 12/2002 | Brandman et al. |
| 2003/0003139 A1 | 1/2003 | Lipp et al. |
| 2003/0004145 A1 | 1/2003 | Leonard |
| 2003/0007994 A1 | 1/2003 | Bunt et al. |
| 2003/0027772 A1 | 2/2003 | Breton |
| 2003/0044453 A1 | 3/2003 | Dittgen et al. |
| 2003/0049307 A1 | 3/2003 | Gyurik |
| 2003/0064097 A1 | 4/2003 | Patel et al. |
| 2003/0064975 A1 | 4/2003 | Koch et al. |
| 2003/0072760 A1 | 4/2003 | Sirbasku |
| 2003/0073248 A1 | 4/2003 | Roth et al. |
| 2003/0073673 A1 | 4/2003 | Hesch |
| 2003/0077297 A1* | 4/2003 | Chen .................. A61K 38/13 424/400 |
| 2003/0078245 A1 | 4/2003 | Bennink et al. |
| 2003/0091620 A1 | 5/2003 | Fikstad et al. |
| 2003/0091640 A1 | 5/2003 | Ramanathan et al. |
| 2003/0092691 A1 | 5/2003 | Besse et al. |
| 2003/0096012 A1 | 5/2003 | Besse et al. |
| 2003/0104048 A1 | 6/2003 | Patel et al. |
| 2003/0109507 A1 | 6/2003 | Franke et al. |
| 2003/0113268 A1 | 6/2003 | Buenafae et al. |
| 2003/0114420 A1 | 6/2003 | Salvati et al. |
| 2003/0114430 A1 | 6/2003 | MacLeod et al. |
| 2003/0124182 A1 | 7/2003 | Shojaei et al. |
| 2003/0124191 A1 | 7/2003 | Besse et al. |
| 2003/0130558 A1 | 7/2003 | Massara et al. |
| 2003/0144258 A1 | 7/2003 | Heil et al. |
| 2003/0157157 A1 | 8/2003 | Luo et al. |
| 2003/0166509 A1 | 9/2003 | Edwards et al. |
| 2003/0170295 A1 | 9/2003 | Kim et al. |
| 2003/0175329 A1 | 9/2003 | Azarnoff et al. |
| 2003/0175333 A1 | 9/2003 | Shefer et al. |
| 2003/0180352 A1 | 9/2003 | Patel et al. |
| 2003/0181353 A1 | 9/2003 | Nyce |
| 2003/0181728 A1 | 9/2003 | Salvati et al. |
| 2003/0191096 A1 | 10/2003 | Leonard et al. |
| 2003/0195177 A1 | 10/2003 | Leonard et al. |
| 2003/0215496 A1 | 11/2003 | Patel et al. |
| 2003/0219402 A1 | 11/2003 | Rutter |
| 2003/0220297 A1 | 11/2003 | Berstein et al. |
| 2003/0224057 A1 | 12/2003 | Martin-Letellier et al. |
| 2003/0224059 A1 | 12/2003 | Lerner et al. |
| 2003/0225047 A1 | 12/2003 | Caubel et al. |
| 2003/0225048 A1 | 12/2003 | Caubel et al. |
| 2003/0225050 A1 | 12/2003 | Grawe et al. |
| 2003/0228686 A1 | 12/2003 | Klausner et al. |
| 2003/0229057 A1 | 12/2003 | Caubel et al. |
| 2003/0235596 A1 | 12/2003 | Gao et al. |
| 2003/0236236 A1 | 12/2003 | Chen et al. |
| 2004/0009960 A1 | 1/2004 | Heil et al. |
| 2004/0022820 A1 | 2/2004 | Anderson |
| 2004/0034001 A1 | 2/2004 | Karara |
| 2004/0037881 A1 | 2/2004 | Guittard et al. |
| 2004/0039356 A1 | 2/2004 | Maki et al. |
| 2004/0043043 A1 | 3/2004 | Schlyter et al. |
| 2004/0043943 A1 | 3/2004 | Guittard et al. |
| 2004/0044080 A1 | 3/2004 | Place et al. |
| 2004/0048900 A1 | 3/2004 | Flood |
| 2004/0052824 A1 | 3/2004 | Abou et al. |
| 2004/0073024 A1 | 4/2004 | Metcalf et al. |
| 2004/0077605 A1 | 4/2004 | Salvati et al. |
| 2004/0077606 A1 | 4/2004 | Salvati et al. |
| 2004/0087548 A1 | 5/2004 | Salvati et al. |
| 2004/0087564 A1 | 5/2004 | Wright et al. |
| 2004/0089308 A1 | 5/2004 | Welch |
| 2004/0092494 A9 | 5/2004 | Dudley |
| 2004/0092583 A1 | 5/2004 | Shanahan-Prendergast |
| 2004/0093261 A1 | 5/2004 | Jain et al. |
| 2004/0097468 A1 | 5/2004 | Wimalawansa |
| 2004/0101557 A1 | 5/2004 | Gibson et al. |
| 2004/0106542 A1 | 6/2004 | Deaver et al. |
| 2004/0110732 A1 | 6/2004 | Masini-Eteve et al. |
| 2004/0131670 A1 | 7/2004 | Gao |
| 2004/0138103 A1 | 7/2004 | Patt |
| 2004/0142012 A1 | 7/2004 | Bunt et al. |
| 2004/0146539 A1 | 7/2004 | Gupta |
| 2004/0146894 A1 | 7/2004 | Warrington et al. |
| 2004/0161435 A1 | 8/2004 | Gupta |
| 2004/0176324 A1 | 9/2004 | Salvati et al. |
| 2004/0176336 A1 | 9/2004 | Rodriguez |
| 2004/0185104 A1 | 9/2004 | Piao et al. |
| 2004/0191207 A1 | 9/2004 | Lipari et al. |
| 2004/0191276 A1 | 9/2004 | Muni |
| 2004/0198706 A1 | 10/2004 | Carrara et al. |
| 2004/0210280 A1 | 10/2004 | Liedtke |
| 2004/0213744 A1 | 10/2004 | Lulla et al. |
| 2004/0219124 A1 | 11/2004 | Gupta |
| 2004/0225140 A1 | 11/2004 | Fernandez et al. |
| 2004/0234606 A1 | 11/2004 | Levine et al. |
| 2004/0241219 A1 | 12/2004 | Hille et al. |
| 2004/0243437 A1 | 12/2004 | Grace et al. |
| 2004/0253319 A1 | 12/2004 | Netke et al. |
| 2004/0259817 A1 | 12/2004 | Waldon et al. |
| 2004/0266745 A1 | 12/2004 | Schwanitz et al. |
| 2005/0003003 A1 | 1/2005 | Basu et al. |
| 2005/0004088 A1 | 1/2005 | Hesch |
| 2005/0009800 A1 | 1/2005 | Thumbeck et al. |
| 2005/0014729 A1 | 1/2005 | Pulaski |
| 2005/0020550 A1 | 1/2005 | Morris et al. |
| 2005/0020552 A1 | 1/2005 | Aschkenasy et al. |
| 2005/0021009 A1 | 1/2005 | Massara et al. |
| 2005/0025833 A1 | 2/2005 | Aschkenasy et al. |
| 2005/0031651 A1 | 2/2005 | Gervais et al. |
| 2005/0042173 A1 | 2/2005 | Besse et al. |
| 2005/0042268 A1 | 2/2005 | Aschkenasy et al. |
| 2005/0048116 A1 | 3/2005 | Straub et al. |
| 2005/0054991 A1 | 3/2005 | Tobyn et al. |
| 2005/0079138 A1 | 4/2005 | Chickering et al. |
| 2005/0085453 A1 | 4/2005 | Govindarajan |
| 2005/0101579 A1 | 5/2005 | Shippen |
| 2005/0113350 A1 | 5/2005 | Duesterberg et al. |
| 2005/0118244 A1 | 6/2005 | Theobald et al. |
| 2005/0118272 A1 | 6/2005 | Besse et al. |
| 2005/0129756 A1 | 6/2005 | Podhaisky et al. |
| 2005/0152956 A1 | 7/2005 | Dudley |
| 2005/0153946 A1 | 7/2005 | Hirsh et al. |
| 2005/0164977 A1 | 7/2005 | Coelingh |
| 2005/0182105 A1 | 8/2005 | Nirschl et al. |
| 2005/0186141 A1 | 8/2005 | Gonda et al. |
| 2005/0187267 A1 | 8/2005 | Hamann et al. |
| 2005/0192253 A1 | 9/2005 | Salvati et al. |
| 2005/0192310 A1 | 9/2005 | Gavai et al. |
| 2005/0196434 A1 | 9/2005 | Brierre |
| 2005/0207990 A1 | 9/2005 | Funke et al. |
| 2005/0209209 A1 | 9/2005 | Koch et al. |
| 2005/0214384 A1 | 9/2005 | Juturu et al. |
| 2005/0220825 A1 | 10/2005 | Funke et al. |
| 2005/0220900 A1 | 10/2005 | Popp et al. |
| 2005/0222106 A1 | 10/2005 | Bracht |
| 2005/0228692 A1 | 10/2005 | Hodgdon |
| 2005/0228718 A1 | 10/2005 | Austin |
| 2005/0239747 A1 | 10/2005 | Yang et al. |
| 2005/0239758 A1 | 10/2005 | Roby |
| 2005/0244360 A1 | 11/2005 | Billoni |
| 2005/0244522 A1 | 11/2005 | Carrara et al. |
| 2005/0245902 A1 | 11/2005 | Cornish et al. |

(56) References Cited

U.S. PATENT DOCUMENTS

| | | |
|---|---|---|
| 2005/0250746 A1 | 11/2005 | Iammatteo |
| 2005/0250750 A1 | 11/2005 | Cummings et al. |
| 2005/0250753 A1 | 11/2005 | Fink et al. |
| 2005/0256028 A1 | 11/2005 | Yun et al. |
| 2005/0266078 A1 | 12/2005 | Jorda et al. |
| 2005/0266088 A1 | 12/2005 | Hinrichs et al. |
| 2005/0271597 A1 | 12/2005 | Keith |
| 2005/0271598 A1 | 12/2005 | Friedman et al. |
| 2005/0272685 A1 | 12/2005 | Hung |
| 2005/0272712 A1 | 12/2005 | Grubb et al. |
| 2006/0009428 A1 | 1/2006 | Grubb et al. |
| 2006/0014728 A1 | 1/2006 | Chwalisz et al. |
| 2006/0018937 A1 | 1/2006 | Friedman et al. |
| 2006/0019978 A1 | 1/2006 | Balog et al. |
| 2006/0020002 A1 | 1/2006 | Salvati et al. |
| 2006/0030615 A1 | 2/2006 | Fensome et al. |
| 2006/0034889 A1 | 2/2006 | Jo et al. |
| 2006/0034904 A1 | 2/2006 | Weimann |
| 2006/0051391 A1 | 3/2006 | Dvoskin et al. |
| 2006/0052341 A1 | 3/2006 | Cornish et al. |
| 2006/0069031 A1 | 3/2006 | Loumaye |
| 2006/0078618 A1 | 4/2006 | Constantinides et al. |
| 2006/0083778 A1 | 4/2006 | Allison et al. |
| 2006/0084704 A1 | 4/2006 | Shih et al. |
| 2006/0088580 A1 | 4/2006 | Meconi et al. |
| 2006/0089337 A1 | 4/2006 | Casper et al. |
| 2006/0093678 A1 | 5/2006 | Chickering, III |
| 2006/0100180 A1 | 5/2006 | Nubbemeyer et al. |
| 2006/0106004 A1 | 5/2006 | Brody et al. |
| 2006/0110415 A1 | 5/2006 | Gupta |
| 2006/0111424 A1 | 5/2006 | Salvati et al. |
| 2006/0121102 A1 | 6/2006 | Chiang |
| 2006/0121626 A1 | 6/2006 | Imrich et al. |
| 2006/0134188 A1 | 6/2006 | Podhaisky et al. |
| 2006/0135619 A1 | 6/2006 | Kick et al. |
| 2006/0165744 A1 | 7/2006 | Jamil et al. |
| 2006/0193789 A1 | 8/2006 | Tamarkin et al. |
| 2006/0194775 A1 | 8/2006 | Tofovic et al. |
| 2006/0204557 A1 | 9/2006 | Gupta et al. |
| 2006/0233743 A1 | 10/2006 | Kelly |
| 2006/0233841 A1 | 10/2006 | Brodbeck et al. |
| 2006/0235037 A1 | 10/2006 | Purandare et al. |
| 2006/0240111 A1 | 10/2006 | Fernandez et al. |
| 2006/0246122 A1 | 11/2006 | Langguth et al. |
| 2006/0247216 A1 | 11/2006 | Haj-Yehia |
| 2006/0247221 A1 | 11/2006 | Coelingh et al. |
| 2006/0251581 A1 | 11/2006 | McIntyre et al. |
| 2006/0252049 A1 | 11/2006 | Shuler et al. |
| 2006/0257472 A1 | 11/2006 | Nielsen |
| 2006/0275218 A1 | 12/2006 | Tamarkin et al. |
| 2006/0275360 A1 | 12/2006 | Ahmed et al. |
| 2006/0276414 A1 | 12/2006 | Coelingh et al. |
| 2006/0280771 A1 | 12/2006 | Groenewegen et al. |
| 2006/0280797 A1 | 12/2006 | Shoichet et al. |
| 2006/0280800 A1 | 12/2006 | Nagi et al. |
| 2006/0292223 A1 | 12/2006 | Woolfson et al. |
| 2007/0004693 A1 | 1/2007 | Woolfson et al. |
| 2007/0004694 A1 | 1/2007 | Woolfson et al. |
| 2007/0009559 A1 | 1/2007 | Li et al. |
| 2007/0009594 A1 | 1/2007 | Grubb et al. |
| 2007/0010550 A1 | 1/2007 | McKenzie |
| 2007/0014839 A1 | 1/2007 | Bracht |
| 2007/0015698 A1 | 1/2007 | Kleinman et al. |
| 2007/0021360 A1 | 1/2007 | Nyce et al. |
| 2007/0027201 A1 | 2/2007 | McComas et al. |
| 2007/0031491 A1 | 2/2007 | Levine et al. |
| 2007/0037780 A1 | 2/2007 | Ebert et al. |
| 2007/0037782 A1 | 2/2007 | Hibino et al. |
| 2007/0042038 A1 | 2/2007 | Besse |
| 2007/0060589 A1 | 3/2007 | Purandare et al. |
| 2007/0066628 A1 | 3/2007 | Zhang et al. |
| 2007/0066637 A1 | 3/2007 | Zhang et al. |
| 2007/0066675 A1 | 3/2007 | Zhang et al. |
| 2007/0078091 A1 | 4/2007 | Hubler et al. |
| 2007/0088029 A1 | 4/2007 | Balog et al. |
| 2007/0093548 A1 | 4/2007 | Diffendal et al. |
| 2007/0116729 A1 | 5/2007 | Palepu |
| 2007/0116829 A1 | 5/2007 | Prakash et al. |
| 2007/0128263 A1 | 6/2007 | Gargiulo et al. |
| 2007/0154533 A1 | 7/2007 | Dudley |
| 2007/0167418 A1 | 7/2007 | Ferguson |
| 2007/0178166 A1 | 8/2007 | Bernstein et al. |
| 2007/0184558 A1 | 8/2007 | Roth et al. |
| 2007/0185068 A1 | 8/2007 | Ferguson et al. |
| 2007/0190022 A1 | 8/2007 | Bacopoulos et al. |
| 2007/0191319 A1 | 8/2007 | Ke et al. |
| 2007/0196415 A1 | 8/2007 | Chen et al. |
| 2007/0196433 A1 | 8/2007 | Ron et al. |
| 2007/0207225 A1 | 9/2007 | Squadrito |
| 2007/0225281 A1 | 9/2007 | Zhang et al. |
| 2007/0232574 A1 | 10/2007 | Galey et al. |
| 2007/0238713 A1 | 10/2007 | Gast et al. |
| 2007/0243229 A1 | 10/2007 | Smith et al. |
| 2007/0248658 A1 | 10/2007 | Zurdo et al. |
| 2007/0254858 A1 | 11/2007 | Cronk |
| 2007/0255197 A1 | 11/2007 | Humberstone et al. |
| 2007/0264309 A1 | 11/2007 | Chollet et al. |
| 2007/0264345 A1 | 11/2007 | Eros et al. |
| 2007/0264349 A1 | 11/2007 | Lee et al. |
| 2007/0286819 A1 | 12/2007 | Devries et al. |
| 2007/0287688 A1 | 12/2007 | Chan et al. |
| 2007/0287789 A1 | 12/2007 | Jones et al. |
| 2007/0292359 A1 | 12/2007 | Friedman et al. |
| 2007/0292387 A1 | 12/2007 | Jon et al. |
| 2007/0292461 A1 | 12/2007 | Tamarkin et al. |
| 2007/0292493 A1 | 12/2007 | Brierre |
| 2007/0298089 A1 | 12/2007 | Saeki et al. |
| 2008/0026035 A1 | 1/2008 | Chollet et al. |
| 2008/0026040 A1 | 1/2008 | Farr et al. |
| 2008/0026062 A1 | 1/2008 | Farr et al. |
| 2008/0038219 A1 | 2/2008 | Mosbaugh et al. |
| 2008/0038350 A1 | 2/2008 | Gerecke et al. |
| 2008/0039405 A1 | 2/2008 | Langley et al. |
| 2008/0050317 A1 | 2/2008 | Tamarkin et al. |
| 2008/0051351 A1 | 2/2008 | Ghisalberti |
| 2008/0063607 A1 | 3/2008 | Tamarkin et al. |
| 2008/0069779 A1 | 3/2008 | Tamarkin et al. |
| 2008/0069791 A1 | 3/2008 | Beissert |
| 2008/0085877 A1 | 4/2008 | Bortz |
| 2008/0095831 A1 | 4/2008 | McGraw |
| 2008/0095838 A1 | 4/2008 | Abou |
| 2008/0113953 A1 | 5/2008 | De Vries et al. |
| 2008/0114050 A1 | 5/2008 | Fensome et al. |
| 2008/0119537 A1 | 5/2008 | Zhang et al. |
| 2008/0125402 A1 | 5/2008 | Diliberti et al. |
| 2008/0138379 A1 | 6/2008 | Jennings-Spring |
| 2008/0138390 A1 | 6/2008 | Hsu et al. |
| 2008/0139392 A1 | 6/2008 | Acosta-Zara et al. |
| 2008/0145423 A1 | 6/2008 | Khan et al. |
| 2008/0153789 A1 | 6/2008 | Dmowski et al. |
| 2008/0175814 A1 | 7/2008 | Phiasivongsa et al. |
| 2008/0175905 A1 | 7/2008 | Liu et al. |
| 2008/0175908 A1 | 7/2008 | Liu et al. |
| 2008/0188829 A1 | 8/2008 | Creasy et al. |
| 2008/0206156 A1 | 8/2008 | Cronk |
| 2008/0206159 A1 | 8/2008 | Tamarkin et al. |
| 2008/0206161 A1 | 8/2008 | Tamarkin et al. |
| 2008/0214512 A1 | 9/2008 | Seitz et al. |
| 2008/0220069 A1 | 9/2008 | Allison |
| 2008/0226698 A1 | 9/2008 | Tang et al. |
| 2008/0227763 A1 | 9/2008 | Lanquetin et al. |
| 2008/0234199 A1 | 9/2008 | Katamreddy |
| 2008/0234240 A1 | 9/2008 | Duesterberg et al. |
| 2008/0255078 A1 | 10/2008 | Katamreddy |
| 2008/0255089 A1 | 10/2008 | Katamreddy |
| 2008/0261931 A1 | 10/2008 | Hedner et al. |
| 2008/0299220 A1 | 12/2008 | Tamarkin et al. |
| 2008/0306036 A1 | 12/2008 | Katamreddy |
| 2008/0312197 A1 | 12/2008 | Rodriguez |
| 2008/0312198 A1 | 12/2008 | Rodriguez |
| 2008/0319078 A1 | 12/2008 | Katamreddy |
| 2009/0004246 A1 | 1/2009 | Woolfson et al. |
| 2009/0010968 A1 | 1/2009 | Allart et al. |
| 2009/0011041 A1 | 1/2009 | Musaeva et al. |

(56) References Cited

U.S. PATENT DOCUMENTS

| | | |
|---|---|---|
| 2009/0017120 A1 | 1/2009 | Trimble et al. |
| 2009/0022683 A1 | 1/2009 | Song et al. |
| 2009/0047357 A1 | 2/2009 | Tomohira et al. |
| 2009/0053294 A1 | 2/2009 | Prendergast |
| 2009/0060982 A1 | 3/2009 | Ron et al. |
| 2009/0060997 A1 | 3/2009 | Seitz et al. |
| 2009/0068118 A1 | 3/2009 | Eini et al. |
| 2009/0074859 A1 | 3/2009 | Patel |
| 2009/0081206 A1 | 3/2009 | Leibovitz |
| 2009/0081278 A1 | 3/2009 | De Graaff et al. |
| 2009/0081303 A1 | 3/2009 | Savoir et al. |
| 2009/0092656 A1 | 4/2009 | Klamerus et al. |
| 2009/0093440 A1 | 4/2009 | Murad |
| 2009/0098069 A1 | 4/2009 | Vacca |
| 2009/0099106 A1 | 4/2009 | Phiasivongsa et al. |
| 2009/0099149 A1 | 4/2009 | Liu et al. |
| 2009/0130029 A1 | 5/2009 | Tamarkin et al. |
| 2009/0131385 A1 | 5/2009 | Voskuhl |
| 2009/0137478 A1 | 5/2009 | Bernstein et al. |
| 2009/0137538 A1 | 5/2009 | Klamerus et al. |
| 2009/0143344 A1 | 6/2009 | Chang |
| 2009/0164341 A1 | 6/2009 | Sunvold et al. |
| 2009/0175799 A1 | 7/2009 | Tamarkin et al. |
| 2009/0181088 A1 | 7/2009 | Song et al. |
| 2009/0186081 A1 | 7/2009 | Holm et al. |
| 2009/0197843 A1 | 8/2009 | Notelovitz et al. |
| 2009/0203658 A1 | 8/2009 | Marx et al. |
| 2009/0214474 A1 | 8/2009 | Jennings |
| 2009/0227025 A1 | 9/2009 | Nichols et al. |
| 2009/0227550 A1 | 9/2009 | Mattern |
| 2009/0232897 A1 | 9/2009 | Sahoo et al. |
| 2009/0258096 A1 | 10/2009 | Cohen |
| 2009/0264395 A1 | 10/2009 | Creasy et al. |
| 2009/0269403 A1 | 10/2009 | Shaked et al. |
| 2009/0285772 A1 | 11/2009 | Phiasivongsa et al. |
| 2009/0285869 A1 | 11/2009 | Trimble |
| 2009/0318558 A1 | 12/2009 | Kim et al. |
| 2009/0324714 A1 | 12/2009 | Liu et al. |
| 2009/0325916 A1 | 12/2009 | Zhang et al. |
| 2010/0008985 A1 | 1/2010 | Pellikaan et al. |
| 2010/0028360 A1 | 2/2010 | Atwood |
| 2010/0034838 A1 | 2/2010 | Staniforth et al. |
| 2010/0034880 A1 | 2/2010 | Sintov et al. |
| 2010/0040671 A1 | 2/2010 | Ahmed et al. |
| 2010/0048523 A1 | 2/2010 | Bachman et al. |
| 2010/0055138 A1 | 3/2010 | Margulies et al. |
| 2010/0074959 A1 | 3/2010 | Hansom et al. |
| 2010/0086501 A1 | 4/2010 | Chang et al. |
| 2010/0086599 A1 | 4/2010 | Huempel et al. |
| 2010/0092568 A1 | 4/2010 | Lerner et al. |
| 2010/0105071 A1 | 4/2010 | Laufer et al. |
| 2010/0119585 A1 | 5/2010 | Hille et al. |
| 2010/0129320 A1 | 5/2010 | Phiasivongsa et al. |
| 2010/0136105 A1 | 6/2010 | Chen et al. |
| 2010/0137265 A1 | 6/2010 | Leonard |
| 2010/0137271 A1 | 6/2010 | Chen et al. |
| 2010/0143420 A1 | 6/2010 | Shenoy et al. |
| 2010/0143481 A1 | 6/2010 | Shenoy et al. |
| 2010/0150993 A1 | 6/2010 | Theobald et al. |
| 2010/0152144 A1 | 6/2010 | Hermsmeyer |
| 2010/0168228 A1 | 7/2010 | Bose et al. |
| 2010/0183723 A1 | 7/2010 | Laurent-Applegate et al. |
| 2010/0184736 A1 | 7/2010 | Coelingh et al. |
| 2010/0190758 A1 | 7/2010 | Fauser et al. |
| 2010/0204326 A1 | 8/2010 | D'Souza |
| 2010/0210994 A1 | 8/2010 | Zarif |
| 2010/0221195 A1 | 9/2010 | Tamarkin et al. |
| 2010/0227797 A1 | 9/2010 | Axelson et al. |
| 2010/0240626 A1 | 9/2010 | Kulkarni et al. |
| 2010/0247482 A1 | 9/2010 | Cui et al. |
| 2010/0247632 A1 | 9/2010 | Dong et al. |
| 2010/0247635 A1 | 9/2010 | Rosenberg et al. |
| 2010/0255085 A1* | 10/2010 | Liu ................. A61K 47/12 424/463 |
| 2010/0273730 A1 | 10/2010 | Hsu et al. |
| 2010/0278759 A1 | 11/2010 | Murad |
| 2010/0279988 A1 | 11/2010 | Setiawan et al. |
| 2010/0291191 A1 | 11/2010 | Shoichet et al. |
| 2010/0292199 A1 | 11/2010 | Leverd et al. |
| 2010/0303825 A9 | 12/2010 | Sirbasku |
| 2010/0312137 A1 | 12/2010 | Gilmour et al. |
| 2010/0316724 A1 | 12/2010 | Whitfield et al. |
| 2010/0322884 A1 | 12/2010 | Dipietro et al. |
| 2010/0330168 A1 | 12/2010 | Gicquel et al. |
| 2011/0028439 A1 | 2/2011 | Witt-Enderby et al. |
| 2011/0039814 A1 | 2/2011 | Huatan et al. |
| 2011/0053845 A1 | 3/2011 | Levine et al. |
| 2011/0066473 A1 | 3/2011 | Bernick et al. |
| 2011/0076775 A1 | 3/2011 | Stewart et al. |
| 2011/0076776 A1 | 3/2011 | Stewart et al. |
| 2011/0086825 A1 | 4/2011 | Chatroux |
| 2011/0087192 A1 | 4/2011 | Uhland et al. |
| 2011/0091555 A1 | 4/2011 | De Luigi Bruschi et al. |
| 2011/0098258 A1 | 4/2011 | Masini-Eteve et al. |
| 2011/0098631 A1 | 4/2011 | McIntyre et al. |
| 2011/0104268 A1 | 5/2011 | Pachot et al. |
| 2011/0104289 A1 | 5/2011 | Savoir et al. |
| 2011/0130372 A1 | 6/2011 | Agostinacchio et al. |
| 2011/0135719 A1 | 6/2011 | Besins et al. |
| 2011/0142945 A1 | 6/2011 | Chen et al. |
| 2011/0152840 A1 | 6/2011 | Lee et al. |
| 2011/0158920 A1 | 6/2011 | Morley et al. |
| 2011/0171140 A1 | 7/2011 | Illum et al. |
| 2011/0182997 A1 | 7/2011 | Lewis et al. |
| 2011/0190201 A1 | 8/2011 | Hyde et al. |
| 2011/0195031 A1 | 8/2011 | Du |
| 2011/0195114 A1 | 8/2011 | Carrara et al. |
| 2011/0195944 A1 | 8/2011 | Mura et al. |
| 2011/0217341 A1 | 9/2011 | Sah |
| 2011/0238003 A1 | 9/2011 | Bruno-Raimondi et al. |
| 2011/0244043 A1 | 10/2011 | Xu et al. |
| 2011/0250256 A1 | 10/2011 | Hyun-Oh et al. |
| 2011/0250259 A1 | 10/2011 | Buckman |
| 2011/0250274 A1 | 10/2011 | Shaked et al. |
| 2011/0256092 A1 | 10/2011 | Phiasivongsa et al. |
| 2011/0262373 A1 | 10/2011 | Umbert |
| 2011/0262494 A1 | 10/2011 | Achleitner et al. |
| 2011/0268665 A1 | 11/2011 | Tamarkin et al. |
| 2011/0275584 A1 | 11/2011 | Wilckens et al. |
| 2011/0281832 A1 | 11/2011 | Li et al. |
| 2011/0287094 A1 | 11/2011 | Penhasi et al. |
| 2011/0293720 A1 | 12/2011 | General et al. |
| 2011/0294738 A1 | 12/2011 | Ren et al. |
| 2011/0300167 A1 | 12/2011 | McMurry et al. |
| 2011/0301087 A1 | 12/2011 | McBride et al. |
| 2011/0306579 A1 | 12/2011 | Stein |
| 2011/0311592 A1 | 12/2011 | Birbara |
| 2011/0312927 A1 | 12/2011 | Nachaegari et al. |
| 2011/0312928 A1 | 12/2011 | Nachaegari et al. |
| 2011/0318405 A1 | 12/2011 | Erwin |
| 2011/0318431 A1 | 12/2011 | Gulati |
| 2012/0009276 A1 | 1/2012 | De Groote |
| 2012/0015350 A1 | 1/2012 | Nabatiyan et al. |
| 2012/0021041 A1 | 1/2012 | Rossi et al. |
| 2012/0028888 A1 | 2/2012 | Janz et al. |
| 2012/0028910 A1 | 2/2012 | Combal et al. |
| 2012/0028936 A1 | 2/2012 | Gloger et al. |
| 2012/0045532 A1 | 2/2012 | Cohen |
| 2012/0046264 A1 | 2/2012 | Simes et al. |
| 2012/0046518 A1 | 2/2012 | Yoakum et al. |
| 2012/0052077 A1 | 3/2012 | Truitt, III et al. |
| 2012/0058171 A1 | 3/2012 | De Graaff et al. |
| 2012/0058962 A1 | 3/2012 | Cumming et al. |
| 2012/0058979 A1 | 3/2012 | Keith et al. |
| 2012/0064135 A1 | 3/2012 | Levin et al. |
| 2012/0065179 A1 | 3/2012 | Andersson |
| 2012/0065221 A1 | 3/2012 | Babul |
| 2012/0087872 A1 | 4/2012 | Tamarkin et al. |
| 2012/0101073 A1 | 4/2012 | Mannion et al. |
| 2012/0121517 A1 | 5/2012 | Song et al. |
| 2012/0121692 A1 | 5/2012 | Xu et al. |
| 2012/0122829 A1 | 5/2012 | Taravella et al. |
| 2012/0128625 A1 | 5/2012 | Shalwitz et al. |
| 2012/0128654 A1 | 5/2012 | Terpstra et al. |

(56) References Cited

U.S. PATENT DOCUMENTS

| | | |
|---|---|---|
| 2012/0128683 A1 | 5/2012 | Shantha |
| 2012/0128733 A1 | 5/2012 | Perrin et al. |
| 2012/0128777 A1 | 5/2012 | Keck et al. |
| 2012/0129773 A1 | 5/2012 | Geier et al. |
| 2012/0129819 A1 | 5/2012 | Vancaillie et al. |
| 2012/0136013 A1 | 5/2012 | Li et al. |
| 2012/0142645 A1 | 6/2012 | Marx |
| 2012/0148670 A1 | 6/2012 | Kim et al. |
| 2012/0149748 A1 | 6/2012 | Shanler et al. |
| 2012/0172343 A1 | 7/2012 | Lindenthal et al. |
| 2012/0184515 A1 | 7/2012 | Klar et al. |
| 2012/0231052 A1 | 9/2012 | Sitruk-Ware et al. |
| 2012/0232011 A1 | 9/2012 | Kneissel et al. |
| 2012/0232042 A1 | 9/2012 | Klar et al. |
| 2012/0263679 A1 | 10/2012 | Marlow et al. |
| 2012/0269721 A1 | 10/2012 | Weng et al. |
| 2012/0269878 A2 | 10/2012 | Cantor et al. |
| 2012/0277249 A1 | 11/2012 | Andersson et al. |
| 2012/0277727 A1 | 11/2012 | Doshi et al. |
| 2012/0283671 A1 | 11/2012 | Shibata et al. |
| 2012/0295911 A1 | 11/2012 | Mannion et al. |
| 2012/0301517 A1 | 11/2012 | Zhang et al. |
| 2012/0301538 A1 | 11/2012 | Gordon-Beresford et al. |
| 2012/0302535 A1 | 11/2012 | Caufriez et al. |
| 2012/0316130 A1 | 12/2012 | Hendrix |
| 2012/0316496 A1 | 12/2012 | Hoffmann et al. |
| 2012/0321579 A1 | 12/2012 | Edelson et al. |
| 2012/0322779 A9 | 12/2012 | Voskuhl |
| 2012/0328549 A1 | 12/2012 | Edelson et al. |
| 2012/0329738 A1 | 12/2012 | Liu |
| 2013/0004619 A1 | 1/2013 | Chow et al. |
| 2013/0011342 A1 | 1/2013 | Tamarkin et al. |
| 2013/0017239 A1 | 1/2013 | Viladot et al. |
| 2013/0022674 A1 | 1/2013 | Dudley et al. |
| 2013/0023505 A1 | 1/2013 | Garfield et al. |
| 2013/0023823 A1 | 1/2013 | Simpson et al. |
| 2013/0028850 A1 | 1/2013 | Tamarkin et al. |
| 2013/0029947 A1 | 1/2013 | Nachaegari et al. |
| 2013/0029957 A1 | 1/2013 | Giliyar et al. |
| 2013/0045266 A1 | 2/2013 | Choi et al. |
| 2013/0045953 A1 | 2/2013 | Sitruk-Ware et al. |
| 2013/0059795 A1 | 3/2013 | Lo et al. |
| 2013/0064897 A1 | 3/2013 | Binay |
| 2013/0072466 A1 | 3/2013 | Choi et al. |
| 2013/0084257 A1 | 4/2013 | Ishida et al. |
| 2013/0085123 A1 | 4/2013 | Li et al. |
| 2013/0089574 A1 | 4/2013 | Schmidt-Gollwitzer et al. |
| 2013/0090318 A1 | 4/2013 | Ulmann et al. |
| 2013/0102781 A1 | 4/2013 | Bevill et al. |
| 2013/0108551 A1 | 5/2013 | Langereis et al. |
| 2013/0116215 A1 | 5/2013 | Coma et al. |
| 2013/0116222 A1 | 5/2013 | Arnold et al. |
| 2013/0122051 A1 | 5/2013 | Abidi et al. |
| 2013/0123175 A1 | 5/2013 | Hill et al. |
| 2013/0123220 A1 | 5/2013 | Queiroz |
| 2013/0123351 A1 | 5/2013 | Dewitt |
| 2013/0129818 A1 | 5/2013 | Bernick et al. |
| 2013/0131027 A1 | 5/2013 | Pakkalin et al. |
| 2013/0131028 A1 | 5/2013 | Snyder et al. |
| 2013/0131029 A1 | 5/2013 | Bakker et al. |
| 2013/0149314 A1 | 6/2013 | Bullerdiek et al. |
| 2013/0164225 A1 | 6/2013 | Tamarkin et al. |
| 2013/0164346 A1 | 6/2013 | Lee et al. |
| 2013/0165744 A1 | 6/2013 | Carson et al. |
| 2013/0178452 A1 | 7/2013 | King |
| 2013/0183254 A1 | 7/2013 | Zhou et al. |
| 2013/0183325 A1 | 7/2013 | Bottoni et al. |
| 2013/0189193 A1 | 7/2013 | Tamarkin et al. |
| 2013/0189196 A1 | 7/2013 | Tamarkin et al. |
| 2013/0189230 A1 | 7/2013 | Shoichet et al. |
| 2013/0189368 A1 | 7/2013 | Mosqueira et al. |
| 2013/0210709 A1 | 8/2013 | McMurry et al. |
| 2013/0216550 A1 | 8/2013 | Penninger et al. |
| 2013/0216596 A1 | 8/2013 | Viladot et al. |
| 2013/0224177 A1 | 8/2013 | Kim et al. |
| 2013/0224257 A1 | 8/2013 | Sah et al. |
| 2013/0224268 A1 | 8/2013 | Alam et al. |
| 2013/0224300 A1 | 8/2013 | Maggio |
| 2013/0225412 A1 | 8/2013 | Sardari et al. |
| 2013/0225542 A1 | 8/2013 | Poegh et al. |
| 2013/0226113 A1 | 8/2013 | Schumacher et al. |
| 2013/0243696 A1 | 9/2013 | Wang et al. |
| 2013/0245253 A1 | 9/2013 | Marx et al. |
| 2013/0245570 A1 | 9/2013 | Jackson |
| 2013/0261096 A1 | 10/2013 | Merian et al. |
| 2013/0266645 A1 | 10/2013 | Becker et al. |
| 2013/0267485 A1 | 10/2013 | Da Silva Maia Filho |
| 2013/0273167 A1 | 10/2013 | Lee et al. |
| 2013/0274211 A1 | 10/2013 | Burman et al. |
| 2013/0280213 A1 | 10/2013 | Voskuhl |
| 2013/0316374 A1 | 11/2013 | Penninger et al. |
| 2013/0317065 A1 | 11/2013 | Tatani et al. |
| 2013/0317315 A1 | 11/2013 | Lu et al. |
| 2013/0324565 A1 | 12/2013 | Li et al. |
| 2013/0331363 A1 | 12/2013 | Li et al. |
| 2013/0338122 A1 | 12/2013 | Bernick et al. |
| 2013/0338123 A1 | 12/2013 | Bernick et al. |
| 2013/0338124 A1 | 12/2013 | Li et al. |
| 2013/0345187 A1 | 12/2013 | Rodriguez |
| 2014/0018335 A1 | 1/2014 | Tatani et al. |
| 2014/0024590 A1 | 1/2014 | Weidhaas et al. |
| 2014/0031289 A1 | 1/2014 | Song et al. |
| 2014/0031323 A1 | 1/2014 | Perez |
| 2014/0066416 A1 | 3/2014 | Leunis et al. |
| 2014/0072531 A1 | 3/2014 | Kim et al. |
| 2014/0079686 A1 | 3/2014 | Barman et al. |
| 2014/0088051 A1 | 3/2014 | Bernick et al. |
| 2014/0088058 A1 | 3/2014 | Maurizio |
| 2014/0088059 A1 | 3/2014 | Perumal et al. |
| 2014/0094426 A1 | 4/2014 | Drummond et al. |
| 2014/0094440 A1 | 4/2014 | Bernick et al. |
| 2014/0094441 A1 | 4/2014 | Bernick et al. |
| 2014/0099362 A1 | 4/2014 | Bernick et al. |
| 2014/0100159 A1 | 4/2014 | Conrad |
| 2014/0100204 A1 | 4/2014 | Bernick et al. |
| 2014/0100205 A1 | 4/2014 | Bernick et al. |
| 2014/0100206 A1 | 4/2014 | Bernick et al. |
| 2014/0113889 A1 | 4/2014 | Connor et al. |
| 2014/0127185 A1 | 5/2014 | Stein et al. |
| 2014/0127280 A1 | 5/2014 | Duesterberg et al. |
| 2014/0127308 A1 | 5/2014 | Opara et al. |
| 2014/0128798 A1 | 5/2014 | Janson et al. |
| 2014/0148491 A1 | 5/2014 | Valia et al. |
| 2014/0186332 A1 | 7/2014 | Ezrin et al. |
| 2014/0187487 A1 | 7/2014 | Shoichet et al. |
| 2014/0193523 A1 | 7/2014 | Henry |
| 2014/0194396 A1 | 7/2014 | Li et al. |
| 2014/0206616 A1 | 7/2014 | Ko et al. |
| 2014/0213565 A1 | 7/2014 | Bernick et al. |
| 2014/0288035 A1 | 9/2014 | Hübner et al. |
| 2014/0329783 A1 | 11/2014 | Bernick et al. |
| 2014/0335193 A1 | 11/2014 | Rintoul et al. |
| 2014/0370084 A1 | 12/2014 | Bernick et al. |
| 2014/0371182 A1 | 12/2014 | Bernick et al. |
| 2014/0371183 A1 | 12/2014 | Bernick et al. |
| 2014/0371184 A1 | 12/2014 | Bernick et al. |
| 2014/0371185 A1 | 12/2014 | Bernick et al. |
| 2015/0031654 A1 | 1/2015 | Amadio |
| 2015/0045335 A1 | 2/2015 | Bernick et al. |
| 2015/0133421 A1 | 5/2015 | Bernick et al. |
| 2015/0148323 A1 | 5/2015 | Cacace et al. |
| 2015/0202211 A1 | 7/2015 | Amadio et al. |

FOREIGN PATENT DOCUMENTS

| | | |
|---|---|---|
| EP | 0275716 A1 | 7/1988 |
| EP | 0622075 A1 | 11/1994 |
| EP | 0785211 A1 | 7/1997 |
| EP | 0785212 A1 | 7/1997 |
| EP | 0811381 A1 | 12/1997 |
| EP | 0811381 B1 | 5/2003 |
| EP | 1094781 B1 | 7/2008 |
| EP | 2191833 A1 | 6/2010 |
| EP | 2191833 B1 | 2/2013 |

(56) References Cited

FOREIGN PATENT DOCUMENTS

| | | | |
|---|---|---|---|
| GB | 452238 A | 8/1936 |
| GB | 720561 A | 12/1954 |
| GB | 848881 A | 9/1960 |
| GB | 874368 A | 8/1961 |
| GB | 1589946 A | 5/1981 |
| IN | 216026 | 3/2008 |
| IN | 53/KOL/2005 | 9/2009 |
| IN | 244217 | 11/2010 |
| WO | WO-9011064 A1 | 10/1990 |
| WO | WO-9317686 A1 | 9/1993 |
| WO | WO-9422426 A1 | 10/1994 |
| WO | WO-9530409 A1 | 11/1995 |
| WO | WO-9609826 A2 | 4/1996 |
| WO | WO-9619975 A1 | 7/1996 |
| WO | WO-9630000 A1 | 10/1996 |
| WO | WO-9705491 A1 | 2/1997 |
| WO | WO-9743989 A1 | 11/1997 |
| WO | WO-9810293 A1 | 3/1998 |
| WO | WO-9832465 A1 | 7/1998 |
| WO | WO-9851280 A1 | 11/1998 |
| WO | WO-9932072 A1 | 7/1999 |
| WO | WO-9939700 A1 | 8/1999 |
| WO | WO-9942109 A1 | 8/1999 |
| WO | WO-9943304 A1 | 9/1999 |
| WO | WO-9948477 A1 | 9/1999 |
| WO | WO-9953910 A2 | 10/1999 |
| WO | WO-9963974 A2 | 12/1999 |
| WO | WO-0001351 A1 | 1/2000 |
| WO | WO-0006175 A1 | 2/2000 |
| WO | WO-0038659 A1 | 7/2000 |
| WO | WO-0045795 A2 | 8/2000 |
| WO | WO-0050007 A1 | 8/2000 |
| WO | WO-0059577 A1 | 10/2000 |
| WO | WO-0076522 A1 | 12/2000 |
| WO | WO-0137808 A1 | 5/2001 |
| WO | WO-0154699 A1 | 8/2001 |
| WO | WO-0160325 A1 | 8/2001 |
| WO | WO-0207700 A2 | 1/2002 |
| WO | WO-0211768 A1 | 2/2002 |
| WO | WO-0222132 A2 | 3/2002 |
| WO | WO-0240008 A2 | 5/2002 |
| WO | WO-0241878 A2 | 5/2002 |
| WO | WO-02053131 A1 | 7/2002 |
| WO | WO-02078604 A2 | 10/2002 |
| WO | WO-02078602 A3 | 2/2003 |
| WO | WO-03028667 A2 | 4/2003 |
| WO | WO-03041718 A1 | 5/2003 |
| WO | WO-03041741 A1 | 5/2003 |
| WO | WO-03068186 A1 | 8/2003 |
| WO | WO-03077923 A1 | 9/2003 |
| WO | WO-03082254 A1 | 10/2003 |
| WO | WO-03092588 A2 | 11/2003 |
| WO | WO-2004014397 A1 | 2/2004 |
| WO | WO-2004014432 A1 | 2/2004 |
| WO | WO-2004017983 A1 | 3/2004 |
| WO | WO-2004032897 A2 | 4/2004 |
| WO | WO-2004052336 A2 | 6/2004 |
| WO | WO-2004054540 A2 | 7/2004 |
| WO | WO-2004080413 A2 | 9/2004 |
| WO | WO-2005027911 A1 | 3/2005 |
| WO | WO-2005030175 A1 | 4/2005 |
| WO | WO-2005081825 A2 | 9/2005 |
| WO | WO-2005087194 A1 | 9/2005 |
| WO | WO-2005087199 A2 | 9/2005 |
| WO | WO-2005105059 A1 | 11/2005 |
| WO | WO-2005115335 A1 | 12/2005 |
| WO | WO-2005120470 A1 | 12/2005 |
| WO | WO-2005120517 A1 | 12/2005 |
| WO | WO-2006013369 A2 | 2/2006 |
| WO | WO-2006034090 A1 | 3/2006 |
| WO | WO-2006036899 A2 | 4/2006 |
| WO | WO-2006053172 A2 | 5/2006 |
| WO | WO-2006105615 A1 | 10/2006 |
| WO | WO-2006113505 A2 | 10/2006 |
| WO | WO-2006138686 A1 | 12/2006 |
| WO | WO-2006138735 A2 | 12/2006 |
| WO | WO-2007045027 A1 | 4/2007 |
| WO | WO-2007103294 A2 | 9/2007 |
| WO | WO-2006138735 A3 | 10/2007 |
| WO | WO-2007120868 A2 | 10/2007 |
| WO | WO-2007123790 A1 | 11/2007 |
| WO | WO-2007124250 A2 | 11/2007 |
| WO | WO-2007124250 A3 | 12/2007 |
| WO | WO-2007144151 A1 | 12/2007 |
| WO | WO-2007103294 A3 | 4/2008 |
| WO | WO-2008049516 A3 | 6/2008 |
| WO | WO-2008152444 A2 | 12/2008 |
| WO | WO-2009002542 A1 | 12/2008 |
| WO | WO-2009036311 A1 | 3/2009 |
| WO | WO-2009040818 A1 | 4/2009 |
| WO | WO-2008152444 A3 | 6/2009 |
| WO | WO-2009069006 A2 | 6/2009 |
| WO | WO-2009098072 A2 | 8/2009 |
| WO | WO-2009098072 A3 | 10/2009 |
| WO | WO-2009069006 A3 | 11/2009 |
| WO | WO-2009133352 A2 | 11/2009 |
| WO | WO-2010033188 A2 | 3/2010 |
| WO | WO-2009133352 A3 | 10/2010 |
| WO | WO-2010146872 A1 | 12/2010 |
| WO | WO-2011000210 A1 | 1/2011 |
| WO | WO-2011073995 A2 | 6/2011 |
| WO | WO-2011073995 A3 | 8/2011 |
| WO | WO-2010033188 A3 | 9/2011 |
| WO | WO-2011120084 A1 | 10/2011 |
| WO | WO-2011128336 A1 | 10/2011 |
| WO | WO-2012009778 A2 | 1/2012 |
| WO | WO-2012024361 A1 | 2/2012 |
| WO | WO-2012055814 A1 | 5/2012 |
| WO | WO-2012055840 A1 | 5/2012 |
| WO | WO-2012065740 A1 | 5/2012 |
| WO | WO-2012098090 A1 | 7/2012 |
| WO | WO-2012116277 A1 | 8/2012 |
| WO | WO-2012118563 A2 | 9/2012 |
| WO | WO-2012120365 A1 | 9/2012 |
| WO | WO-2012127501 A2 | 9/2012 |
| WO | WO-2012156561 A1 | 11/2012 |
| WO | WO-2012156822 A1 | 11/2012 |
| WO | WO-2012158483 A2 | 11/2012 |
| WO | WO-2012166909 A1 | 12/2012 |
| WO | WO-2012170578 A1 | 12/2012 |
| WO | WO-2013011501 A1 | 1/2013 |
| WO | WO-2012009778 A3 | 2/2013 |
| WO | WO-2013025449 A2 | 2/2013 |
| WO | WO-2013028639 A1 | 2/2013 |
| WO | WO-2013035101 A1 | 3/2013 |
| WO | WO-2013044067 A1 | 3/2013 |
| WO | WO-2013045404 A2 | 4/2013 |
| WO | WO-2013059285 A1 | 4/2013 |
| WO | WO 2013/078422 A2 | 5/2013 |
| WO | WO-2013063279 A1 | 5/2013 |
| WO | WO-2013064620 A1 | 5/2013 |
| WO | WO-2013071281 A1 | 5/2013 |
| WO | WO-2013088254 A1 | 6/2013 |
| WO | WO-2013102665 A1 | 7/2013 |
| WO | WO-2013106437 A1 | 7/2013 |
| WO | WO-2013113690 A1 | 8/2013 |
| WO | WO-2013124415 A1 | 8/2013 |
| WO | WO-2013127727 A1 | 9/2013 |
| WO | WO-2013127728 A1 | 9/2013 |
| WO | WO-2013144356 A1 | 10/2013 |
| WO | WO-2013149258 A2 | 10/2013 |
| WO | WO-2013158454 A2 | 10/2013 |
| WO | WO-2013170052 A1 | 11/2013 |
| WO | WO-2013178587 A1 | 12/2013 |
| WO | WO-2013181449 A1 | 12/2013 |
| WO | WO-2013192248 A1 | 12/2013 |
| WO | WO-2013192249 A1 | 12/2013 |
| WO | WO-2013192250 A1 | 12/2013 |
| WO | WO-2013192251 A1 | 12/2013 |
| WO | WO-2014001904 A1 | 1/2014 |
| WO | WO-2014004424 A1 | 1/2014 |
| WO | WO-2014009434 A1 | 1/2014 |
| WO | WO-2014018569 A1 | 1/2014 |
| WO | WO-2014018570 A1 | 1/2014 |

(56) References Cited

FOREIGN PATENT DOCUMENTS

| WO | WO-2014018571 A2 | 1/2014 |
|---|---|---|
| WO | WO-2014018856 A1 | 1/2014 |
| WO | WO-2014018932 A2 | 1/2014 |
| WO | WO-2014031958 A1 | 2/2014 |
| WO | WO-2014041120 A1 | 3/2014 |
| WO | WO-2014052792 A1 | 4/2014 |
| WO | WO-2014056897 A1 | 4/2014 |
| WO | WO-2014066442 A2 | 5/2014 |
| WO | WO-2014074846 A1 | 5/2014 |
| WO | WO-2014076231 A1 | 5/2014 |
| WO | WO-2014076569 A2 | 5/2014 |
| WO | WO-2014081598 A1 | 5/2014 |
| WO | WO-2014086739 A1 | 6/2014 |
| WO | WO-2014093114 A1 | 6/2014 |
| WO | WO-2014104784 A1 | 7/2014 |

OTHER PUBLICATIONS

Abbas, M.A., et al., "Regression of Endometrial Implants Treated with Vitamin D3 in a Rat Model of Endometriosis," European Journal of Pharmacology 715(1-3):72-75, Elsevier Science, Netherlands (2013).
Abitec, CapmuiMCM, EP, Technical Data Sheet, version 10, 2014, Columbus, OH.
Abitec, CapmuiMCM, NF, Technical Data Sheet, version 6, 2014, Columbus, OH.
Abitec, CapmuiMCM, Safley Data Sheet, 2011, Janesville, WI.
Abitec, CapmuiMCM, Technical Data Sheet, version 17, 2014, Columbus, OH.
Abitec, CapmuiPG8, CAS No. 31565-12-5, version 11,2006, Columbus, OH.
Abitec Corporation Excipients for the Pharmaceutical Industry—Regulatory and Product Information, 2 pages (2013).
Acarturk, F., "Mucoadhesive Vaginal Drug Delivery Systems," Recent patents on drug delivery & formulation 3(3):193-205, Bentham Science Publishers, United Arab Emirates (2009).
Acog, Mckinlay, et al., "Practice Bulletin, Clinical Management Guidelines for Obstetrician-Gynecologists,", Obstetrics & Gynecology Agog, No. 141, vol. 123(1), 202-216, (2014).
Advisory Action dated Jan. 29, 2007 for U.S. Appl. No. 12/561,515, filed Sep. 17, 2009.
Alabi, K. A., et al., "Analysis of Fatty Acid Composition ofThevetia peruviana and Hura crepitans Seed oils using GC-FID," Fountain Journal of Natural and Applied Sciences 2(2):32-7, Osogbo (2013).
Alexander, KS, Corn Oil, CAS No. 8001-30-7, (2009).
Alvarez, P., et al., "Ectopic Uterine Tissue as a Chronic Pain Generator," Neuroscience 225:269-282, Elsevier Science, United States (2012).
Application Note JASCO CD Spectra of Pharmaceuticals Substances Steroids, 2 pages.
Araya-Sibaja, A.M., et al., "Morphology Study of Progesterone Polymorphs Prepared by Polymer-induced Heteronucleation (Pihn)," Scanning 35(4):213-221, John Wiley & Sons, United States (2013).
Araya-Sibaja, Andrea Manela, et al., "Chemical Properties of Progesterone Selected Refer," SciFinder, American Chemical Society & US National. Library. of Med, (2014).
Araya-Sibaja, Andrea Manela, et al., "Polymorphism in Progesterone," SciFinder, pp. 1-46, American Chemical Society & US National. Library. of Med, (2014).
Araya-Sibaja, Andrea Manela, et al., "Polymorphism in Progesterone Selected References," SciFinder, pp. 1-12, American Chemical Society & US National. Library. of Med, (2014).
Araya-Sibaja., et al., "Crystallization of progesterone polymorphs using polymer-induced heteronucleation (PIHn) method," Drug Development and Industrial Pharmacy, Early Online, pp. 1-8, Informa Healthcare (2014).
Archer, D.F., et al., "Effects of Ospemifene on the Female Reproductive and Urinary Tracts : Translation From Preclinical Models into Clinical Evidence," Menopause, Lippincott-Raven Publishers, United States (2014).

Archer, F., et al., Estrace® vs Premarin® for Treatment of Menopausal Symptoms: Dosage Comparison Study 9(1):21-31, (1992).
Ashburn, A.D., et al., "Cardiovascular , Hepatic and Renal Lesions in Mice Receiving Cortisone , Estrone and Progesterone," The Yale Journal of Biology and Medicine 35:329-340, Yale Journal of Biology and Medicine, United States (1963).
Azeem, A., et al., "Microemulsions as a Surrogate Carrier for Dermal Drug Delivery," Drug development and industrial pharmacy 35(5):525-547, Informa Healthcare, England (2009).
Azure Pharma, Inc., "Elestrin—estradiol gel" Drug Info, http://dailymed.nlm.nih.gov/dailymed/archives/ fdaDrugInfo.cfm?archiveid=11885, 26 pages, (2009).
Bakhmutova-Albert, Ekaterina, et al.,"Enhancing Aqueous Dissolution Rates of Progesterone via Cocrystallization," SSCI, Division of Aptuit, Poster No. R6247, West Lafayette.
Banerjee, S., et al., "on the Stability of Salivary Progesterone Under Various Conditions of Storage," Steroids 46(6):967-974, Elsevier, United States (1985).
Barnett. and Steven, M., "Pressure-tuning infared and solution Raman spectroscopic studies of 17B-estradiol and several A-ring," Vibrational Spectroscopy, vol. 8, pp. 263, (1995).
Bartosova, L. and Bajgar, J., "Transdermal Drug Delivery in Vitro Using Diffusion Cells," Current Medicinal Chemistry 19(27):4671-4677, Bentham Science Publishers, Netherlands (2012).
Benbow, A.L. and Waddell, B.J., "Distribution and Metabolism of Maternal Progesterone in the Uterus, Placenta, and Fetus During Rat Pregnancy," Biology of Reproduction 52(6):1327-1333, Society for the Study of Reproduction, United States (1995).
Bernabei, M.T., et al., "[Release of Polymorphic forms of Progesterone From Dimethylpolysiloxane Matrices]," Bollettino chimico farmaceutico 122(1):20-26, Societa Editoriale Farmaceutica, Italy (1983).
Bernard, et al., "Structure Cristalline et Moleculaire du Complexe Oestradiol-Propanol," Acta Crystallographica B28 :1349, (1972).
Bernard Hospital and Michel Busetta, "Structure Cristalline et Moleculair de !'Oestradiol Hemihydrate," Acta Crystallographica B28 :560-567, (1972).
Bhavnani, B.R. and Stanczyk, F.Z., "Misconception and Concerns About Bioidentical Hormones Used for Custom-Compounded Hormone Therapy," The Journal of clinical endocrinology and metabolism 97(3):756-759, Endocrine Society, United States (2012).
Bhavnani, B.R. and Stanczyk, F.Z., "Pharmacology of Conjugated Equine Estrogens: Efficacy, Safety and Mechanism of Action," The Journal of steroid biochemistry and molecular biology 142:16-29, Pergamon, England (2014).
Bhavnani, B.R., et al., "Structure Activity Relationships and Differential interactions and Functional Activity of Various Equine Estrogens Mediated via Estrogen Receptors (Ers) Eralpha and Erbeta," Endocrinology 149(10):4857-4870, Endocrine Society, United States (2008).
BioMed Centrai,Solubility of Progesterone in Organic Solvents, Online PDF, http://www.biomedcentral.com/content/ supplementary/1475-2859-11-106-S2.pdf.
Blake, E.J., et al., "Single and Multidose Pharmacokinetic Study of a Vaginal Micronized Progesterone insert (Endometrin ) Compared with Vaginal Gel in Healthy Reproductive-Aged Female Subjects," Fertility and Sterility 94(4):1296-1301, Elsevier for the American Society for Reproductive Medicine, United States (2010).
Borka. and Laszlo., Crystal Polymorphism of Pharmaceuticals, Acta Pharmaceutica Jugoslavia 40:71-94, (1990).
Brandstatter-Kuhnert, M., Kofler A., "Zur mikroskopischen ldentitatsprufung und zur Polymorphie der Sexualhormone," Microchimica Acta 6:847-853, Springer-Verlag, Germany (1959).
Brared Christensson, J., et al., "Positive Patch Test Reactions to Oxidized Limonene: Exposure and Relevance," Contact Dermatitis 71(5):264-272, Wiley, England (2014).
Brinton, L.A. and Felix, A.S., "Menopausal Hormone Therapy and Risk of Endometrial Cancer," The Journal of steroid biochemistry and molecular biology 142:83-89, Pergamon, England (2014).
"British Pharmacopoeia 2014 Online, Refined Maize Oil, Ph. Eur. Monograph 1342, voll & II, Monographs: Medicinal and Pharma-

(56) References Cited

OTHER PUBLICATIONS ceutical Substances, accessed at http:/www.pharmacopoeia.co.uklbp2014/ixbin/bp.egi?a=print&id=7400&tab=a-z% 20index[2/3/2014 1:37:50 PM]".
Burry, K.A., et al., "Percutaneous Absorption of Progesterone in Postmenopausal Women Treated with Transdermal Estrogen," American journal of obstetrics and gynecology 180(6Pt1):1504-1511, Elsevier, United States (1999).
Campsteyn, H., et al., "Structure Cristalline et Molcculaire de Ia Progesterone C21H3002," Acta Crystallographica B28 :3032-3042, (1972).
Cendejas-Santana, G., et al., "Growth and characterization of progesterone crystallites," Revista Mexicana de Fisica 50 S(1) : 1-3, (2004).
ChemPro, Top-Notch Technology in Production of Oils and Fats, Chempro-Edible-Oii-Refining-ISO-TUV-Austria.
Christen, R.D., et al., "Phase I/Pharmacokinetic Study of High-Dose Progesterone and Doxorubicin," Journal of Clinical Oncology : Official Journal of the American Society of Clinical Oncology 11(12):2417-2426, American Society of Clinical Oncology, United States (1993).
Christensson, J.B., et al., "Limonene Hydroperoxide Analogues Differ in Allergenic Activity," Contact Dermatitis 59(6):344-352, Wiley, England (2008).
Christensson, J.B., et al., "Limonene Hydroperoxide Analogues Show Specific Patch Test Reactions," Contact Dermatitis 70(5):291-299, Wiley, England (2014).
Chun et al., "Transdermal Delivery of Estradiol and Norethindrone Acetate: Effect of Vehicles and Pressure Sensitive Adhesive Matrix," Journal of Korean Pharmaceutical Sciences 35(3):173-177, (2005).
Cicinelli, E., et al., "Direct Transport of Progesterone From Vagina to Uterus," Obstetrics and Gynecology 95(3):403-406, Lippincott Williams & Wilkins, United States (2000).
Committee of Obstetric Practice, Committee Opinion—No. 522, Obstetrics & Gynecology, 119(4):879-882, (2012).
Commodari, F., et al., "Comparison of 17Beta-Estradiol Structures From X-Ray Diffraction and Solution Nmr," Magnetic resonance in chemistry : MRC 43(6):444-450, Wiley Heyden, England (2005).
Cooper, A., et al., "Systemic Absorption of Progesterone From Progest Cream in Postmenopausal Women," Lancet 351(9111):1255-1256, Lancet Publishing Group, England (1998).
International Search Report and written opinion for International Application No. PCT/US13/46442, dated Nov. 1, 2013.
International Search Report and written opinion for International Application No. PCT/US13/46443, dated Oct. 31, 2013.
International Search Report and written opinion for International Application No. PCT/US13/46444, dated Oct. 31, 2013.
International Search Report and written opinion for International Application No. PCT/US13/46445, dated Nov. 1, 2013.
International Search Report and Written Opinion for related International Application No. PCT/US13/023309, dated Apr. 9, 2013.
International Search report for corresponding International Application No. PCT/US12/66406, dated Jan. 24, 2013.
Corbett, S.H., et al., "Trends in Pharmacy Compounding for Women'S Health in North Carolina : Focus on Vulvodynia," Southern Medical Journal 107(7):433-436, Southern Medical Association, United States (2014).
Corn Refiners Assoc. Com Oil, Edition 5, United States (2006).
Critchley, H.O., et al., "Estrogen Receptor Beta, but Not Estrogen Receptor Alpha, Is Present in the Vascular Endothelium of the Human and Nonhuman Primate Endometrium," The Journal of Clinical Endocrinology and Metabolism 86(3):1370-1378, Endocrine Society, United States (2001).
Dauqan, Eqbal M.A., et al., "Fatty Acids Composition of Four Different Vegetable Oils (Red Palm Olein, Palm Olein, Corn Oil," IPCBEE, 14, lACSIT Press, Singapore (2011).
Dideberg, O., et al., "Crystal data on progesterone (C21H3002), desoxycorticosterone (C21H3003), corticosterone (C21H3004) and aldosterone," Journal of Applied Crystallography 4:80, (1971).

Diramio, J.A., et al., "Poly(Ethylene Glycol) Methacrylate/Dimethacrylate Hydrogels for Controlled Release of Hydrophobic Drugs," Masters of Science Thesis, University of Georgia, Athens, Georgia, 131 pages (2002).
Diramio. "Polyethylene Glycol Methacrylate/Dimetacrylate Hydrogels for Controlled Release of Hydrophobic Drugs," The University of Georgia-Masters of Science Thesis, http://athenaeum.libs.uga.edu/bitstream/handle/10724/7820/diramio_jackie_a_200412_ms.pdf?sequence=1, , 131 pages, (2004).
Drakulic, B.J., et al., "Role of Complexes formation Between Drugs and Penetration Enhancers in Transdermal Delivery," International journal of pharmaceutics 363(1-2):40-49, Elsevier/North-Holland Biomedical Press., Netherlands (2008).
Du, J.Y., et al., "Percutaneous Progesterone Delivery via Cream or Gel Application in Postmenopausal Women : A Randomized Cross-Over Study of Progesterone Levels in Serum , Whole Blood , Saliva, and Capillary Blood," Menopause 20(11):1169-1175, Lippincott-Raven Publishers, United States (2013).
Duclos, R., et al., "Polymorphism of Progesterone: Influence of the carrier and of the solid dispersion manufacturing process. A calorimetric and radiocrystallographic study," Journal of Thermal Analysis 37:1869-1875, John Wiley & Sons, England (1991).
Ebian, A.R., "Ebian Article: Polymorphism and solvation of ethinyl estradiol," Pharmaceutica Acta Helvetiae 54(4):111-114, (1979).
Eisenberger, A. and Westhoff, C., "Hormone Replacement Therapy and Venous Thromboembolism," The Journal of steroid biochemistry and molecular biology 142:76-82, Pergamon, England (2014).
Engelhardt, H., et al., "Conceptus influences the Distribution of Uterine Leukocytes During Early Porcine Pregnancy," Biology of Reproduction 66(6):1875-1880, Society for the Study of Reproduction, United States (2002).
Ettinger, B., et al., "Comparison of Endometrial Growth Produced by Unopposed Conjugated Estrogens or by Micronized Estradiol in Postmenopausal Women," American Journal of Obstetrics and Gynecology 176(1 Pt1):112-117, Elsevier, United States (1997).
Excipients for Pharmaceuticals, Sasol Olefins & Surfactants GMBH, 28 pages (2010).
Faassen, F., et al., "Physicochemical Properties and Transport of Steroids Across Caco-2 Cells," Pharmaceutical research 20(2):177-186, Kluwer Academic/Plenum Publishers, United States (2003).
"FDA, Draft Guidance on Progesterone, accessed at http://www.fda.gov/downloads/Drugs/GuidanceComplianceRegulatoryInformation/Guidances/UCM209294.pdf, accessed on (Recommended) Apr. 2010,(Revised) Feb. 2011,".
Ferrari, Roseli AP., et al., "Oxidative Stability of Biodiesel From Soybean Oil Fatty Acid Ethyl Esters," Scientia Agricola 62(3):291-95, Piracicaba, brazil (2005).
Filipsson,F., et al., "Concise International Chemical Assessment Document 5," Limonene, first draft, World Health Organization, Geneva, 36 pages (1998).
Final Office Action dated Jul. 16, 2013 for U.S. Appl. No. 13/684,002, filed Nov. 21, 2012.
Final Office Action dated Oct. 26,2012for U.S. Appl. No. 12/561,515, filed Sep. 17, 2009.
Flyvholm, M.A. and Menne, T., "Sensitizing Risk of butylated Hydroxytoluene Based on Exposure and Effect Data," Contact Dermatitis 23(5):341-345, Wiley, England (1990).
Fotherby. K., "Bioavailability of Orally Administered Sex Steroids Used in Oral Contraception and Hormone Replacement Therapy," Contraception 54(2):59-69, Elsevier, United States (1996).
Franklin, R.D. and Kutteh, W.H., "Characterization of Immunoglobulins and Cytokines in Human Cervical Mucus : influence of Exogenous and Endogenous Hormones," Journal of Reproductive Immunology 42(2):93-106, Elsevier/North-Holland Biomedical Press, Ireland (1999).
Franz, T.J., et al., "Use of Excised Human Skin to Assess the Bioequivalence of Topical Products," Skin Pharmacology and Physiology 22(5):276-286, Karger, Switzerland (2009).
Freedman, R.R., "Menopausal Hot Flashes: Mechanisms, Endocrinology, Treatment," The Journal of steroid biochemistry and molecular biology 142:115-120, Pergamon, England (2014).

(56) References Cited

OTHER PUBLICATIONS

Fuchs, K.O., et al., "The Effects of an Estrogen and Glycolic Acid Cream on the Facial Skin of Postmenopausal Women: A Randomized Histologic Study," Aesthetic Dermatology 8(1):14-19, (2006).
Fuchs, K.O., et al., "The Effects of an Estrogen and Glycolic Acid Cream on the Facial Skin of Postmenopausal Women: A Randomized Histologic Study," Cutis 71(6):481-488, Frontline Medical Communications, United States (2003).
Fuchs, K.O., et al., "The Effects of an Estrogen and Glycolic Acid Cream on the Facial Skin of Postmenopausal Women: A Randomized Histologic Study," Pharmacology/Cosmetology 5(1), (2006).
Fugh-Berman, A. and Bythrow, J., "Bioidentical Hormones for Menopausal Hormone Therapy: Variation on a Theme," Journal of general internal medicine 22(7):1030-1034, Springer, United States (2007).
Furness, S., et al., "Hormone therapy in Postmenopausal Women and Risk of Endometrial Hyperplasia," The Cochrane Database of Systematic Reviews 8:1-204, Wiley, England (2012).
Gafvert, E., et al., "Free Radicals in Antigen formation: Reduction of Contact Allergic Response to Hydroperoxides by Epidermal Treatment with Antioxidants," The British Journal of Dermatology 146(4):649-656, Blackwell Scientific Publications, England (2002).
Ganem-Quintanar., et al., "Evaluation of the transepidermal permeation of diethylene glycol monoethyl ether and skin water loss," International Journal of Pharmaceutics, 147(2):165-171, (1997) Abstract Only.
Gattefossé SAS, Regulatory Data Sheet, Gelot 64, 6 pages (2012).
Gattefossé SAS, Regulatory Data Sheet, Lauroglycol 90, 5 pages (2012).
Gattefosse, "Excipients for Safe and Effective Topical Delivery," http://drug-dev.com/Main/Back-Issues/Transdermal-Topical-Subcutaneous-NonInvasive-Deliv-5.aspx# (2012).
Gattefosse SAS, Material Safety Data Sheet, Gelot 64, 8 pages 2012.
Gillet, J.Y., et al., "induction of Amenorrhea During Hormone Replacement therapy : Optimal Micronized Progesterone Dose a Multicenter Study," Maturitas 19(2):103-115, Elsevier/North Holland Biomedical Press, Ireland (1994).
Giron, D., "Thermal analysis and calorimetric methods in the characterisation of polymorphs and solvates," Thermochimica Acta 248:1-59, Elsevier B.V., Netherlands (1995).
Giron-Forest, D., et al., "Thermal Analysis Methods for Pharmacopoeial Materials," Journal of pharmaceutical and biomedical analysis 7(12):1421-1433, Elsevier Science, England (1989).
Glaser, R.L., et al., "Pilot Study : Absorption and Efficacy of Multiple Hormones Delivered in a Single Cream Applied to the Mucous Membranes of the Labia and Vagina," Gynecologic and Obstetric Investigation 66(2):111-118,Basel, New York, Karger., Switzerland (2008).
Golatowski, C., et al., "Comparative Evaluation of Saliva Collection Methods for Proteome Analysis," International Journal of Clinical Chemistry 419:42-46,Elsevier., Netherlands (2013).
Graham, J.D. and Clarke, C.L., "Physiological Action of Progesterone in Target Tissues," Endocrine Reviews 18(4):502-519, Endocrine Society, United States (1997).
Groothuis, P.G., et al., "Estrogen and the Endometrium : Lessons Learned From Gene Expression Profiling in Rodents and Human," Human Reproduction Update 13(4):405-417, Published for the European Society of Human Reproduction and Embryology by Oxford University Press, England (2007).
Gunstone, Frank, D., et al., "Vegetable Oils in Food Technology: Composition, Properties and Uses," Blackwell Publishing, CRC Press, (2002).
Gurney, E.P., et al., "The Women"S Health initiative Trial and Related Studies: 10 Years Later: A Clinician"S View," The Journal of steroid biochemistry and molecular biology 142:42105, Pergamon, England (2014).
Hamid, K.A., et al., "the Effects of Common Solubilizing Agents on the intestinal Membrane Barrier Functions and Membrane Toxicity in Rats," International Journal of Pharmaceutics 379(1):100-108,Amsterdam, Elsevier/North-Holland Biomedical Press., Netherlands (2009).
Hapgood, J.P., et al., "Potency of Progestogens Used in Hormonal Therapy: Toward Understanding Differential Actions," The Journal of steroid biochemistry and molecular biology 142:39-47, Pergamon, England (2014).
Hargrove, J.T., et al., "Menopausal Hormone Replacement Therapy with Continuous Daily Oral Micronized Estradiol and Progesterone," Obstetrics and gynecology 73(4):606-612, Lippincott Williams & Wilkins, United States (1989).
Harner B.A., and Norton, D.A., "Crystal data (I) for some pregnenes and pregnadienes," Acta Crystallographica 17:1610, (1964).
Hatton, J., et al., "Safety and Efficacy of a Lipid Emulsion Containing Medium-Chain Triglycerides," Clinical Pharmacy 9(5):366-371, American Society of Hospital Pharmacists, United States (1990).
He, F., et al., "Apoptotic Signaling Pathways in Uteri of Rats with Endometrial Hyperplasia induced by Ovariectomy Combined with Estrogen," Gynecologic and Obstetric Investigation 76(1):51-56,Karger., Switzerland (2013).
Helbling, I.M., et al., "The Optimization of an intravaginal Ring Releasing Progesterone Using a Mathematical Model," Pharmaceutical research 31(3):795-808, Kluwer Academic/Plenum Publishers, United States (2014).
Helmy, A., et al., "Estrogenic Effect of Soy Phytoestrogens on the Uterus of Ovariectomized Female Rats," Clinical Pharmacology & Biopharmaceutics, S2, 7 pages (2014).
Henderson, V.W., "Alzheimer"S Disease: Review of Hormone Therapy Trials and Implications for Treatment and Prevention After Menopause," The Journal of steroid biochemistry and molecular biology 142:99-106, Pergamon, England (2014).
Henriksen. Thormod, et al., "An ENDOR Sturdy of Radiation-Induced Molecular Damage to Progesterone," Journal of Magnetic Resonance 63(2):333-342, Elsevier Inc., United States (1985).
Hodis, H.N. and Mack, W.J., "Hormone Replacement Therapy and the association with Coronary Heart Disease and Overall Mortality: Clinical Application of the Timing Hypothesis," The Journal of steroid biochemistry and molecular biology 142:68-75, Pergamon, England (2014).
Hospital, M., et al., "X-Ray Crystallography of Estrogens and Their Binding to Receptor Sites," Molecular pharmacology 8(4):438-445, American Society for Pharmacology and Experimental Therapeutics, United States (1972).
Hostynek, J., et al., "Predictinga bsorptiono f fragrancec hemicalst hrough human skin," Journal of the Society of Cosmetic Chemists 46:221-229, (1995).
Hulsmann, S., et al., "Stability of Extruded 17 Beta-Estradiol Solid Dispersions," Pharmaceutical Development and Technology 6(2):223-229, Informa Healthcare, England (2001).
Hurn, P.D. and Macrae, I.M., "Estrogen as a Neuroprotectant in Stroke," Journal of Cerebral Blood Flow and Metabolism : Official Journal of the International Society of Cerebral Blood Flow and Metabolism 20(4):631-652, Nature Publishing Group, United States (2000).
Hyder, S.M., et al., "Synthetic Estrogen 17Alpha-Ethinyl Estradiol induces Pattern of Uterine Gene Expression Similar to Endogenous Estrogen 17Beta-Estradiol," The Journal of Pharmacology and Experimental Therapeutics 290(2):740-747, American Society for Pharmacology and Experimental Therapeutics, United States (1999).
Johanson, G., "Toxicity Review of Ethylene Glycol Monomethyl Ether and its Acetate Ester," Critical reviews in toxicology 30(3):307-345, Informa Healthcare, England (2000).
Johnson, S., Williams, and John, F.W. Keana, "Racemic Progesterone," Tetrahedron Letters 4(4):193-196, Pergamon Press Ltd., United Kingdom (1963).
Joshi, S.G., et al., "Detection and Synthesis of a Progestagen-Dependent Protein in Human Endometrium," Journal of Reproduction and Fertility 59(2):273-285, Portland Press, England (1980).
Kanno J., et al., "the Oecd Program to Validate the Rat Uterotrophic Bioassay to Screen Compounds for in Vivo Estrogenic Responses :

(56) References Cited

OTHER PUBLICATIONS

Phase 1," Environmental Health Perspectives 109(8):785-794,N. C. National Institute of Environmental Health Sciences., United States (2001).
Karlberg, A.T., et al., "Air Oxidation of D-Limonene (the Citrus Solvent) Creates Potent Allergens," Contact Dermatitis 26(5):332-340, Wiley, England (1992).
Karlberg, A.T., et al., "influence of an Anti-Oxidant on the formation of Allergenic Compounds During Auto-Oxidation of D-Limonene," The Annals of Occupational Hygiene 38(2):199-207, Oxford University Press, England (1994).
Kaunitz, A.M. "Extended Duration Use of Menopausal Hormone therapy," Menopause 21(6):679-681, Lippincott-Raven Publishers, United States (2014).
Khalil, S.A.H., "Stability and Dissolution Rates of Corticosteroids in Polyethylene Glycol Solid Dispersions," Drug Development and Industrial Pharmacy 10(5):771-787, Marcel Dekker, New York (1984).
Kharode, Y., et al., "the Pairing of a Selective Estrogen Receptor Modulator, Bazedoxifene, with Conjugated Estrogens as a New Paradigm for the Treatment of Menopausal Symptoms and Osteoporosis Prevention," Endocrinology 149(12):6084-6091, Endocrine Society, United States (2008).
Kim, Y.W., et al., "Safety Evaluation and Risk Assessment of D-Limonene," Journal of Toxicology and Environmental Health. Part B, Critical Reviews 16(1):17-38, Informa Healthcare, England (2013).
Kincl, F.A., et al., "Increasing Oral Bioavailability of Progesterone by formulation," Journal of steroid biochemistry 9(1):83-84, Pergamon Press, England (1978).
Knuth., et al., "Hydrogel delivery systems for vaginal and oral applications: Formulation and biological considerations, " Advanced Drug Delivery Reviews, 11(1-2):137-167, (1993) Abstract Only.
Koga, K., et al., "Enhancing Mechanism of Labrasol on intestinal Membrane Permeability of the Hydrophilic Drug Gentamicin Sulfate," European Journal of Pharmaceutics and Biopharmaceutics : Official Journal of Arbeitsgemeinschaft Fur Pharmazeutische Verfahrenstechnik E.V 64(1):82-91, Elsevier Science, Netherlands (2006).
Komm, B.S., et al., "Bazedoxifene Acetate : A Selective Estrogen Receptor Modulator with Improved Selectivity," Endocrinology 146(9):3999-4008, Endocrine Society, United States (2005).
Korkmaz, Filiz, "Biophysical Studies of Progesterone-Model Membrane Interactions," A Thesis Submitted to the Graduate School of Natural and Applied Sciences of the Middle East Technical University (2003).
Kotiyan, P.N. and Vavia, P.R., "Stability indicating Hptlc Method for the Estimation of Estradiol," Journal of pharmaceutical and biomedical analysis 22(4):667-671, Elsevier Science, England (2000).
Krzyminiewski, R., et al., "EPR Study of the Stable Radical in a y-lrradialed Single Crystal of Progesterone," Journal of Magnetic Resonance 46:300-305, Acedemic Press, England (1982).
Kubli-Garfias, C., et al., "Ab initio calculations of the electronic structure of glucocorticoids," Journal of Molecular Structure, Theochem 454(2-3):267-275, Elsevier Science B.V., Netherlands (1998).
Kubli-Garfias, Carlos, "Ab initio study of the electronic structure of progesterone and related progestins," Journal of Molecular Structure, Theochem 425(1-2):171-179, Elsevier B.V., Netherlands (1998).
Kuhnert-Brandstaetier, M., Kofler, A., "Zur Unterscheidung von losungsmittelhaltigen pseudopolymorphen Kristallformen und polymorphen Modifikationen bei Steroidhormonen.ll.," 1:127-139, Mikrochimica Acta (1968).
Kuhnert-Brandstaetier, M., Lnder, R., "Zur Hydratbildung bei Steroidhormonen," Sci. Pharm. 41(2):109-116, (1973).
Kuhnert-Brandstatier, M., "Thermo-microscopic and spectrophotometric: Determination of steroid hormones," Microchemical Journal 9:105-133, (1965).
Kumasaka, T., et al., "Effects of Various forms of Progestin on the Endometrium of the Estrogen-Primed , Ovariectomized Rat," Endocrine Journal 41(2):161-169, Japan Endocrine Society, Japan (1994).

Kuon, R.J. and Garfield, R.E., "Actions of Progestins for the inhibition of Cervical Ripening and Uterine Contractions to Prevent Preterm Birth," Facts, Views &Amp; Vision in Obgyn 4(2):110-119,Flemish Society of Obstetrics & Gynaecology, Belgium (2012).
Kuon, R.J., et al., "A Novel Optical Method to Assess Cervical Changes During Pregnancy and Use to Evaluate the Effects of Progestins on Term and Preterm Labor," American Journal of Obstetrics and Gynecology 205(1):82.e15-82.e20, Elsevier, United States (2011).
Kuon, R.J., et al., "Pharmacologic Actions of Progestins to inhibit Cervical Ripening and Prevent Delivery Depend on their Properties , the Route of Administration, and the Vehicle," American Journal of Obstetrics and Gynecology 202(5):455.e1-455.e9, Elsevier, United States (2010).
Labrie, et al., "Intravaginal prasterone (DHEA) provides local action without clinically significant changes in serum concentrations of estrogens or androgens," Journal of Steroid Biochemistry & Molecular Biology 138:359-367, Elsevier (2013).
Lacey, J.V. Jr., "The Whi Ten Year"S Later: An Epidemiologist"S View," The Journal of steroid biochemistry and molecular biology 142:12-15, Pergamon, England (2014).
Lahiani-Skiba, M., et al., "Solubility and Dissolution Rate of Progesterone-Cyclodextrin-Polymer Systems, " Drug development and industrial pharmacy 32(9):1043-1058, Informa Healthcare, England (2006).
Lancaster, R.W., et al., "The Polymorphism of Progesterone: Stabilization of a "Disappearing" Polymorph by Co-Crystallization," Journal of pharmaceutical sciences 96(12):3419-3431, Wiley-Liss, United States (2007).
Land, Laura M., "The influence of water content of triglyceride oils on the solubility of steriods," Pharmaceutical Research 22(5):Springer Science+Business Media (2005).
Lanigan, R.S. and Yamarik, T.A., "Final Report on the Safety Assessment of Bht (1)," International Journal of Toxicology 21(2):19-94, Sage Publications, United States (2002).
Lapez-Belmonte, J., et al., "Comparative Uterine Effects on Ovariectomized Rats After Repeated Treatment with Different Vaginal Estrogen formulations," Maturitas 72(4):353-358, Elsevier/North Holland Biomedical Press, Ireland (2012).
Lauer, A.C., et al., "Evaluation of the Hairless Rat as a Model for in Vivo Percutaneous Absorption," Journal of Pharmaceutical Sciences 86(1):13-18, Wiley-Liss, United States (1997).
Idder, Salima, et al., "Physicochemical properties of Progesterone," 1-26, American Chemical Society & U.S. National Library of Medicine (2014).
Leonetti, H.B., et al., "Topical Progesterone Cream Has an Antiproliferative Effect on Estrogen-Stimulated Endometrium," Fertility and sterility 79(1):221-222, Elsevier for the American Society for Reproductive Medicine, United States (2003).
Leonetti, H.B., et al., "Transdermal Progesterone Cream as an Alternative Progestin in Hormone therapy," Alternative Therapies in Health and Medicine 11(6):36-38, InnoVision Communications, United States (2005).
Lewis, J.G., et al., "Caution on the Use of Saliva Measurements to Monitor Absorption of Progesterone From Transdermal Creams in Postmenopausal Women," Maturitas 41(1):1-6, Elsevier/North Holland Biomedical Press, Ireland (2002).
Li, G.C., et al., "Solid-State Nmr Analysis of Steroidal Conformation of 17Î±- and 17Î²-Estradiol in the Absence and Presence of Lipid Environment," Steroids 77(3):185-192, Elsevier, United States (2012).
Lobo, R.A., "foreword: Hormone Therapy Arms," The Journal of steroid biochemistry and molecular biology 142:3, Pergamon, England (2014).
Lucy., et al., "Gonadotropin-releasing hormone at estrus: luteinizing hormone, estradiol, and progesterone during the periestrual and postinsemination periods in dairy cattle," Bioi Reprod 35(2):300-11, (1986) Abstract Only.
Lvova, M.SH., et al., "Thermal Analysis in the Quality Control and Standardization of Some Drugs," Journal of Thermal Analysis 40:405-411, Wiley (1993).
Madishetti, S.K., et al., "Development of Domperidone Bilayered Matrix Type Transdermal Patches : Physicochemical , in Vitro and

(56) References Cited

OTHER PUBLICATIONS

Ex Vivo Characterization," Journal of Faculty of Pharmacy 18(3):221-229, BioMed Central, England (2010).

Magness, R.R. and Ford, S.P., "Estrone, Estradiol-17 Beta and Progesterone Concentrations in Uterine Lymph and Systemic Blood Throughout the Porcine Estrous Cycle," Journal of animal science 57(2):449-455, American Society of Animal Science, United States (1983).

"Management of Symptomatic Vulvovaginal Atrophy: 2013 Position Statement of the North American Menopause Society," Menopause 20(9):888-902, Lippincott-Raven Publishers, United States (2013).

Mcguffy, Irena, "Softgel Technology as a Lipid-Based Delivery Tool for Bioavailability Enhancement," Catalent Pharma Solutions Somerset, NJ (2011).

"Merck Index, Estradiol, The Merck Index Online, Royal Society of Chemistry 2014," https://www.rsc.org/Merck-Index/monograph/mono1500003758/estradiol?q=unauthorize.

"Merck Index Online, Progesterone, Royal Society of Chemistry, accessed at https:l/www.rsc.org/Merck-lndeXI monograph/print/mono1500007889/progesterone?q=authorize, accessed on 2013 search Feb. 17, 2014,".

"Merck Index Online, Progesterone, Royal Society of Chemistry, accessed at https://www.rsc.org/Merck-lndex/monograph/print/mono1500007889/progesterone?q=authorize, accessed at 2013, search Feb. 24, 2014 ,".

Mesley, R.J., "Clathrate formation From Steroids," Chemistry & industry 37:1594-1595, John Wiley & Sons Ltd., England (1965).

"Miao, Wenbin, et al.," Chemical Properties of Progesterone American Chemical Society & U.S. National Library of Medicine (2014).

Miles, R.A., et al., "Pharmacokinetics and Endometrial Tissue Levels of Progesterone After Administration by intramuscular and Vaginal Routes : A Comparative Study," Fertility and Sterility 62(3):485-490, Elsevier for the American Society for Reproductive Medicine, United States (1994).

Miller, J.A., et al., "Safety and Feasibility of Topical Application of Limonene as a Massage Oil to the Breast," Journal Of Cancer Therapy 3(5A), Scientific Research Publishing, United States (2012).

Mueck, A.O., et al., "Genomic and Non-Genomic Actions of Progestogens in the Breast," The Journal of steroid biochemistry and molecular biology 142:62-67, Pergamon, England (2014).

Muramatsu, Mitsuo, "Thermodynamic Relationship between a- and B-Forms of Crystalline Progesterone," Journal of Pharmaceutical Sciences 68(2):175-178, American Pharmacists Association (1979).

Ng, Jo-Han., et al., "Advances in biodiesel fuel for application in compression ignition engines," Clean Technologies and Environmental Policy 12:459-493, Springer-Verlag (2010).

Nicklas, M., et al., "Preparation and Characterization of Marine Sponge Collagen Nanoparticles and Employment for the Transdermal Delivery of 17Beta-Estradiol-Hemihydrate," Drug development and industrial pharmacy 35(9):1035-1042, Informa Healthcare, England (2009).

Nilsson, U., et al., "Analysis of Contact Allergenic Compounds in Oxidized d-Limonene," Chromatographia 42:199-205, (1996).

Non Final Office Action dated Dec. 12, 2011 for U.S. Appl. No. 12/561,515, filed Sep. 17, 2009.

Non-Final Office Action dated Feb. 18, 2014 for U.S. Appl. No. 14/099,545, filed Dec. 6, 2013.

Non-Final Office Action dated Mar. 20, 2013 for U.S. Appl. No. 13/684,002, filed Nov. 21, 2012.

Notelovitz, M., et al., "initial 17Beta-Estradiol Dose for Treating Vasomotor Symptoms," Obstetrics and Gynecology 95(5):726-731, Lippincott Williams & Wilkins, United States (2000).

Notice of Allowance dated Dec. 6, 2013 for U.S. Appl. No. 13/684,002, filed Nov. 21, 2012.

Notice of Allowance dated Sep. 11, 2013 for U.S. Appl. No. 12/561,515, filed Sep. 17, 2009.

NuGen, "What is NuGen HP Hair Growth System? ," http://www.skinenergizer.com/Nugen-HP-Hair-Grow1h-System-p/ senusystem.htm, 3 pages, undated.

NuGest 900™, http://www.lhehormoneshop.nel/nugest900.htm, 4 pages, undated.

O'Leary, P., et al., "Salivary, but Not Serum or Urinary Levels of Progesterone are Elevated After Topical Application of Progesterone Cream to Pre- and Postmenopausal Women," Clinical Endocrinology 53(5):615-620,Blackwell Scientific Publications, England (2000).

"Open Notebook, Science Solubility Challenge, Solubility of progesterone in organic solvents, accessed at http:!/ lxsrv7.oru.edu/-alang/onsc/solubility/allsolvents.php?solute=progesterone, accessed on Jul. 16, 2013,".

Opinion on Diethylene glycol monoethyl ether, Scientific Committee on Consumer Products, The SCCP adopted this opinion at its 10th plenary,27 pages (2006).

Outterson, K. "the Drug Quality and Security Act—Mind the Gaps," The New England Journal of Medicine 370(2):97-99,Massachusetts Medical Society., United States (2014).

Palamakula, A., et al., "Preparation and In Vitro Characterization of Self-Nanoemulsified Drug Delivery Systems of Coenzyme Q10 Using Chiral Essential Oil Components" Pharmaceutical Technology 74-88, (2004).

Panay, N., et al., "The 2013 British Menopause Society & Women's Health Concern recommendations on hormone replacement therapy," DO1: 0.1177/1754045313489645, min.sagepub.com. Menopause International: The Integrated Journal of Post reproductive Health 0(0):1-10, (2013).

Panay, N., et al., "The 2013 British Menopause Society & Women"S Health Concern Recommendations on Hormone Replacement Therapy," Menopause international 19(2):59-68, Sage, England (2013).

Panay, N., et al., "The 2013 British Menopause Society & Women's Health Concern recommendations on hormone replacement therapy," Menopause International: The Integrated Journal of Postreproductive Health, published online May 23, 2013, Sage Publications. http://min.sagepub.com/content/early/2013/05/23/1754045313489645. 1.

Panchagnula, R. and Ritschel, W.A., "Development and Evaluation of an intracutaneous Depot formulation of Corticosteroids Using Transcutol as a Cosolvent: in-Vitro, Ex-Vivo and in-Vivo Rat Studies," The Journal of pharmacy and pharmacology 43(9):609-614, Wiley, England (1991).

Parasuraman, S., et al., "Blood Sample Collection in Small Laboratory Animals," Journal of Pharmacology & Amp; Pharmacotherapeutics 1(2):87-93, Medknow Publications and Media, India (2010).

Park, J.S., et al., "Solvent Effects on Physicochemical Behavior of Estradiols Recrystallized for Transdermal Delivery," Archives of pharmacal research 31(1):111-116, Pharmaceutical Society of Korea., Korea (South) (2008).

Park, J.S., et al., "Use of Cp/Mas Solid-State Nmr for the Characterization of Solvate Molecules within Estradiol Crystal forms," European journal of pharmaceutics and biopharmaceutics 60(3):407-412, Elsevier Science, Netherlands (2005).

Parrish, D.A. and Pinkerton, A.A., "A New Estra-1,3,5(10)-Triene-3,17Beta-Diol Solvate: Estradiol-Methanol-Water (3/2/1)," Acta crystallographica. Section C, Crystal structure communications 59(Pt2):o80-82, Wiley-Blackwell, United States (2003).

Patel., et al., "Transdermal Drug Delivery System: A Review," The Pharma Innovation, The Pharma Journal 1(4), (2012).

Payne, R.S., et al., "Examples of Successful Crystal Structure Prediction: Polymorphs of Primidone and Progesterone," International Journal of Pharmaceutics 177(2):231-245, Elsevier/North-Holland Biomedical Press., Netherlands (1999).

PCCA, Apothogram, PCCA, Houston, TX, (2014).

Persson, Linda C, et al., "Physicochemical Properties of Progesterone Selecte," 1-5, American Chemical Society & U.S. National Library of Medicine (2014).

Pfaus, J.G., et al., "Selective Facilitation of Sexual Solicitation in the Female Rat by a Melanocortin Receptor Agonist," Proceedings of the National Academy of Sciences of the United States of America 101(27):10201-10204, National Academy of Sciences, United States (2004).

Pheasant, Richard, , "Polymorphism of 17-Ethinylestradiol," Schering Corporation, Bloomfield, NJ (1950).

(56) References Cited

OTHER PUBLICATIONS

Pickles, V.R. "Cutaneous Reactions to injection of Progesterone Solutions into the Skin," British Medical Journal 2(4780):373-374, British Medical Association, England (1952).

Pinkerton, J.V. and Thomas, S., "Use of Serms for Treatment in Postmenopausal Women," The Journal of Steroid Biochemistry and Molecular Biology 142:142-154, Pergamon, England (2014).

Pinkerton, J.V. "What are the Concerns About Custom-Compounded "Bioidentical" Hormone therapy?," Menopause 21(12):1298-1300, Lippincott-Raven Publishers, United States (2014).

Pisegna, Gisia L, "A High-pressure Vibrational Spectroscopic Study of Polymorphism in Steroids," Thesis, McGill University, Dept. of Chem:National Library of Canada (1999).

Prajapati, Hetal N., et al., "A comparative Evaluation of Mono-, Di- and Triglyceride of Medium Chain Fatty Acids by Lipid/Surfactan UWater," Springerlink.com, pp. 1-21, (2011).

Prausnitz, M.R. and Langer, R., "Transdermal Drug Delivery," Nature Biotechnology 26(11):1261-1268, Nature America Publishing, United States (2008).

Price, S.L., "The Computational Prediction of Pharmaceutical Crystal Structures and Polymorphism," Advanced drug delivery reviews 56(3):301-319, Elsevier Science Publishers, B.V., Netherlands (2004).

Product Safety Assessment, Diethylene Glycol Monoethyl Ether, The Dow Chemical Company Page, 5 Pages (2007).

Progynova TS 100, available online at file:I//C:!Users/Caii%20Family/Desktop/Progynova%20TS%20100%2012%20Patches_Pack%20%28Estradioi%20Hemihydrate%29.html, 2010.

Provider Data Sheet, "About Dried Blood Spot Testing," ZRT Laboratory, 3 pages (2014).

Rahn, D.D., et al., "Vaginal Estrogen for Genitourinary Syndrome of Menopause: A Systematic Review," Obstetrics and Gynecology 124(6):1147-1156, Lippincott Williams & Wilkins, United States (2014).

Reisman, S.A., et al., "Topical Application of the Synthetic Triterpenoid Rta 408 Protects Mice From Radiation-induced Dermatitis," Radiation Research 181(5):512-520, Radiation Research Society, United States (2014).

Restriction/Election Requirement dated Mar. 5, 2014 for U.S. Appl. No. 14/099,623, filed Dec. 6, 2013.

Restriction/Election Requirement dated Feb. 20, 2014 for U.S. Appl. No. 14/099,562, filed Dec. 6, 2013.

Rosilio, V., et al., "Physical Aging of Progesterone-Loaded Poly(D,L,-Lactide-Co-Glycolide) Microspheres," Pharmaceutical research 15(5):794-798, Kluwer Academic/Plenum Publishers, United States (1998).

Ross, D., et al., "Randomized, Double-Blind, Dose-Ranging Study of the Endometrial Effects of a Vaginal Progesterone Gel in Estrogen-Treated Postmenopausal Women," American Journal of Obstetrics and Gynecology 177(4):937-941, Elsevier, United States (1997).

Ruan, X. and Mueck, A.O., "Systemic Progesterone therapy—Oral, Vaginal, injections and Even Transdermal ?," Maturitas 79(3):248-255, Elsevier/North Holland Biomedical Press, Ireland (2014).

Salem, H.F. "Sustained-Release Progesterone Nanosuspension Following intramuscular injection in Ovariectomized Rats," International Journal of Nanomedicine 10:943-954,Dove Medical Press, New Zealand (2010).

Salole, E.G., "The Physicochemical Properties of Oestradiol," Journal of Pharmaceutical and Biomedical Analysis 5(7):635-648, Elsevier Science, England (1987).

Salole, Eugene G., "Estradiol, Analy lical Profiles of Drug Substances," vol. 15, pp. 283-318, (1986).

Santen, R.J., "Menopausal Hormone Therapy and Breast Cancer," The Journal of Steroid Biochemistry and Molecular Biology 142:52-61, Pergamon, England (2014).

Santen, R.J. "Vaginal Administration of Estradiol : Effects of Dose, Preparation and Timing on Plasma Estradiol Levels," The Journal of the International Menopause Society :1-14, Informa Healthcare, England (2014).

Sarkar, Basu, et al., "Chemical Stability of Progesterone in Compounded Topical Preparations using PLO Transdermal CreamTM and HRT CreamTM Base," Steroids and Hormonal Science 4:2, (2013).

Sarrel. and Philip., "The Mortality Toll of Estrogen Avoidance: An Analysis of Excess Deaths Among Hysterectomied Women Aged 50 to 59 Years," American Journal of Public Health, Research and Practice, pp. e1-e6, Published online ahead of print Jul. 18, 2013.

Satyanarayana, D, et al., "Aqueous Solubility Predictions of Aliphatic Alcohols, Alkyl Substituted Benzoates and Steroids," Asian Journal of Chemistry 9(3): 418-26, (1997).

Scavarelli, Rosa Maria, et al., Progesterone and Hydrate or Solvate, SciFinder, pp. 1-2, American Chemical Society (2014).

Schindler, A.E., "The "Newer" Progestogens and Postmenopausal Hormone Therapy (Hrt)," The Journal of Steroid Biochemistry and Molecular Biology 142:48-51, Pergamon, England (2014).

Schutte, S.C. and Taylor, R.N., "A Tissue-Engineered Human Endometrial Stroma That Responds to Cues for Secretory Differentiation, Decidualization, and Menstruation," Fertility and Sterility 97(4):997-1003, Elsevier for the American Society for Reproductive Medicine, United States (2012).

Schweikart, K.M., et al., "Comparative Uterotrophic Effects of Endoxifen and Tamoxifen in Ovariectomized Sprague-Dawley Rats," Toxicologic Pathology 42(8):1188-1196, Sage Publications, United States (2014).

SciFinder Scholar Prednisone Chemical Properties, SciFinde, pp. 1-7, National Library of Medicine (2014).

SciFinder Scholar Prednisone Physical Properties, SciFinder, pp. 1-10, Natioinal Library of Medicine (2014).

SciFinder Scholar Progesterone Experimental Properties, SciFinder, pp. 1-9, American Chemical Society (2014).

Serantoni, Foresti, et al., "4-Pregnen-3, 20-Dione (progesterone, form II)," Crystal Structure Communications 4(1):189-92, CAPLUS Database (1975).

Shao, R., et al., "Direct Effects of Metformin in the Endometrium : A Hypothetical Mechanism for the Treatment of Women with Pcos and Endometrial Carcinoma," Journal of Experimental & Clinical Cancer Research 33:41, BioMed Central, England (2014).

Sharma, H.C., et al., "Physical Properties of Progesterone Selected Refer, SciFinder," pp. 1-5, American Chemical Society & U.S. National Library of Medicine (2014).

Shrier, L.A., et al., "Mucosal Immunity of the Adolescent Female Genital Tract," The Journal of Adolescent Health 32(3):183-186, Elsevier, United States (2003).

Shufelt, C.L., et al., "Hormone Therapy Dose, formulation, Route of Delivery, and Risk of Cardiovascular Events in Women : Findings From the Women"S Health initiative Observational Study," Menopause 21(3):260-266, Lippincott-Raven Publishers, United States (2014).

Siew, A, et al.,"Bioavailability Enhancement with Lipid-Based Durg-Delivery Systems" Phamraceutlcal Technology 28,30-31, (2014).

Sigma-Aldrich, Progesterone-Water Soluble: powder, BioReagent, suitable for cell culture), MSDS available online: http://www.sigmaaldrich.com/catalog/producl/sigma/p7556.

Simon, J., et al., "Effective Treatment of Vaginal Atrophy with an Ultra-Low-Dose Estradiol Vaginal Tablet," Obstetrics and gynecology 112(5):1053-1060, Lippincott Williams & Wilkins, United States (2008).

Simon, J.A. "What If the Women'S Health initiative Had Used Transdermal Estradiol and Oral Progesterone instead?," Menopause 21(7):769-783, Lippincott-Raven Publishers, United States (2014).

Sitruk-Ware. and Regine., "Oral Micronized Progesterone—Bioavailability Pharmacokinetics, Pharmacological and Therapeutic Implications—A Review," Contraception 36(4):373-402, (1987).

Sitruk-Ware, R., "Progestogens in Hormonal Replacement Therapy: New Molecules, Risks, and Benefits," Menopause 9(1):6-15, Lippincott-Raven Publishers, United States (2002).

Smith and Nicholas., "Lower Risk of Cardiovascular Events in Postmenopausal Women Taking Oral Estradiol Compared with Oral Conjugated Equine Estrogens," JAMA Intern Med, pp. e1-e7, published online Sep. 30, 2013.

(56) References Cited

OTHER PUBLICATIONS

Smyth, H.F., et al., "A 2-Yr Study of Diethylene Glycol Monoethyl Ether in Rats," Food and Cosmetics Toxicology 2:641-642, Pergamon Press, England (1964).

Stanczyk, F.Z. and Bhavnani, B.R., "Current Views of Hormone Therapy for the Management and Treatment of Postmenopausal Women," The Journal of steroid biochemistry and molecular biology 142:1-2, Pergamon, England (2014).

Stanczyk, F.Z. and Bhavnani, B.R., "Use of Medroxyprogesterone Acetate for Hormone Therapy in Postmenopausal Women: Is It Safe?," The Journal of steroid biochemistry and molecular biology 142:30-38, Pergamon, England (2014).

Stanczyk, F.Z., et al., "Ethinyl Estradiol and $17\beta$-Estradiol in Combined Oral Contraceptives: Pharmacokinetics, Pharmacodynamics and Risk assessment," Contraception 87(6):706-727, Elsevier, United States (2013).

Stanczyk, F.Z., et al., "therapeutically Equivalent Pharmacokinetic Profile Across Three Application Sites for Ag200-15 , A Novel Low-Estrogen Dose Contraceptive Patch," Contraception 87(6):744-749, Elsevier, United States (2013).

Stein, Emily A., et al., "Progesterone, SciFinder Scholar Search" 1-46, American Chemical Society & U.S. National Library of Medicine, Feb. 24, 2014.

Stein, Emily A., et al., "Progesterone Physical Properties," 1-46, American Chemical Society & U.S. National Library of Medicine, Feb. 24, 2014.

Stein, Emily A., et al., "Progesterone Physical Properties," 1-46, American Chemical Society & U.S. National Library of Medicine, Mar. 3, 2014.

Strickley, R.G., "Solubilizing Excipients in Oral and injectable formulations," Pharmaceutical research 21(2):201-230, Kluwer Academic/Plenum Publishers, United States (2004).

Strocchi, Antonino, Fatty Acid Composition, and Triglyceride Structure of Corn Oil, Hydrogenated Corn Oil, and Corn Oil Margarine, Journal of Food Science 47, pp. 36-39, (1981).

Struhar, M., et al., "Preparation of the Estradiol Benzoate injection Suspension," Ceskoslovenska farmacie 27(6):245-249, Ceskoslovenska Lekarska Spolecnost, Czech Republic (1978).

Sullivan, D.W.Jr., et al., "A review of the nonclinical safety of Transcutol®, a highly purified form of diethylene glycol monoethyl ether (DEGEE) used as a pharmaceutical excipient," Food and Chemical Toxicology 72:40-50, Elsevier Science Ltd, England (2014).

Sun, J. "D-Limonene : Safety and Clinical Applications," Alternative Medicine Review 12(3):259-264, Alternative Medicine Review, United States (2007).

Tahition Noni. "Body Balance Cream," http://products.lni.com/dominican_republic/sa_spanish/nonistore/ producl/3438/3416/, 1 page, undated.

Tait, A.D., "Characterization of the Products From the Oxidation of Progesterone with Osmium Tetroxide," Steroids 20(5):531-542, Elsevier, United States (1972).

Takacs, M., et al., "The Light Sensitivity of Corticosteroids in Crystalline form Photochemical Studies 59 (1)," Pharmaceutica acta Helvetiae 66(5-6):137-140, Schweizerische Apotheker-Verein, Switzerland (1991).

Tan, Melvin, S., et al., "A Sensitive Method for the Determination of Progesterone in Human Plasma by LC-MS-MS, M1025," Cedra Corporation, Austin.

Tang, F.Y., et al., "Effect of Estrogen and Progesterone on the Development of Endometrial Hyperplasia in the Fischer Rat," Biology of Reproduction 31(2):399-413, Society for the Study of Reproduction, United States (1984).

Tas, M., et al., "Comparison of Antiproliferative Effects of Metformine and Progesterone on Estrogen-induced Endometrial Hyperplasia in Rats," Gynecological Endocrinology 29(4):311-314, Informa Healthcare, England (2013).

Tella, S.H., Gallagher, J.C., "Prevention and treatment of postmenopausal osteoporosis," The Journal of Steroid Biochemistry and Molecular Biology 142:155-170, Elsevier Ltd., United Kingdom (2014).

Thomas, J., et al., "The Effect of Water Solubility of Solutes on Their Flux Through Human Skin in Vitro: An Extended Flynn Database Fitted to the Roberts-Sloan Equation," International Journal of Pharmaceutics 339(1-2):157-167, Elsevier/North-Holland Biomedical Press., Netherlands (2007).

Thomas, P. "Characteristics of Membrane Progestin Receptor Alpha (Mpralpha) and Progesterone Membrane Receptor Component 1 (Pgmrc1) and their Roles in Mediating Rapid Progestin Actions," Frontiers in Neuroendocrinology 29(2):292-312, Academic Press, United States (2008).

Tripathi, R., et al., "Study of Polymorphs of Progesterone by Novel Melt Sonocrystallization Technique: A Technical Note," AAPS PharmSciTech 11(3):1493-1498, Elsevier/North-Holland Biomedical Press., Netherlands (2010).

Trommer, H. and Neubert, R.H., "Overcoming the Stratum Corneum : the Modulation of Skin Penetration a Review," Skin Pharmacology and Physiology 19(2):106-121, Karger, Switzerland (2006).

Tuleu, C., et al., "Comparative Bioavailability Study in Dogs of a Self-Emulsifying formulation of Progesterone Presented in a Pellet and Liquid form Compared with an Aqueous Suspension of Progesterone," Journal of Pharmaceutical Sciences 93(6):1495-1502, Wiley-Liss, United States (2004).

Ueda, T., et al., "Topical and Transdermal Drug Products," Pharmacopeial Forum 35(3):750-764, (2009).

USP, 401 Fats and Fixed Oils, Chemical Tests, Second Suplemento USP36-NF 31, pp. 6141-6151, (2013).

USP, Lauroyl Polyoxylglycerides, Saftey Data Sheet, US, 5611 Version #02, pp. 1-9, (2013).

"USP Monographs: Progesterone. USP29, accessed at www.pharmacopeia.cn/v29240/usp29nf24sO_m69870.html, accessed on Feb. 25, 2014,".

USP, Official Monographs, Corn Oil, NF 31, pp. 1970-1971, (2013).

USP. Official Monographs, Lauroyl Polyoxylglycerides, NF 31, pp. 2064-2066, (2013).

USP, Official Monographs, Medium Chain Triglycerides, NF 31, pp. 2271-2272, (2013).

USP, Official Monographs, Mono- and Di-glycerides, NF 31, pp. 2101, (2013).

USP, USP Certificate—Corn Oil, Lot GOL404, Jul. 2013.

Utian, W.H., et al., "Relief of Vasomotor Symptoms and Vaginal Atrophy with Lower Doses of Conjugated Equine Estrogens and Medroxyprogesterone Acetate," Fertility and sterility 75(6):1065-1079, Elsevier for the American Society for Reproductive Medicine, United States (2001).

Voegtline, K.M. and Granger, D.A., "Dispatches From the interface of Salivary Bioscience and Neonatal Research," Frontiers in Endocrinology 5:25,Frontiers Research Foundation, Switzerland (2014).

Waddell, B.J. and Bruce, N.W., "the Metabolic Clearance of Progesterone in the Pregnant Rat : Absence of a Physiological Role for the Lung," Biology of Reproduction 40(6):1188-1193, Society for the Study of Reproduction, United States (1989).

Waddell, B.J. and Oleary, P.C., "Distribution and Metabolism of Topically Applied Progesterone in a Rat Model," The Journal of Steroid Biochemistry and Molecular Biology 80(4-5):449-455, Pergamon, England (2002).

Walter, L.M., et al., "the Role of Progesterone in Endometrial Angiogenesis in Pregnant and Ovariectomised Mice," Reproduction 129(6):765-777,Reproduction and Fertility by BioScientifica, England (2005).

Warney Cole and Percy L., Julian , "A Study of the 22-Ketosteroids," Journal of the American Chemical Society 67(8):1369-1375, (1945).

Weber, E.J. "Corn Lipids," Cereal Chemistry Journal 55(5): 572-584, American Association of Cereal Chemists (1978).

Weber, M.T., et al., "Cognition and Mood in Perimenopause: A Systematic Review and Meta-Analysis," The Journal of Steroid Biochemistry and Molecular Biology 142:90-98, Pergamon, England (2014).

(56) References Cited

OTHER PUBLICATIONS

Whitehead, M.I., et al., "Absorption and Metabolism of Oral Progesterone," British medical journal 280(6217):825-827, British Medical Association, England (1980).
William, L., Duax, Jane F., Griffin, Douglas, C., Rohrer, "Conformation of Progesterone Side Chain: Conftict between X-ray Data and Force-Field Calculations," Journal of the American Chemical Society 103(22):6705-6712, (1981).
Wiranidchapong, Chutima et al., "Method of preparation does not affect the miscibility between steroid hormone and polymethacrylate," Thermochimica Acta 485(1-2):57-64, Elsevier B.V., Netherlands (2009).
Wood, C.E., et al., "Effects of estradiol with micronized progesterone or medroxyprogesterone acetate on risk markers for breast cancer in postmenopausal monkeys," Breast Cancer Research and Treatment 101:125-134, Springer Science+ Business Media B.V (2006), published online Jul. 14, 2006.
Wren, B.G., et al., "Effect of Sequential Transdermal Progesterone Cream on Endometrium , Bleeding Pattern , and Plasma Progesterone and Salivary Progesterone Levels in Postmenopausal Women," The Journal of the International Menopause Society 3(3):155-160, Informa Healthcare, England (2000).
Wu, X., et al., "Gene Expression Profiling of the Effects of Castration and Estrogen Treatment in the Rat Uterus," Biology of Reproduction 69(4):1308-1317, Society for the Study of Reproduction, United States (2003).
Yalkowsky, Samuel, H. , "Handbook of Acqueous Solubility Data," 1110-1111, CRC Press, United States.
Yalkowsky, S.H. and Valvani, S.C., "Solubility and Partitioning I: Solubility of Nonelectrolytes in Water," Journal of Pharmaceutical Sciences 69(8):912-922, Wiley-Liss, United States (1980).
Yue, W., et al., "Genotoxic Metabolites of Estradiol in Breast: Potential Mechanism of Estradiol induced Carcinogenesis," The Journal of Steroid Biochemistry and Molecular Biology 86(3-5):477-486, Pergamon, England (2003).
Zava, D. "Topical Progesterone Delivery and Levels in Serum, Saliva, Capillary Blood, and Tissues" Script:4-5.
Zava, D.T., et al., "Percutaneous absorption of progesterone," Maturitas 77:91-92, Elsevier/North Holland Biomedical Press, Ireland (2014).
Geelen, M.J.H., et al., "Dietary Medium-Chain Fatty Acids Raise and (n-3) Polyunsaturated Fatty Acids Lower Hepatic Triacylglycerol Synthesis in Rats," The Journal of Nutrition 125:2449-2456, American Institute of Nutrition, United States (1995).
Herman, A and Herman, A.P., "Essential oils and their constituents as skin penetration enhancer for transdermal drug delivery: a review," Journal of Pharmacy and Pharmacology 67(4):473-485, Royal Pharmaceutical Society, England (2014).
Manson, J.E., et al., "Menopausal Hormone Therapy and Health Outcomes During the Intervention and Extended Poststopping Phases of the Women's Health Initiative Randomized Trials," The Journal of the American Medical Association 310:1353-1368, American Medical Association, United States (2013).
Notice of Allowance, dated Dec. 10, 2014, in U.S. Appl. No. 14/099,562, Bernick, B.A., filed Dec. 6, 2013, 10 pages.
Notice of Allowance, dated Dec. 10, 2014, in U.S. Appl. No. 14/099,598, Bernick, B.A., filed Dec. 6, 2013, 8 pages.
Notice of Allowance, dated Dec. 15, 2014, in U.S. Appl. No. 14/099,623, Bernick, B.A., filed Dec. 6, 2013, 9 pages.
Notice of Allowance, dated Feb. 11, 2015, in U.S. Appl. No. 14/475,864, Bernick, B.A., filed Sep. 3, 2014, 9 pages.
Notice of Allowance, dated Feb. 13, 2015, in U.S. Appl. No. 14/475,814, Bernick, B.A., filed Sep. 3, 2014, 6 pages.
Notice of Allowance, dated Jan. 22, 2015, in U.S. Appl. No. 14/099,582, Bernick, B.A., filed Dec. 6, 2013, 5 pages.
Notice of Allowance, dated Jul. 14, 2014, in U.S. Appl. No. 14/099,545, Bernick, B.A., filed Dec. 6, 2013, 9 pages.
Notice of Allowance, dated Jul. 15, 2014, in U.S. Appl. No. 14/099,571, Bernick, B.A., filed Dec. 6, 2013, 11 pages.
Notice of Allowance, dated Nov. 26, 2014, in U.S. Appl. No. 14/099,612, Bernick, B.A., filed Dec. 6, 2013, 12 pages.
Notice of Allowance, dated Nov. 7, 2014, in U.S. Appl. No. 14/099,582, filed Dec. 6, 2013, 14 pages.
Office Action, dated Apr. 14, 2015, in U.S. Appl. No. 14/125,554, Bernick, B.A., filed Dec. 12, 2013, 9 pages.
Office Action, dated Apr. 7, 2015, in U.S. Appl. No. 14/624,051, Bernick B.A., filed Feb. 17, 2015, 10 pages.
Office Action, dated Dec. 8, 2014, in U.S. Appl. No. 14/106,655, Bernick, B.A., filed Dec. 13, 2013, 9 pages.
Office Action, dated Feb. 18, 2015, in U.S. Appl. No. 14/521,230, Bernick, B.A., filed Oct. 22, 2014, 8 pages.
Office Action, dated Jul. 18, 2014, in U.S. Appl. No. 14/099,623, Bernick, B.A., filed Dec. 6, 2013, 12 pages.
Office Action, dated Jul. 2, 2014, in U.S. Appl. No. 14/099,562, Bernick, B.A., filed Dec. 6, 2013, 9 pages.
Office Action, dated Jul. 3, 2014, in U.S. Appl. No. 14/099,598, Bernick, B.A., filed Dec. 6, 2013, 16 pages.
Office Action, dated Jul. 30, 2014, in U.S. Appl. No. 14/099,612, Bernick, B.A., filed Dec. 6, 2013, 12 pages.
Office Action, dated Jun. 17, 2014, in U.S. Appl. No. 14/099,582, Bernick, B.A., filed Dec. 6, 2013, 14 pages.
Office Action, dated Mar. 12, 2015, in U.S. Appl. No. 14/136,048, Bernick, B.A., filed Dec. 20, 2013, 24 pages.
Office Action, dated Mar. 27, 2014, in U.S. Appl. No. 14/099,562, Bernick, B.A., filed Dec. 6, 2013, 8 pages.
Office Action, dated Oct. 1, 2014, in U.S. Appl. No. 14/475,814, Bernick, B.A., filed Sep. 3, 2014, 6 pages.
Office Action, dated Oct. 2, 2014, in U.S. Appl. No. 14/475,864, Bernick, B.A., filed Sep. 3, 2014, 6 pages.
Portman, D., et al., "One-year treatment persistence with local estrogen therapy in postmenopausal women diagnosed as having vaginal atrophy," Menopause 22(11): 7 pages, The North American Menopause Society, United States (2015).
Rao, R. and Rao, S., "Intra Subject Variability of Progesterone 200 mg Soft Capsules in Indian Healthy Adult Postmenopausal Female Subjects under Fasting Conditions," Journal of Bioequivalence & Bioavailability 6(4):139-143, Open Access (2014).
Restriction Requirement, dated Apr. 14, 2015, in U.S. Appl. No. 13/843,428, Bernick, B.A., filed Mar. 15, 2013, 7 pages.
Restriction Requirement, dated Apr. 29, 2014, in U.S. Appl. No. 14/099,582, Bernick, B.A., filed Dec. 6, 2013, 9 pages.
Restriction Requirement, dated Dec. 5, 2014, in U.S. Appl. No. 14/125,554, Bernick, B.A., filed Dec. 12, 2013, 7 pages.
Restriction Requirement, dated Dec. 5, 2014, in U.S. Appl. No. 14/521,230, Bernick, B.A., filed Oct. 22, 2014, 9 pages.
Restriction Requirement, dated Jul. 3, 2014, in U.S. Appl. No. 14/106,655, Bernick, B.A., filed Dec. 13, 2013, 6 pages.
Restriction Requirement, dated Mar. 16, 2015, in U.S. Appl. No. 13/843,362, Bernick, B.A., filed Mar. 15, 2013, 7 pages.
Restriction Requirement, dated Mar. 20, 2014, in U.S. Appl. No. 14/099,612, Bernick, B.A., filed Dec. 6, 2013, 9 pages.
Restriction Requirement, dated Mar. 26, 2015, in U.S. Appl. No. 14/476,040, Bernick, B.A., filed Sep. 3, 2014, 7 pages.
Restriction Requirement, dated Mar. 28, 2014, in U.S. Appl. No. 14/099,571, Bernick, B.A., filed Dec. 6, 2013, 7 pages.
International Search Report and Written Opinion of International Application No. PCT/US2015/023041, Korean Intellectual Property Office, Republic of Korea, dated Jun. 30, 2015, 14 pages.
Sarpal, K., et al., "Self-Emulsifying Drug Delivery Systems: A Strategy to Improve Oral Bioavailability," Current Research & Information on Pharmaceuticals Sciences 11(3):42-49, NIPER, India (Jul.-Sep. 2010).

* cited by examiner

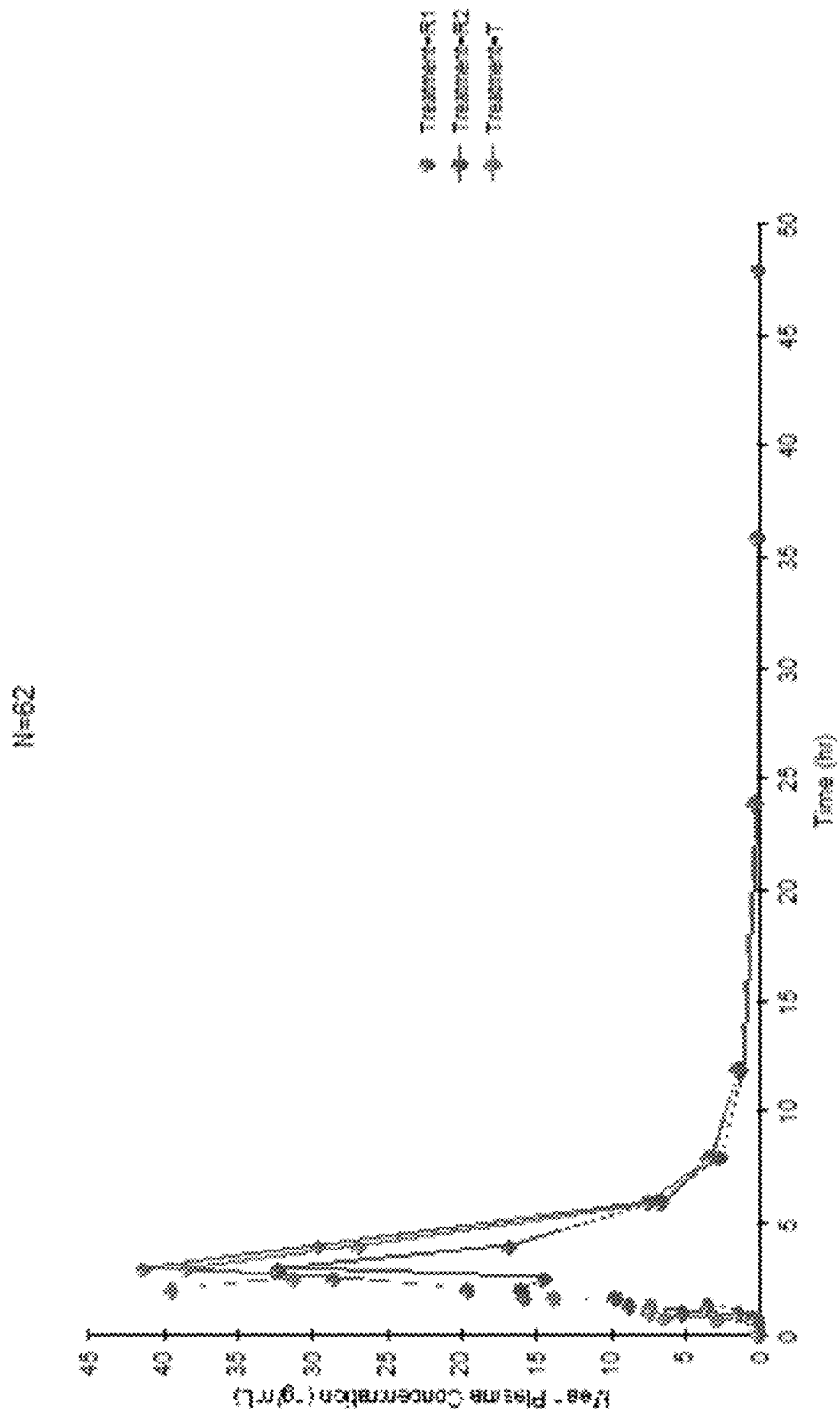
Fig. 7: Linear Plot of Mean Plasma Progesterone (Corrected) Concentrations Versus Time (N=62)

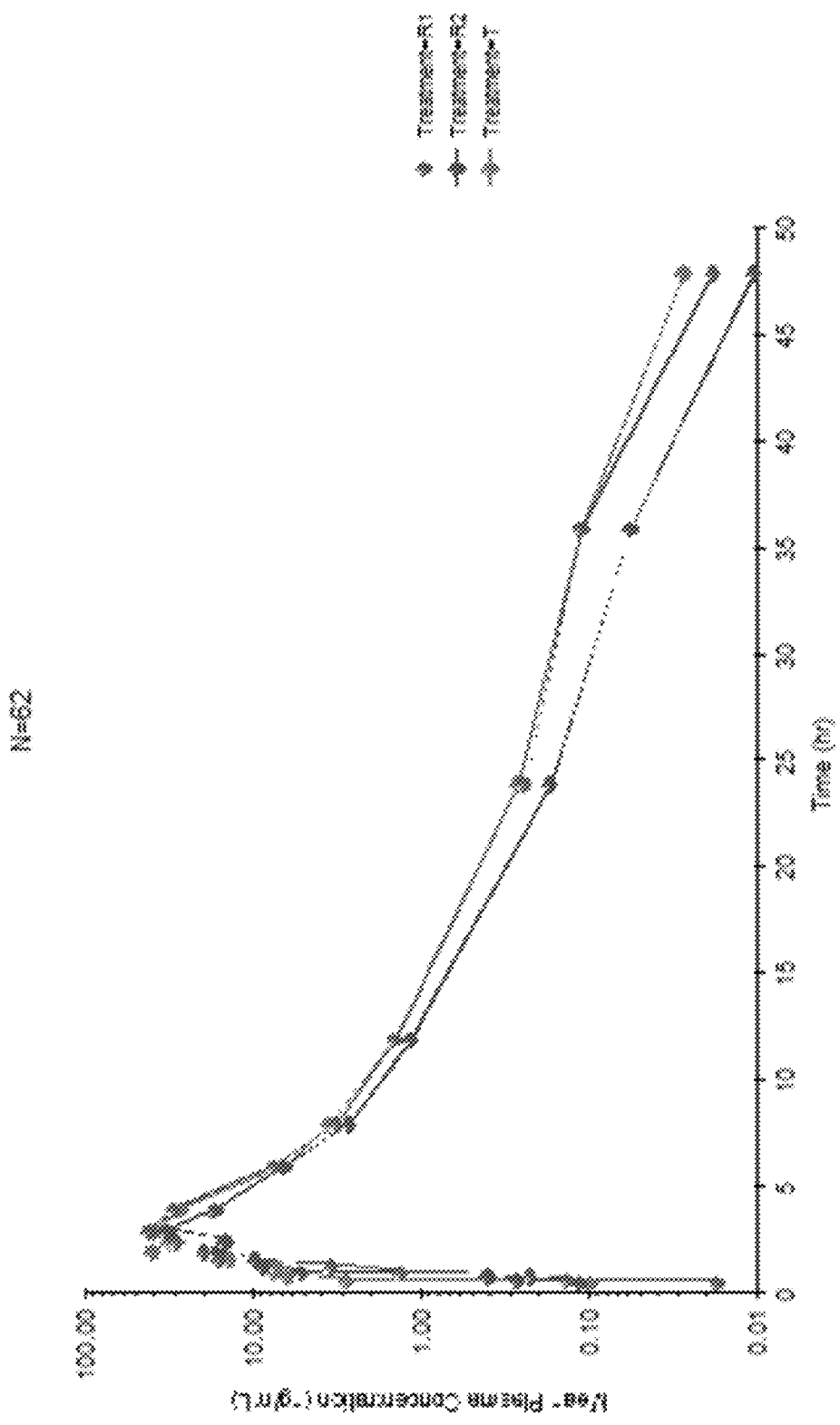
Fig. 8— Semi-logarithmic Plot of Mean Plasma Progesterone (Corrected) Concentrations Versus Time (N=62)

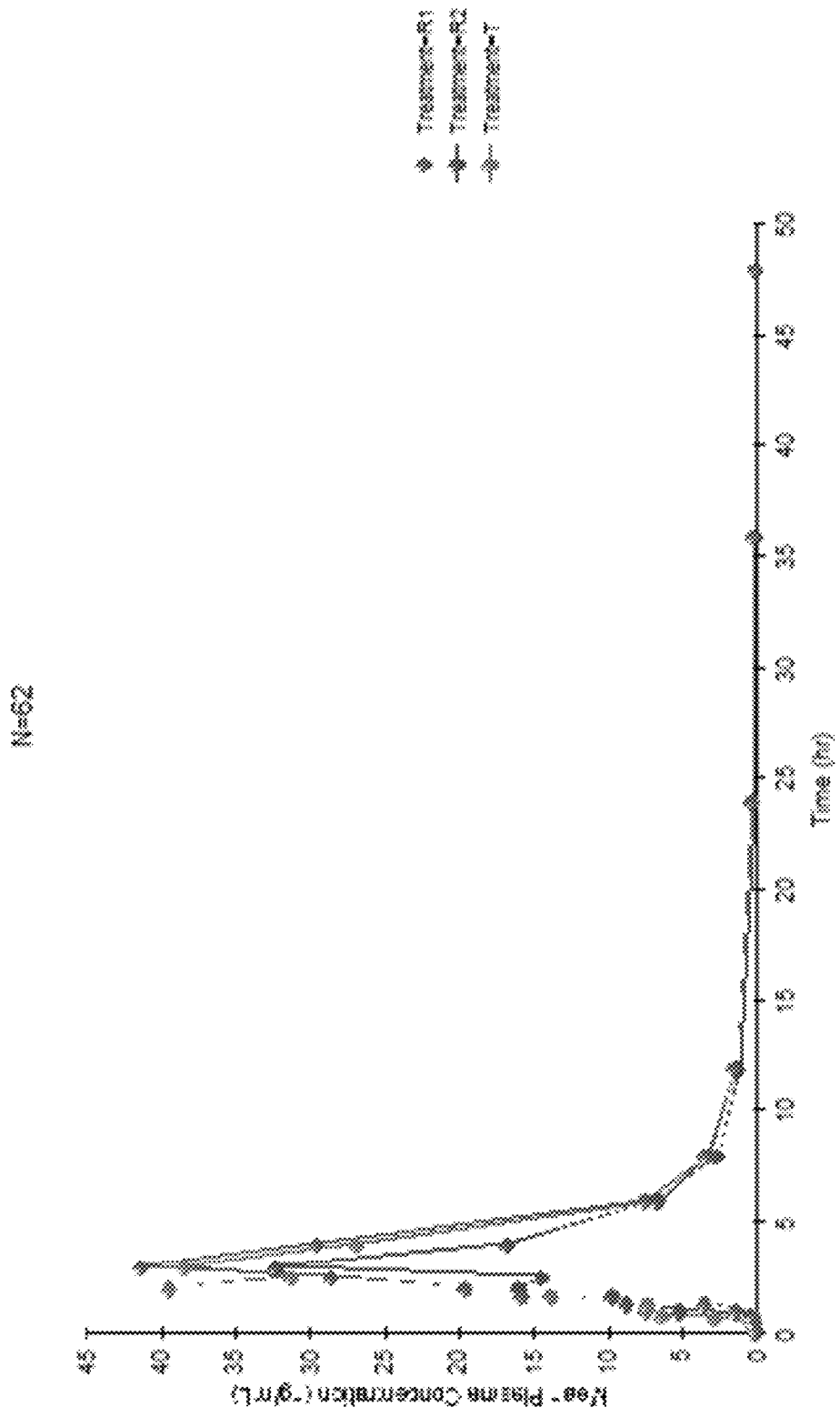
Fig. 9 — Linear Plot of Mean Plasma Progesterone (Uncorrected) Concentrations Versus Time (N=62)

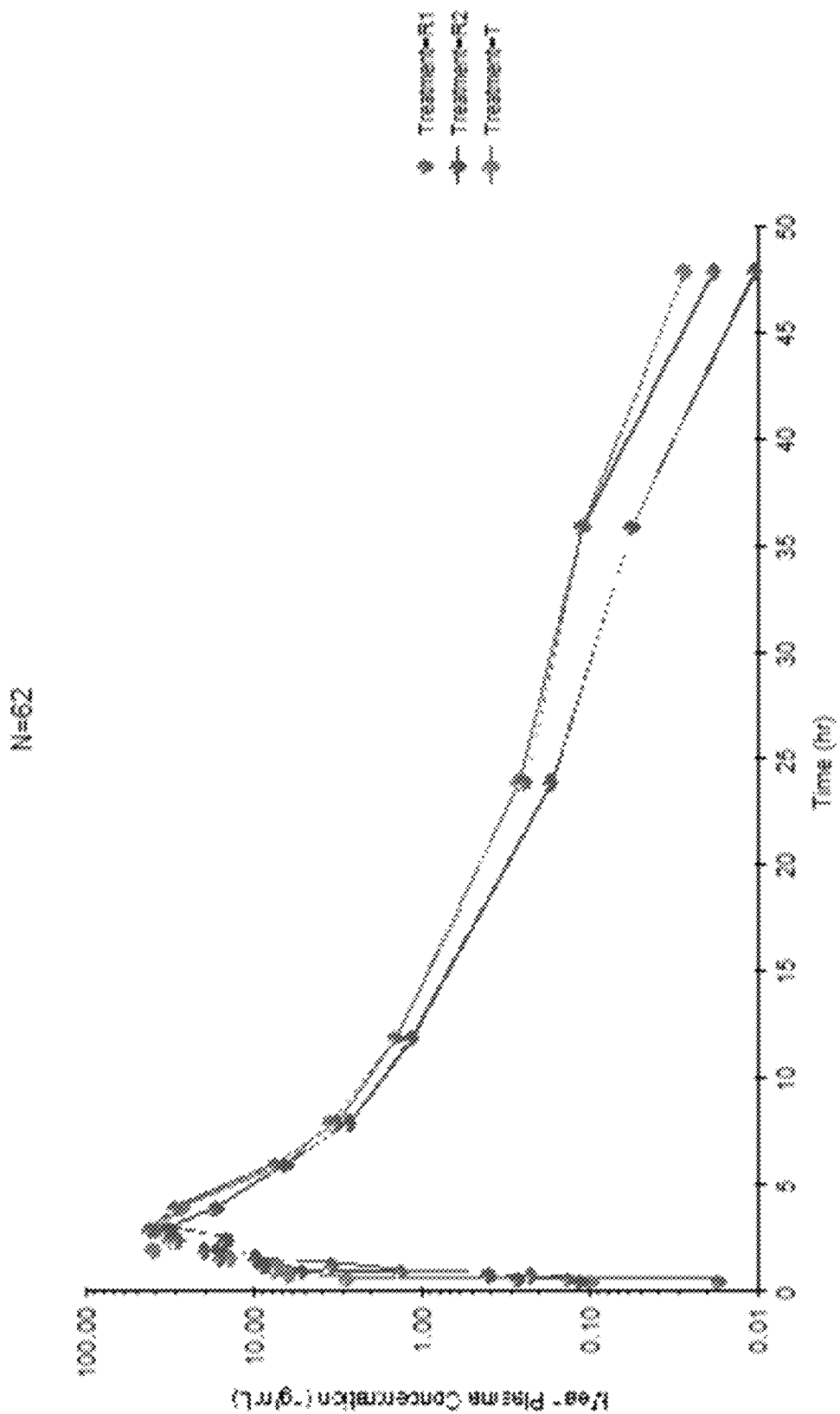
Fig. 10—Semi-logarithmic Plot of Mean Plasma Progesterone (Uncorrected) Concentrations Versus Time (N=62)

PROGESTERONE FORMULATIONS HAVING A DESIRABLE PK PROFILE

CROSS-REFERENCE TO RELATED APPLICATIONS

This application claims priority to U.S. Provisional Application 61/972,068 filed 28 Mar. 2014 and is a continuation in part of U.S. Ser. No. 14/125,547 filed 11 Dec. 2013 which is a National Stage application under 35 U.S.C. § 371 of International Application Serial No. PCT/US2013/046442, entitled "PROGESTERONE FORMULATIONS" which was filed on 18 Jun. 2013, and claims priority to the following U.S. Patent Applications: U.S. Provisional Application Ser. No. 61/661,302, entitled "ESTRADIOL FORMULATIONS," which was filed on Jun. 18, 2012; U.S. Provisional Application Ser. No. 61/662,265, entitled "PROGESTERONE FORMULATIONS," which was filed on Jun. 20, 2012; U.S. patent application Ser. No. 13/684,002, entitled "NATURAL COMBINATION HORMONE REPLACEMENT FORMULATIONS AND THERAPIES," which was filed Nov. 21, 2012; U.S. Patent Application Serial No. PCT/US2013/023309, entitled "TRANSDERMAL HORMONE REPLACEMENT THERAPIES," which was filed Jan. 25, 2013; and U.S. patent application Ser. No. 13/843,362, entitled "TRANSDERMAL HORMONE REPLACEMENT THERAPIES," which was filed Mar. 15, 2013. This application also claims priority to U.S. patent application Ser. No. 13/843,428, entitled "NATURAL COMBINATION HORMONE REPLACEMENT FORMULATIONS AND THERAPIES," which was filed Mar. 15, 2013. Each of the aforementioned applications are incorporated herein by reference in their entirety.

FIELD OF INVENTION

This disclosure relates to progesterone formulations, methods of using these formulations, and their related pharmacokinetic parameters. Various progesterone formulations may be used in hormone therapies for menopausal, peri-menopausal and post-menopausal females, for example, to mitigate side effects from estrogen replacement therapy. In addition, various progesterone formulations may be used to prevent preterm delivery in pregnant women having a shortened cervix. Progesterone can likewise be used to treat endometrial hyperplasia and amenorrhea.

BACKGROUND OF THE INVENTION

It is not uncommon for pre-menopausal, peri-menopausal, menopausal, or postmenopausal females, to experience vaginal dryness, vaginal odor, vulvar irritation and itching, dysuria (pain, burning or stinging when urinating), dysparuenia (vaginal pain associated with sexual activity), or vaginal bleeding associated with sexual activity. They may also experience night sweats and menopausal hot flashes (vasomotor symptoms), soreness, increased or variant urinary frequency and urgency, urinary discomfort and incontinence ("estrogen-deficient urinary state(s)"), mood disturbances, and symptoms related vulvo-vaginal atrophy, endometrial hyperplasia, endometrial cancer, and other symptoms of estrogen-related disorders. These symptoms, and other symptoms known to those skilled in the art, are believed to be induced as a result of inadequate or irregular hormone production. As a result, prophylactic methods and treatment regimens to alleviate these symptoms frequently include low dosages of estrogens.

But increased levels of estrogens, including estradiol, whether due to prescription or naturally-occurring increases, may lead to the symptoms and disorders previously mentioned. To mitigate the effect of increased estradiol levels on the endometrium, progesterone administration is often a prophylactic method or prescribed treatment to prevent the negative effects of estrogens such as endometrial hyperplasias and related disorders.

These prophylactic methods and prescribed treatments involving the use of one or more of a group of medications designed to supplement hormone levels in women who experience irregular or decreased hormone production or who lack adequate hormone production, may generally be referred to as hormone replacement therapy (HRT).

Hormone replacement therapy (HRT) is a medical treatment that involves the use of one or more of a group of medications designed to supplement hormone levels in women who lack adequate hormone production. It can mitigate and prevent symptoms caused by diminished circulating estrogen and progesterone hormones.

HRT is available in various forms. One therapy involves administration of low dosages of one or more estrogen(s) or one or more chemical analogues. Another involves administration of progesterone or one or more chemical analogues. Among other effects, progesterone administration acts to mitigate certain undesirable side effects from estradiol administration or naturally-occurring elevated blood levels including endometrial hyperplasia (thickening) and prevention or inhibition of endometrial cancer. Progesterone is a C-21 steroidal sex hormone involved in the female menstrual cycle, pregnancy (supports gestation) and embryogenesis of humans and other species. Progesterone belongs to a class of hormones called progestogens, and is the major naturally occurring human progestogen. Like other steroids, progesterone consists of four interconnected cyclic hydrocarbons. Progesterone is hydrophobic, having a reported aqueous solubility of $0.007 \pm 0.0$ mg/ml. Progesterone is poorly absorbed when administered orally.

Existing progesterone prophylactic methods and prescribed treatments inconsistently or irregularly achieve high levels of absorbed progesterone at low dosages of progesterone. Existing methods and treatments often use synthetic progestins. Synthetic progestins such as medroxyprogesterone acetate or norethindrone acetate have been specifically designed to resist enzymatic degradation and remain active after oral administration. However, these compounds exert undesirable effects on the liver (notably on lipids) and often cause psychological side effects that can be severe enough to contraindicate their use.

One conventional progesterone therapeutic is PROMETRIUM (progesterone, USP) (Abbott Laboratories, Chicago, IL). PROMETRIUM is an FDA-approved drug, formulated in a peanut oil-based medium, containing micronized progesterone, but with a relatively large particle size fraction. The active ingredient in PROMETRIUM is considered to be structurally identical to naturally occurring progesterone produced by a woman's body (also known as a "bioidentical").

Clinical trials involving PROMETRIUM have shown significant intra- and inter-patient variability. For example, a clinical trial involving postmenopausal women who were administered PROMETRIUM once a day for five days resulted in the mean pharmacokinetic parameters listed in Table 1 (see Table 1, package insert for PROMETRIUM).

TABLE 1

Pharmacokinetic Parameters of PROMETRIUM Capsules

| Parameter | PROMETRIUM Capsules Davy Dose | | |
|---|---|---|---|
| | 100 mg | 200 mg | 300 mg |
| $C_{max}$ (ng/ml) | 17.3 ± 21.9 | 38.1 ± 37.8 | 60.6 ± 72.5 |
| $T_{max}$ (hr) | 1.5 ± 0.8 | 2.3 ± 1.4 | 1.7 ± 0.6 |
| AUC (0-10)(ng × hr/ml) | 43.3 ± 30.8 | 101.2 ± 66.0 | 175.7 ± 170.3 |

The unusually high variability in $C_{max}$ and AUC, as evidenced by the large reported standard deviation, may indicate that a significant percentage of patients are over-dosed or receive a sub-optimal dose.

The presence of peanut oil in the formulation excludes patients who are allergic to peanut oil. Peanut oil, like other peanut products, may act as an allergen. Indeed, there is a portion of the population that has severe reactions to peanut oil. Peanut allergies are becoming a significant health concern. Food allergies are a leading cause of anaphylaxis, with approximately 200 deaths occurring annually in the United States. While incidence and prevalence are not entirely known, it is suspected that about 6% of children and 4% of adults in North America are affected by food allergies. Many food allergies experienced by children are generally outgrown in adulthood with the exception of peanut allergies.

Progesterone and its analogues can be used to treat a variety of medical conditions, including acute diseases or disorders, as well as chronic diseases and disorders associated with long-term declines of natural progesterone levels.

Accordingly, improved formulations of progesterone would be advantageous. To that end, and disclosed herein, are, among other things, a new softgel progesterone pharmaceutical composition containing solubilized or partially solubilized progesterone, suspended progesterone, a solubilizing agent, and a non-ionic surfactant.

SUMMARY OF THE INVENTION

Various pharmaceutical formulations are disclosed herein. For example, pharmaceutical formulations are disclosed comprising ultra-micronized progesterone. Moreover, pharmaceutical formulations are disclosed comprising formulations of ultra-micronized progesterone, wherein the ultra-micronized progesterone is combined with a suitable excipient.

Thus, in various illustrative embodiments, the invention comprises an encapsulated liquid pharmaceutical formulation for orally administering progesterone to a mammal in need thereof, said formulation comprising: progesterone, as the sole active pharmaceutical ingredient. The progesterone can be fully solubilized, or, more typically, partially solubilized, in a solubilizing agent, with any insoluble progesterone being suspended in the solubilizing agent. The solubilizing agent can comprise a medium chain fatty acid-polyolester or a mixture of medium chain fatty acid-polyol esters. The polyol can be, for example, a glycol such as ethylene glycol, polyethylene glycol, propylene glycol, polypropylene glycol, etc. In other embodiments, the polyol can be a triol such as glycerol. When the polyol is a glycol, the glycol can be mono- or di-esterified with a given fatty acid (simple) or can be a mixed di-ester using different medium chain fatty acids. When the polyol is glycerol, the glycerol can be mono-, di-, or tri-esterified giving a monoglyceride, diglyceride, or triglyceride. Typical di- and triglycerides are simple triglycerides, though in certain embodiments, the di- and triglycerides can be mixed. In particular, embodiments, the solubilizing agent can comprise a simple, mixed, or combination simple and mixed glycol di-ester. In still other embodiments, the solubilizing agent can be a simple, mixed, or combination simple and mixed triglyceride. For example, in a particular embodiment, the solubilizing agent can comprise an oil having simple and mixed triglycerides prepared from predominantly C8 and C10 fatty acids. An example of such a triglyceride is MIGLYOL® 812.

In certain embodiments, the formulation can further comprise a non-ionic surfactant. As discussed elsewhere herein, the non-ionic surfactant can comprise GELUCIRE 44/14.

In certain embodiments the progesterone is micronized or ultra-micronized. In certain embodiments, at least about 80 wt % of the total progesterone is micronized. The fatty acids can be predominantly (>50 wt %): C6 to C12 fatty acids, C6 to C10 fatty acids, C8 to C12 fatty acids, or C8 to C10 fatty acids. Some embodiments comprise a non-ionic surfactant that comprises C8 to C18 fatty acid esters of glycerol and polyethylene glycol.

In other embodiments, a softgel progesterone pharmaceutical composition as a hormone replacement therapy (HRT), or as a prophylactic method or a prescribed treatment to mitigate the associated symptoms associated with irregular or inadequate hormone levels is provided.

In particular embodiments, this disclosure provides a pharmaceutical composition for orally administering progesterone to a subject in need thereof, the composition comprising: an amount of progesterone; a solubilizing agent; and a nonionic surfactant selected from the group consisting of lauroyl macrogol-32 glycerides EP (GELUCIRE 44/11), lauroyl polyoxyl-32 glycerides (GELUCIRE 44/14), and caprylocaproyl macrogol-8 glycerides EP; wherein the solubilizing agent comprises at least one C6-C12 fatty acid mono-, di-, or tri-ester of glycerol and wherein the composition has a total mass.

In one embodiment, the solubilizing agent comprises at least one $C_6$-$C_{12}$ fatty acid mono-ester of glycerol.

In another embodiment, the solubilizing agent comprises at least one $C_6$-$C_{12}$ fatty acid di-ester of glycerol.

In another embodiment, the solubilizing agent comprises at least one $C_6$-$C_{12}$ fatty acid tri-ester of glycerol.

In yet another embodiment, the tri-ester of glycerol comprises predominantly esters of caprylic fatty acid ($C_8$) and capric fatty acid ($C_{10}$).

In a further embodiment, the tri-ester of glycerol is MIGLYOL® 812.

In certain embodiments, the solubilizing agent is medium chain triglycerides (MIGLYOL® 812).

In certain embodiments, the nonionic surfactant is lauroyl polyoxyl-32 glycerides (GELUCIRE® 44/14).

In some embodiments, the amount of progesterone is from 25 mg to 200 mg.

In particular embodiments, the amount of progesterone is 75 mg or 150 mg.

In some embodiments, the amount of progesterone includes a solubilized amount of progesterone and a suspended amount of progesterone.

In certain embodiments, the composition is provided in a gelatin capsule.

In some embodiments, the total mass of the composition is less than 500 mg.

In other embodiments, the composition provides increased progesterone bioavailability compared to micronized progesterone suspended in peanut oil.

In certain embodiments, the solubilizing agent comprises predominantly at least one $C_6$-$C_{12}$ fatty acid mono-, di-, or tri-ester of glycerol.

In other embodiments, this disclosure provides a pharmaceutical composition for orally administering progesterone to a subject in need thereof, the composition comprising: 75, 150, 200, or 300 mg of progesterone; a solubilizing agent comprising predominantly a triglyceride oil of C8 and C10 fatty acid esters; and lauroyl polyoxyl-32 glycerides (GELUCIRE 44/14).

This disclosure also provides a method of preventing endometrial hyperplasia, the method comprising administering to a patient in need thereof a composition comprising: an amount of progesterone; a solubilizing agent; and a nonionic surfactant selected from the group consisting of lauroyl macrogol-32 glycerides EP (GELUCIRE 44/11), lauroyl polyoxyl-32 glycerides (GELUCIRE 44/14), and caprylocaproyl macrogol-8 glycerides EP; wherein the solubilizing agent comprises at least one $C_6$-$C_{12}$ fatty acid mono-, di-, or tri-ester of glycerol and wherein the composition has a total mass.

In certain embodiments of the method, the amount of progesterone is 150 mg.

In other embodiments, this disclosure provides a method of treating amenorrhea, the method comprising administering to a patient in need thereof a composition comprising: an amount of progesterone; a solubilizing agent; and a nonionic surfactant selected from the group consisting of lauroyl macrogol-32 glycerides EP (GELUCIRE 44/11), lauroyl polyoxyl-32 glycerides (GELUCIRE 44/14), and caprylocaproyl macrogol-8 glycerides EP; wherein the solubilizing agent comprises at least one $C_6$-$C_{12}$ fatty acid mono-, di-, or tri-ester of glycerol and wherein the composition has a total mass.

In certain embodiments of the noted method, the amount of progesterone is 150 mg or 300 mg.

In certain embodiments, the amount of progesterone comprises about 33% by weight of the composition; the solubilizing agent comprises about 65% by weight of the composition, the non-ionic surfactant comprises about 1.7% by weight of the composition.

In further embodiments, the amount of progesterone comprises about 33.33% by weight of the composition; the solubilizing agent comprises about 64.93% by weight of the composition, the non-ionic surfactant comprises about 1.67% by weight of the composition.

In certain embodiments, the composition further comprises an antioxidant.

In particular embodiments, the antioxidant is butylated hydroxy toluene.

In certain embodiments, the solubilizing agent is MIGLYOL 812.

In certain embodiments, the non-ionic surfactant is lauroyl polyoxyl-32 glycerides (GELUCIRE 44/14).

In some embodiments, the amount of progesterone is 200 mg.

In other embodiments, the amount of progesterone is 150 mg.

BRIEF DESCRIPTION OF THE DRAWINGS

The accompanying drawings are included to provide a further understanding of the disclosure and are incorporated in and constitute a part of this specification, illustrate embodiments of the disclosure, and together with the description serve to explain the principles of the disclosure.

FIG. 7 illustrates a Linear Plot of Mean Plasma Progesterone (Corrected) Concentrations Versus Time (N=62).

FIG. 8 illustrates a graph that is a Semi-logarithmic Plot of Mean Plasma Progesterone (Corrected) Concentrations Versus Time (N=62).

FIG. 9 illustrates a graph that is a Linear Plot of Mean Plasma Progesterone (Uncorrected) Concentrations Versus Time (N=62).

FIG. 10 illustrates a graph that is a Semi-logarithmic Plot of Mean Plasma Progesterone (Uncorrected) Concentrations Versus Time (N=62).

DETAILED DESCRIPTION

Figure 1:
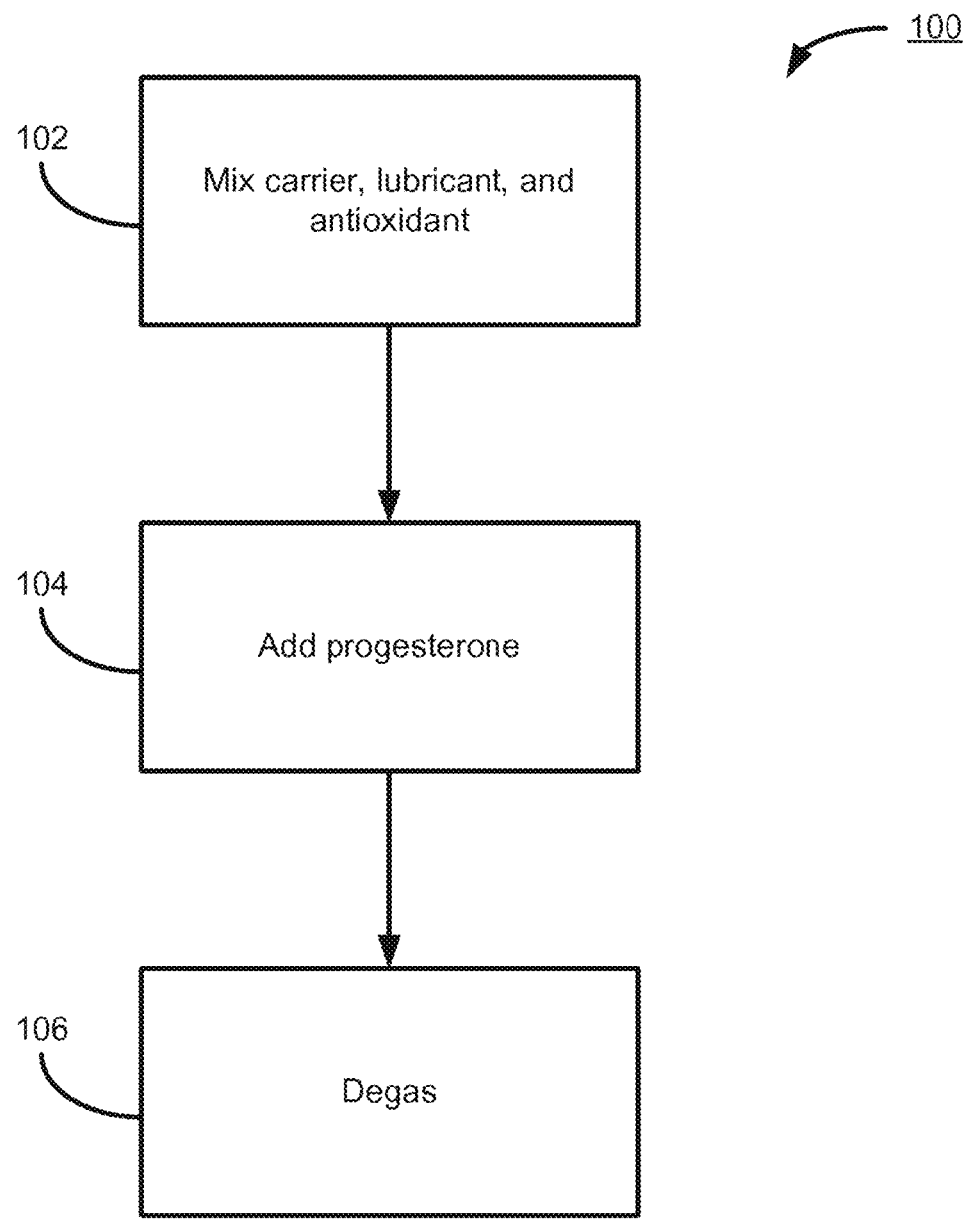
FIG. 1 illustrates a process to produce fill material in accordance with various embodiments.

This disclosure provides a pharmaceutical formulation comprising progesterone and a solubilizing agent. In some embodiments, a pharmaceutical formulation comprising ultra-micronized progesterone is provided. As described in detail herein, various solubilizing agents, lubricants, and other excipients may be included. In further embodiments, ultra-micronized progesterone formulations provide improved bioavailability and other pharmacokinetic improvements. These embodiments are described in sufficient detail to enable those skilled in the art to practice these embodiments. Further, other embodiments may be used and other changes may be made without departing from the scope of this disclosure. The following detailed description is therefore not to be taken in a limiting sense. As used in this disclosure, the term "or" is a logical disjunction and does not indicate an exclusive disjunction unless expressly indicated as such with the terms "either," "unless," "alternatively," and words of similar effect.

Definitions

Unless otherwise specified, the following definitions apply.

The phrase "active pharmaceutical ingredient" or "API" as used herein, means the active compound(s) used in formulating a drug product. In exemplary embodiments, the API is progesterone.

The term "bioequivalent" has the meaning prescribed in 21 CFR § 320.1(e), e.g. the absence of a significant difference in the rate and extent to which the active ingredient or active moiety in pharmaceutical equivalents or pharmaceutical alternatives becomes available at the site of drug action when administered at the same molar dose under similar conditions in an appropriately designed study. Where there is an intentional difference in rate (e.g., in certain extended release dosage forms), certain pharmaceutical equivalents or alternatives may be considered bioequivalent if there is no significant difference in the extent to which the active ingredient or moiety from each product becomes available at the site of drug action. This applies only if the difference in the rate at which the active ingredient or moiety becomes available at the site of drug action is intentional and is reflected in the proposed labeling, is not essential to the attainment of effective body drug concentrations on chronic use, and is considered medically insignificant for the drug. In practice, two products are considered bioequivalent if the 90% confidence interval of the $C_{max}$, AUC, or, optionally, $T_{max}$ is within 80.00% to 125.00%.

The term "bioidentical" or "natural" used in conjunction with the hormones disclosed herein, means hormones that are identical to or match the chemical structure and effect of those that occur naturally or endogenously in the human body. An exemplary natural estrogen is estradiol.

The term "drug product" as used herein means at least one API in combination with at least one excipient, wherein the API and at least one excipient are provided in unit dosage form.

The term "estrogen" means generally the different hormone types of estrogen, synthetically or naturally occurring, including estradiol, estriol, and estrone.

The term "estradiol" means (17B)-estra-1,3,5(10)-triene-3,17-diol. Estradiol is also called 17ß-estradiol, oestradiol, or E2 and is found endogenously in the human body. Irrespective of the what it is called, estradiol refers to the bio-identical form of estradiol found in the human body having the structure:

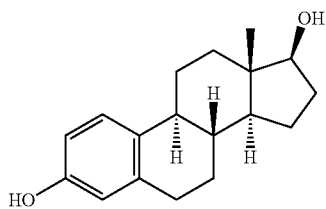

Estradiol is supplied in an anhydrous or a hemi-hydrate form; for the purposes of this disclosure, the anhydrous form or the hemihydrate form can be substituted for the other by accounting for the water or lack of water according to well-known and understood techniques.

The phrase "equivalent dosage form" as used herein refers to a dosage form that is identical to a reference dosage form in composition (e.g. identical solubilizing agent(s), non-ionic surfactant(s), and API), but differs from the reference dosage form in the amount of API present or in the ratio of the various components in the reference dosage form.

The term "ultra-micronized progesterone," as used herein, refers to micronized progesterone having an X50 particle size value below about 20 microns or having an X90 value below about 25 microns. The term "X50" as used herein, means that half of the particles in a sample are smaller in diameter than a given number. For example, ultra-micronized progesterone having an X50 of 5 microns means that, for a given sample of ultra-micronized progesterone, half of the particles have a diameter of less than 5 microns. In that regard, similar terms, in the form XYY mean that YY percent of the particles in the sample are smaller in diameter than a given number. For example, X90 means that ninety percent of the particles in a sample are smaller in diameter than a given number.

The term "administer," "administration," "deliver" or "delivery" (collectively "administration"), as used herein, means oral administration of the formulation disclosed herein, preferably in a soft gelatin capsule.

The term "glyceride" is an ester of glycerol (1,2,3-propanetriol) with acyl radicals of fatty acids and is also known as an acylglycerol. If only one position of the glycerol molecule is esterified with a fatty acid, a "monoglyceride" is produced; if two positions are esterified, a "diglyceride" is produced; and if all three positions of the glycerol are esterified with fatty acids, a "triglyceride" or "triacylglycerol" is produced. A glyceride is "simple" if all esterified positions contain the same fatty acid; whereas a glyceride is "mixed" if the esterified positions contained different fatty acids. The carbons of the glycerol backbone are designated sn-1, sn-2 and sn-3, with sn-2 being in the middle carbon and sn-1 and sn-3 being the end carbons of the glycerol backbone.

The term "medium chain" is used to describe the aliphatic chain length of fatty acid containing molecules. "Medium chain" specifically refers to fatty acids, fatty acid esters, or fatty acid derivatives that contain fatty acid aliphatic tails or carbon chains that contain 6 (C6) to 14 (C14) carbon atoms, 8 (C8) to 12 (C12) carbon atoms, or 8 (C8) to 10 (C10) carbon atoms.

The terms "medium chain fatty acid" and "medium chain fatty acid derivative" are used to describe fatty acids or fatty acid derivatives with aliphatic tails (i.e., carbon chains) having 6 to 14 carbon atoms. Fatty acids consist of an unbranched or branched aliphatic tail attached to a carboxylic acid functional group. Fatty acid derivatives include, for example, fatty acid esters and fatty acid containing molecules, including, without limitation, mono-, di- and triglycerides that include components derived from fatty acids. Fatty acid derivatives also include fatty acid esters of ethylene or propylene glycol. The aliphatic tails can be saturated or unsaturated (one or more double bonds between carbon atoms). In some embodiments, the aliphatic tails are saturated (i.e., no double bonds between carbon atoms). Medium chain fatty acids or medium chain fatty acid derivatives include those with aliphatic tails having 6-14 carbons, including those that are C6-C14, C6-C12, C8-C14, C8-C12, C6-C10, C8-C10, or others. Examples of medium chain fatty acids include, without limitation, caproic acid, caprylic acid, capric acid, lauric acid, myristic acid, and derivatives thereof.

The term "oil," as used herein, refers to any pharmaceutically acceptable oil, especially medium chain oils, and specifically excluding peanut oil, that can suspend and/or solubilize bioidentical progesterone and/or estradiol, including starting materials and/or precursors thereof, including micronized progesterone and/or micronized estradiol as described herein.

The term "medium chain oil" refers to an oil wherein the composition of the fatty acid fraction of the oil is predominantly medium chain (i.e., C6 to C14) fatty acids, i.e., the composition profile of fatty acids in the oil is predominantly medium chain. As used herein, "predominantly" means that between 20% and 100% (inclusive of the upper and lower limits) of the fatty acid fraction of the oil is made up of medium chain fatty acids, i.e., fatty acids with aliphatic tails (i.e., carbon chains) having 6 to 14 carbons. In some embodiments, about 25%, about 30%, about 35%, about 40%, about 45%, about 50%, about 55%, about 60%, about 65%, about 70%, about 75%, about 85%, about 90% or about 95% of the fatty acid fraction of the oil is made up of medium chain fatty acids. Those of skill in the art that will readily appreciate that the terms "alkyl content" or "alkyl distribution" of an oil can be used in place of the term "fatty acid fraction" of an oil in characterizing a given oil or solubilizing agent, and these terms are used interchangeable herein. As such, medium chain oils suitable for use in the formulations disclosed herein include medium chain oils wherein the fatty acid fraction of the oil is predominantly medium chain fatty acids, or medium chain oils wherein the alkyl content or alkyl distribution of the oil is substantially medium chain alkyls (C6-C12 alkyls). It will be understood by those of skill in the art that the medium chain oils suitable for use in the formulations disclosed herein are pharmaceutical grade (e.g., pharmaceutical grade medium chain oils). Examples of medium chain oils include, for example and without limitation, medium chain fatty acids, medium chain fatty acid esters of glycerol (e.g., for example, mono-, di-, and triglycerides), medium chain fatty acid esters of propylene glycol, medium chain fatty acid derivatives of polyethylene glycol, and combinations thereof.

The term "ECN" or "equivalent carbon number" means the sum of the number of carbon atoms in the fatty acid chains of an oil, and can be used to characterize an oil as, for example, a medium chain oil or a long-chain oil. For example, tripalmitin (tripalmitic glycerol), which is a simple triglyceride containing three fatty acid chains of 16 carbon atoms, has an ECN of 3×16=48. Conversely, a triglyceride with an ECN=40 may have "mixed" fatty acid chain lengths of 8, 16 and 16; 10, 14 and 16; 8, 14 and 18; etc. Naturally occurring oils are frequently "mixed" with respect to specific fatty acids, but tend not to contain both long chain fatty acids and medium chain fatty acids in the same glycerol backbone. Thus, triglycerides with ECN's of 21-42 typically contain predominately medium chain fatty acids; while triglycerides with ECN's of greater than 43 typically contain predominantly long chain fatty acids. For example, the ECN of corn oil triglyceride in the USP would be in the range of 51-54. Medium chain diglycerides with ECN's of 12-28 will often contain predominately medium chain fatty chains, while diglycerides with ECN's of 32 or greater will typically contain predominately long chain fatty acid tails. Monoglycerides will have an ECN that matches the chain length of its sole fatty acid chain. Thus, monoglyceride ECN's in the range of 6-14 contain mainly medium chain fatty acids, and monoglycerides with ECN's 16 or greater will contain mainly long chain fatty acids.

The average ECN of a medium chain triglyceride oil is typically 21-42. For example, as listed in the US Pharmacopeia (USP), medium chain triglycerides having the following composition as the exemplary oil in the table below

| Fatty-acid Tail Length | % of oil | Exemplary Oil |
| --- | --- | --- |
| 6 | ≤2.0 | 2.0 |
| 8 | 50.0-80.0 | 70.0 |
| 10 | 20.0-50.0 | 25.0 |
| 12 | ≤3.0 | 2.0 |
| 14 | ≤1.0 | 1.0 | would have an average ECN of 3*[(6*0.02)+(8*0.70)+(10*0.25)+(12*0.02)+(14*0.01)]=25.8. The ECN of the exemplary medium chain triglycerides oil can also be expressed as a range (per the ranges set forth in the USP) of 24.9-27.0. For oils that have mixed mono-, di-, and trigylcerides, or single and double fatty acid glycols, the ECN of the entire oil can be determined by calculating the ECN of each individual component (e.g., C8 monoglycerics, C8 diglycerides, C10 monoglycerides, and C10 monoglycerides) and taking the sum of the relative percentage of the component multiplied by the ECN normalized to a monoglyceride for each component. For example, the oil having C8 and C10 mono- and diglycerides shown in the table below has an ECN of 8.3, and is thus a medium chain oil.

| Fatty-acid Tail Length | % of oil | ECN as % of oil (chain length) × (% in oil) | ECN as % of oil normalized to monoglyceride |
| --- | --- | --- | --- |
| C8 monoglyceride | 47 | 8 × 0.47 = 3.76 | 3.76 |
| C10 monoglyceride | 8 | 10 × 0.08 = 0.8 | 0.8 |
| C8 diglyceride | 38 | 2 × (8 × 0.38) = 6.08 | 6.08/2 = 3.04 |
| C10 diglyceride | 7 | 2 × (10 × 0.07) = 1.4 | 1.4/2 = 0.7 |
| OIL ECN (normalized to monoglycerides) | | | 8.3 |

Expressed differently, ECN can be calculated as each chain length in the composition multiplied by its relative percentage in the oil: (8*0.85)+(10*0.15)=8.3.

The term "patient" refers to a human individual who has received, who might receive, or is receiving health or pharmaceutical care, or is under the supervision and care of a physician, pharmacist, or medically trained professional. This individual may be expecting this care, may be currently receiving it, or may have already received it.

The term "progesterone" refers to pregn-4-ene-3,20-dione. Progesterone is also interchangeably called P4 and is found endogenously in the human body. As used herein, progesterone refers to the bio-identical or body-identical form of progesterone found in the human body having the structure:

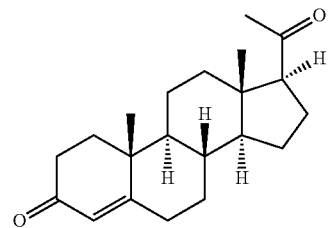

The term "solubilized progesterone" means that the progesterone or a portion thereof is solubilized or dissolved in the solubilizing agent(s) or the formulations disclosed herein. In some embodiments, the progesterone is "partially solubilized" with a portion of the progesterone being solubilized or dissolved in the solubilizing agent and a portion of the progesterone being suspended in the solubilizing agent. Partially solubilized progesterone may include progesterone that is about 1% solubilized, about 5% solubilized, about 10% solubilized, about 15% solubilized, or about 20% solubilized, about 30% solubilized, about 40% solubilized, about 50% solubilized, about 60% solubilized, about 70% solubilized, about 80% solubilized, about 85% solubilized, about 90% solubilized or about 95% solubilized. In other embodiments, the progesterone is "fully solubilized" with all or substantially all of the progesterone being solubilized or dissolved in the solubilizing agent. Fully solubilized progesterone may include progesterone that is about 97% solubilized, about 98% solubilized, about 99% solubilized or about 100% solubilized. In particular embodiments, the progesterone is less than about 20% solubilized. Solubility can be expressed as a mass fraction (% w/w, which is also referred to as wt %).

The term "pharmaceutical composition" refers to a composition comprising at least a solubilizing agent and progesterone. As used herein, pharmaceutical compositions are delivered, for example via oral administration. Furthermore, as used herein, "pharmaceutical composition" and "formulation" are used interchangeably.

The term "uniform distribution" means at least one of uniform dispersion, solubility, or lack of agglomeration of progesterone in gastric juices compared to PROMETRIUM.

The term "gastric juices" means the watery, acidic digestive fluid that is secreted by various glands in the mucous membrane of the stomach and consists chiefly of hydrochloric acid, pepsin, rennin, and mucin.

The term "excipients," as used herein, refers to non-API substances such as solubilizing agents, anti-oxidants, oils, lubricants and others used in formulating pharmaceutical products. They are generally safe for administering to humans according to established governmental standards, including those promulgated by the United States Food and Drug Administration.

The term "carrier," as used herein, means any substance or mixture of substances that may be mixed with or contain an API (e.g., ultra-micronized progesterone). The term carrier is interchangeable with solubilizing agent.

The term "capsule," as used herein, refers to a generally safe, readily dissolvable enclosure for carrying certain pharmaceutical products, and includes hard or soft shell capsules.

The term "softgel," includes soft shell capsules, including soft-gelatin capsules and soft vegetable-based capsules, and soft capsules made from other materials providing the composition of such soft capsules are compatible with the formulations of the various embodiments described herein. A softgel may comprise two primary phases: a gel or vegetable-based capsule and a fill material of the pharmaceutical formulation as described herein. In particular embodiments, the weight of the fill material does not exceed 500 mg, i.e. the fill material weighs less than 500 mg, less than 450 mg, less than 400 mg, less than 350 mg, less than 300 mg, less than 250 mg, less than 200 mg, or less than 150 mg.

The term "bioavailability" has the meaning prescribed in 21 CFR § 320.1(a): the rate and extent to which the active ingredient or active moiety is absorbed from a drug product and becomes available at the site of action. For drug products that are not intended to be absorbed into the bloodstream, bioavailability may be assessed by measurements intended to reflect the rate and extent to which the active ingredient or active moiety becomes available at the site of action. For example, bioavailability can be measured as the amount of API in the blood (serum or plasma) as a function of time. Pharmacokinetic (PK) indicators such as AUC, $C_{max}$, or $T_{max}$ may be used to measure and assess bioavailability. Absorption as used in this definition can include absorption in the stomach, intestines, or other tissue that help facilitate absorption of the API into the bloodstream.

The term "co-administered" as used herein, means that two drug products are administered simultaneously or sequentially on the same or different days.

The terms "pharmacokinetics," "pharmacokinetic measurements," "pharmacokinetic parameters," and "PK parameters" refers to parameters or measures used to assess bioavailability such as AUC, $C_{max}$, or $T_{max}$ include assessments and determinations to study absorption, distribution, metabolism, and excretion of a drug.

The term "reference listed drug product" ("RLD") means PROMETRIUM (progesterone, USP) (Abbott Laboratories, Chicago, IL). PROMETRIUM is an FDA-approved drug, formulated in a peanut oil-based medium, containing micronized progesterone, but with a relatively large particle size fraction.

The term "secretory activity" refers to complete and partial secretory activity of the endometrium as is well understood in the art and as is discussed at length in Noyes, R. W., Hertig, A. T. and Rock, J. (1950), Dating the endometrial biopsy. Fertil. Steril., 1, 3-25, which is incorporated herein by reference. See also, Deliqdisch, L., (1993), Effects of hormone therapy on the endometrium. Mod Pathol. January, vol. 6(1), pp 94-106, which is incorporated herein by reference. Noyes et al., is also referenced for additional information regarding endometrial biopsies.

The term "solubilized" refers to the amount of an API that is in solution. Solubility and percent solubility are expressed herein as a mass fraction (mg/g) or (% w/w, also referred to as wt. %).

The term "solubilizing agent" refers to an agent or combination of agents that solubilize an active pharmaceutical ingredient (e.g., estradiol or progesterone). For example and without limitation, suitable solubilizing agents include medium chain oils and other solvents and co-solvents that solubilize or dissolve an active pharmaceutical ingredient to a desirable extent. Solubilizing agents suitable for use in the formulations disclosed herein are pharmaceutical grade solubilizing agents (e.g., pharmaceutical grade medium chain oils). It will be understood by those of skill in the art that other excipients or components can be added to or mixed with the solubilizing agent to enhance the properties or performance of the solubilizing agent or resulting formulation. Examples of such excipients include, but are not limited to, surfactants, emulsifiers, thickeners, colorants, flavoring agents, etc. In some embodiments, the solubilizing agent is a medium chain oil and, in some other embodiments, the medium chain oil is combined with a co-solvent(s) or other excipient(s).

The term "subject" refers to both human and non-human animal subjects who are administered the pharmaceutical composition of this disclosure. Specifically intended are mammalian subjects. More specifically intended are human subjects.

The term "area under the curve" or "AUC" refers to the area under the curve defined by changes in the blood concentration of an active pharmaceutical ingredient (e.g., progesterone), or a metabolite of the active pharmaceutical ingredient, over time following the administration of a dose of the active pharmaceutical ingredient. "$AUC_{0-\infty}$" is the area under the concentration-time curve extrapolated to infinity following the administration of a dose. "$AUC_{0-t}$" is the area under the concentration-time curve from time zero to time t following the administration of a dose, wherein t is the last time point with a measurable concentration.

The term "$C_{max}$" refers to the maximum value of blood concentration shown on the curve that represents changes in blood concentrations of an active pharmaceutical ingredient (e.g., progesterone), or a metabolite of the active pharmaceutical ingredient, over time.

The term "$T_{max}$" refers to the time that it takes for the blood concentration of an active pharmaceutical ingredient (e.g., estradiol or progesterone), or a metabolite of the active pharmaceutical ingredient, to reach the maximum value.

Optionally, the term, "$T_{1/2}$" as used herein, refers to the time that it takes for progesterone blood concentration to decline to one-half of the maximum level.

Collectively AUC, $C_{max}$, and optionally $T_{max}$ and $T_{1/2}$, are the principle pharmacokinetic parameters that can characterize the pharmacokinetic responses of a particular drug product such as progesterone in an animal or human subject.

DESCRIPTION

Provided herein are oral pharmaceutical compositions comprising solubilized or partially solubilized progesterone. Further disclosed herein are data demonstrating the efficacy of these pharmaceutical compositions, as well as methods of using the described pharmaceutical compositions. Generally, the pharmaceutical compositions disclosed herein can be useful in mitigating the symptoms and effects of increased, decreased, or irregular estrogen levels.

Additional aspects and embodiments of this disclosure include: providing increased patient ease of use while potentially minimizing certain side effects from erroneous use, providing reduced metabolic and vascular side effects of commonly used synthetic progesterone, providing reduced food and allergy effects, providing improved bioavailability of progesterone as compared to the PROMETRIUM®, and in some embodiments providing for improved bioavailability of progesterone or a bioequivalent progesterone product at a reduced dose of API compared to the RLDs.

Various embodiments are improvements over exiting progesterone formulations, treatments, and methods of using these formulations and treatments. While not bound by theory, the elements of the pharmaceutical compositions of this disclosure provide improved bioavailability, improved pharmacokinetics, bioequivalent pharmaceutical compositions, and the potential to reduce the administered dosage strength. Bioavailability comparisons to commercially available forms, such as tablet and capsule forms, may be determined by standard pharmacokinetic techniques.

In embodiments, progesterone is solubilized or partially solubilized (partially suspended) when administered. The type of progesterone used, the form of that progesterone (i.e., solubilized or suspended), the different solubilizing agent used, the different excipients used, and the administration under proper conditions (i.e. fed, absence of concomitant medications, etc.) contribute, in part, to the improvements over existing progesterone compositions, methods, and treatments.

In embodiments, the pharmaceutical compositions do not include peanut oil.

In certain embodiments, the API is progesterone, which is solubilized or partially solubilized (partially suspended). In embodiments, progesterone is the sole API.

Generally, the pharmaceutical formulations described herein are prepared and administered as filled capsules, typically soft capsules or softgels of one or more materials well known in the art including, for example and without limitation, soft gelatin capsules. Ultra-micronized progesterone, as described herein, may also be prepared for administration in tablets or other well-known orally administered dosage forms using standard techniques.

In illustrative embodiments, total progesterone, i.e., dissolved and suspended progesterone, can be 20 to 50 wt %, e.g., 30 to 35 wt %, based on the weight of the entire fill, i.e., the liquid pharmaceutical formulation.

Other embodiments disclosed herein further provide more uniform dissolution of progesterone and reduced intra- and inter-patient PK parameters when compared to equal dosages of PROMETRIUM. Dissolution uniformity of progesterone in a formulation of this disclosure compared to PROMETRIUM at equal dosage strengths and using the same USP apparatus can be determined using standard techniques established for API dissolution testing, including that which is described in the examples below.

According to the PROMETRIUM prescribing information, progesterone absorption is highly variable from patient to patient and within the same patient. A clinical trial involving postmenopausal women who were administered PROMETRIUM once a day for five days resulted in the mean PK parameters listed in the following table:

| Parameter | PROMETRIUM Capsules Daily Dose | | |
|---|---|---|---|
| | 100 mg | 200 mg | 300 mg |
| $C_{max}$ (ng/ml) | 17.3 +/− 21.9 | 38.1 +/− 37.8 | 60.6 +/− 72.5 |
| $T_{max}$ (hr) | 1.5 +/− 0.8 | 2.3 +/− 1.4 | 1.7 +/− 0.6 |
| $AUC_{0-10}$ (ng × hr/ml) | 43.4 +/− 30.8 | 101.2 +/− 66.0 | 175.7 +/− 170.3 |

These values are highly variable as demonstrated by their standard deviations which, in some cases, exceed 100% of the noted mean value. In particular illustrative aspects and embodiments of this invention, it is possible, though not necessary, to reduce the standard deviations in one or more of these PK parameters.

Reduced intra- and inter-patient variability of progesterone according to this disclosure compared to PROMETRIUM can be assessed using techniques known to those of ordinary skill in the art and described elsewhere herein.

Other aspects of this disclosure include the use of formulations as described herein wherein progesterone is at least one API in said formulation for the treatment of an animal, especially a mammal, including humans: for endometrial hyperplasia; for secondary amenorrhea; as a method of treatment for preterm birth, when said animal has a shortened cervix, and other disease states or conditions treated with supplemental progesterone (collectively, "Progesterone-deficient States") in a subject in need of treatment, and with a non-toxic effective amount of said formulations.

The terms "treat," "treating," and "treatment" refer to any indicia of success in the treatment or amelioration of an injury, disease, or condition, including any objective or subjective parameter such as abatement; remission; diminishing of symptoms or making the injury, disease, or condition more tolerable to the patient; slowing in the rate of degeneration or decline; or improving a patient's physical or mental well-being. The treatment or amelioration of symptoms can be based on objective or subject parameters, including the results of a physical examination, neuropsychiatric examinations, or psychiatric evaluation.

For purposes of this disclosure, "prophylaxis" refers to administration of the progesterone, to an animal, especially a mammal, and in particular a human, to protect the animal from any of the disorders set forth herein, as well as others, before or after the disorder has occurred in the subject.

Exemplary dosage strengths for progesterone for use in the formulations described herein include, without limitation, 25 mg, 50 mg, 75 mg, 100 mg, 125 mg, 150 mg, 175 mg, 200 mg, 250 mg, 300 mg, 350 mg and 400 mg. In embodiments, progesterone dosage strength is from at least 25 mg to at least 200 mg. Specific dosage embodiments contain at least: 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, or 200 mg of progesterone per capsule.

In certain embodiments, the pharmaceutical compositions can contain at least about 50 mg, 75 mg, 100 mg, 150 mg, or 200 mg of progesterone. In certain embodiments, the pharmaceutical compositions contain from about 25 mg to about 50 mg, from about 75 mg to 100 mg, from about 50 mg to about 100 mg, about 75 mg, about 150 mg, about 200 mg, from about 100 mg to 150 mg, from about 150 mg to 200 mg, from 100 mg to 200 mg of progesterone. The lowest clinically effective dose of progesterone is used for treatment symptoms occurring due to irregular or inadequate hormone production, or for estrogen HRT patients. In one embodiment, the progesterone dosage is about 75 mg. In another embodiment, the progesterone dosage is about 150 mg. In another embodiment, the progesterone dosage is about 200 mg. In particular embodiments, the dosage is 75 mg, 150 mg, or 200 mg.

Solubilized compositions of this disclosure can be formulated for administration using techniques disclosed herein, and also using techniques well known in the art. Thus, an illustrative embodiment of a pharmaceutical composition of the invention comprises progesterone, at least 75% of the progesterone being solubilized (the balance being suspended/ultra-micronized as discussed elsewhere herein), and an oil, wherein the oil is medium chain fatty acid mono- and di-esters of one or more glycols, with or without surfactant.

In other embodiments, the progesterone in the pharmaceutical compositions is not more than about 20% solubilized, not more than about 19% solubilized, not more than about 18% solubilized, not more than about 17% solubilized, not more than about 16% solubilized, not more than about 15% solubilized, not more than about 14% solubilized, not more than about 13% solubilized, not more than about 12% solubilized, not more than about 11% solubilized, not more than about 10% solubilized, not more than about 9% solubilized, not more than about 8% solubilized, not more than about 7% solubilized, not more than about 6% solubilized, or not more than about 5% solubilized, with the balance being suspended in the formulation as discussed elsewhere herein. The suspended/ultra-micronized progesterone is absorbable by the body and retains biological functionality despite not being soluble in the formulation. In a particular embodiment, the progesterone is about 15% solubilized in the formulation, with balance (about 85%) being suspended/ultra-micronized. In another embodiment, the progesterone is about 5% solubilized in the formulation, with balance (about 95%) being suspended/ultra-micronized.

In certain embodiments, progesterone solubility in various solubilizing agents ranges from 27 mg/g to 95 mg/g. More specifically, in certain embodiments, progesterone's solubility in solubilizing agents is from 27.8 mg/g, 57.4 mg/g, 70.5 mg/g, 73.4 mg/g, 86.4 mg/g, to 95 mg/g.

Progesterone may be micronized/ultra-micronized via any one of the multiple methods typically utilized by the ordinarily skilled artisan.

Particle size may be determined in any suitable manner. For example, a Beckman Coulter LS 13 320 Laser Diffraction Particle Size Analyzer (the "Beckman Device") may be used to determine particle size. Particle size may be represented by various metrics, for example, through an X50 particle size, or X90 particle size, or similar descriptions of particle size.

The Beckman Device may be used with various modules for introducing a sample for analysis. The Beckman Device may be used with the LS 13 320 Universal Liquid Module ("ULM"). The ULM is capable of suspending samples in the size range of 0.017 μm to 2000 μm. The ULM is a liquid based module that allows for delivery of the sample to the sensing zone. The ULM recirculates the sample through the Beckman Device. The ULM comprises two hoses, one for fluid delivery and another for waste. The total volume used may be 125 mL or less. A sample mass of from about 1 mg to about 10 g may be used. The ULM may interact with the Beckman Device via pins that fit into slots on the ULM. The ULM may use a variety of suspension fluids, for example, water, butonol, ethanol, chloroform, heptanes, toluene, propanol, COULTER Type 1B Dispersant ("Coulter 1B"), and a variety of other suspension fluids. Surfactants may also be used, though pump speed should be adjusted to prevent excessive bubbling. Coulter 1B may comprise one or more of acetaldehyde, ethylene oxide, or 1,4-dioxane. The Beckman Device may be configured to use a variety of optical theories, including the Fraunhofer optical model and the Mie Theory.

The Beckman Device may comprise software to control the Beckman Device while the ULM is in use. The software may control, for example, pump speed, use of de-bubble routine, rinse routine, sonicate routine, and fill routine, among others. Parameters regarding the sample run may also be configured. For example, run length may be set. Though any suitable run length may be used, in various embodiments, a time period of 30 seconds to 120 seconds, and preferably between 30 seconds and 90 seconds may be used.

The Beckman Device may be used with the LS 13 320 Micro Liquid Module ("MLM"). The MLM is capable of suspending samples in the size range of 0.4 μm to 2000 μm. The MLM is a liquid based module that allows for delivery of the sample to the sensing zone. The MLM includes a stirrer. The total volume used may be 12 mL or less. The MLM may use a variety of suspension fluids, both aqueous and non-aqueous.

In various embodiments, ultra-micronized progesterone has an X50 value of less than about 15 microns, less than about 10 microns, less than about 5 microns or less than about 3 microns; and an X90 value of less than about 25 microns, less than about 20 microns, or less than about 15 microns.

In various embodiments, ultra-micronized progesterone is formulated with peanut and peanut-oil free excipients.

Solvent System

In various embodiments, a solvent system solubilizes one or more APIs, and in particular, progesterone. The solvent system is a mixture of solubilizing agents, together with co-solvents, surfactants, or other excipients. In certain embodiments, the solvent system comprises non-toxic, pharmaceutically acceptable solvents (alternatively referred to as "carriers"), co-solvents, surfactants, and excipients suitable for oral administration or absorption.

In embodiments, oils having medium chain fatty acids as a predominant or majority component are used as solubilizing agents/carriers to solubilize the one or more APIs. In certain embodiments, the solubilizing agents comprise medium chain fatty acid esters (e.g., esters of glycerol, ethylene glycol, or propylene glycol) or mixtures thereof. In certain embodiments, the medium chain fatty acids comprise chain lengths from C6 to C14. In certain embodiments the medium chain fatty acids comprise chain lengths from C6 to C12. In still other embodiments, the medium chain fatty acids are mono-, di-, or triglycerides predominately with chain lengths from C8 to C10. As noted elsewhere herein, the medium chain fatty acids can be saturated. In certain embodiments, the medium chain fatty acids are predominantly saturated, i.e., greater than about 60%, greater than about 70%, greater than about 75%, greater than about 80%, greater than about 85%, greater than about 90%, or greater than about 95% saturated. In particular embodiments, the solubilizing agent comprises a mixed triglyceride predominantly comprising C8 and C10 fatty acids. In other particular embodiments, the solubilizing agent comprises both simple and mixed triglycerides predominately comprising C8 and C10 fatty acids. In particular embodiments, the solubilizing agent comprises a mixed triglyceride predominantly comprising saturated C8 and C10 fatty acids. In other particular embodiments, the solubilizing agent comprises both simple and mixed triglycerides predominately comprising saturated C8 and C10 fatty acids.

In some embodiments, the solubilizing agent/carrier is selected to enhance dissolution or suspension of progesterone. In further various embodiments, the solubilizing agent/carrier is selected to enhance absorption of the API by cells of a mammal. For example, certain carriers may be selected to enhance absorption of the other formulation components, including the API. Absorption may comprise absorption into any cell and particularly absorption into digestive system cells, such as intestinal cells, and cells of the female reproductive system, such as the vagina and the cervix. Selected mono-, di-, or triglyercides are particularly suited to aid in cellular absorption.

In certain embodiments, a surfactant is used to aid in solubilizing, partially solubilizing, or suspending progesterone in the solubilizing agent. For example, a surfactant, such as GELUCIRE 44/14, can be used. In certain embodiments, GELUCIRE 44/14 may be heated to approximately 45-50° C. When the surfactant is completely melted, it is added to an appropriate container that contains the solubilizing agent. The solubilizing agent and surfactant are mixed. During this mixing process the progesterone is added, thus, solubilizing, partially solubilizing, or suspending progesterone. In certain embodiments, the solubilizing agent is liquid at between room temperature and about 50° C., at or below 50° C., at or below 40° C., or at or below 30° C.

In various embodiments, the solubilizing agent/carrier can be an oil having medium chain fatty acids as a majority or predominant component. Suitable medium chain fatty acids include caproic acid (C6), enanthic acid (C7), caprylic acid (C8), pelargonic acid (C9), capric acid (C10), undecylic acid (C11), lauric acid (C12), tridecylic acid (C13), and myristic acid (C14). In use, these fatty acids are predominantly saturated (e.g., greater than 50%, greater than about 60%, greater than about 70%, greater than about 80%, greater than about 90%, or greater than about 95%, or about 100%). In certain embodiments, predominantly C6 to C12 saturated fatty acids are contemplated. In certain embodiments, predominately C8 to C10 saturated fatty acids are contemplated. In certain embodiments, these fatty acids may be bound to glycerin, propylene glycol, ethylene glycol, or polyethylene glycol. In certain embodiments, the solubilizing agent is selected from at least one of a solvent or co-solvent.

In particular embodiments, the solubilizing agent can comprise a mixture of caprylic/capric triglycerides; caproic/caprylic/capric/lauric triglycerides; caprylic/capric/linoleic triglycerides; caprylic/capric/succinic triglycerides; propylene glycol dicaprylate/dicaprate; and combinations and derivatives thereof. In further embodiments, in addition to the various mixtures of the specified triglycerides, the solubilizing agent can further include polyethylene glycol.

Suitable carriers/solubilizing agents further include esters of saturated coconut and palm kernel oil and derivatives thereof, including fractionated coconut oils and palm kernel oils; and triglycerides of fractionated vegetable fatty acids, and derivatives thereof and combinations thereof. In further various embodiments, the carrier/solubilizing agent may comprise one or more monoglycerides, diglycerides, triglycerides, and combinations thereof having predominately C6-C12 fatty acid esters. Specifically contemplated as the solvent are mono-, di-, and triglycerides of saturated C8-C10 (caprylic/capric) fatty acids. Exemplary glycerin based solubilizing agents include MIGLYOLs®, which are caprylic/capric triglycerides (SASOL Germany GMBH, Hamburg). MIGLYOLs includes MIGLYOL 810 (caprylic/capric triglyceride), MIGLYOL 812 (caprylic/capric triglyceride), MIGLYOL 816 (caprylic/capric triglyceride), and MIGLYOL 829 (caprylic/capric/succinic triglyceride). Other caprylic/capric triglyceride solubilizing agents are likewise contemplated, including, for example: caproic/caprylic/capric/lauric triglycerides; caprylic/capric/linoleic triglycerides; caprylic/capric/succinic triglycerides. In certain embodiments, CAPMUL MCM, medium chain mono- and di-glycerides of caprylic/capric fatty acids, is the solubilizing agent. In other embodiments, CAPMUL PG-8 (Propylene Glycol Monocaprylate), CAPMUL PG-10 (Propylene Glycol Monocaprate), or other caprylic/capric CAPMULs is the solubilizing agent. Triglycerides of fractionated vegetable fatty acids, and combinations or derivatives thereof can be the solubilizing agent, in certain embodiments.

Additional examples of solubilizing agents include a polyethylene glycol glyceride (Gelucire®; GATTEFOSSE SAS, Saint-Priest, France); a propylene glycol; a caproic/caprylic/capric/lauric triglyceride; a caprylic/capric/linoleic triglyceride; a caprylic/capric/succinic triglyceride; propylene glycol monocaprylate; propylene glycol monocaprate; (Capmul® PG-8 and 10; the CAPMUL brands are owned by ABITEC, Columbus Ohio); propylene glycol dicaprylate; propylene glycol dicaprylate; a diethylene glycol mono ester (including 2-(2-Ethoxyethoxy)ethanol (also referred to as TRANSCUTOL®); diethylene glycol monoethyl ether; esters of saturated coconut and palm kernel oil and derivatives thereof; triglycerides of fractionated vegetable fatty acids, and combinations and derivatives thereof.

In other aspects and embodiments, progesterone is fully solubilized using, for example and without limitation, sufficient amounts of: TRANSCUTOL and MIGLYOL; TRANSCUTOL, MIGLYOL and CAPMUL PG-8 or CAPMUL PG-10; CAPMUL MCM (Medium Chain Mono- and Diglycerides); CAPMUL MCM and a non-ionic surfactant; and CAPMUL MCM and GELUCIRE.

In particular embodiments, the solubilizing agent comprises combinations of mono- and di-esters of propylene glycol or ethylene glycol or mono-, di-, and triglyceride combinations.

In certain embodiments, polyethylene glycol glyceride (GELUCIRE®, GATTEFOSSE SAS, Saint-Priest, France) can be used as the solubilizing agent or as a surfactant. For example, GELUCIRE 44/14 can be used. GELUCIRE 44/14 is a non-ionic water dispersible surfactant, also known as lauroyl macrogol-32 glycerides EP and lauroyl polyoxyl-32 glycerides NF. For example, in certain embodiments, a non-ionic surfactant is selected from one or more of glycerol and polyethylene glycol esters of long chain fatty acids, such GELUCIRE 44/14 (discussed previously herein), GELUCIRE 44/11, GELUCIRE 39/01 (glycerol esters of saturated C12-C18 fatty acids), GELUCIRE 43/01 (hard fat NF/JPE), GELUCIRE 50/13 (stearoyl macrogol-32 glycerides EP, stearoyl polyoxyl-32 glycerides NF, and stearoyl polyoxylglycerides (USA FDA IIG)). These surfactants may be used at concentrations greater than about 0.01 wt. %, and typically in various amounts of about 0.01 wt. %; about 10.0 wt. %; about 10.1 wt. %; about 20 wt. %; about 20.1 wt. %; and about 30 wt. %. More specifically, these surfactants may be used at concentrations between 0.01 wt. % to 5.00 wt. %.

Other non-ionic surfactants include, for example and without limitation one or more of oleic acid, linoleic acid, palmitic acid, and stearic acid. In other embodiments, non-ionic surfactants can comprise polyethylene sorbitol esters, such as polysorbate 80, which is commercially available under the trademark TWEEN® 80 (polysorbate 80) (Sigma Aldrich, St. Louis, MO). Polysorbate 80 comprises approximately 60%-70% oleic acid with the remainder comprising primarily linoleic acids, palmitic acids, and stearic acids. Polysorbate 80 may be used in amounts ranging from about 5 to 50% of the pharmaceutical composition by mass, and in particular embodiments, about 30% of the pharmaceutical composition total mass.

Yet another non-ionic surfactants is PEG-6 palmitostearate and ethylene glycol palmitostearate, which is available commercially as TEFOSE® 63 (GATTEFOSSE SAS, Saint-Priest, France), which can be used with, for example, CAPMUL MCM having ratios of MCM to TEFOSE 63 of, for example, 8:2 or 9:1. In other embodiments, other solubilizing agents/non-ionic surfactants combinations include, for example, MIGLYOL 812: GELUCIRE 50/13 or MIGLYOL 812: TEFOSE 63.

In still further embodiments, the surfactant can be an anionic surfactant, for example: ammonium lauryl sulfate, dioctyl sodium sulfosuccinate, perfluoro-octane sulfonic acid, potassium lauryl sulfate, or sodium stearate.

In certain embodiments, the non-ionic or anionic surfactant(s) can be used alone with at least one solubilizing agent or can be used in combination with other surfactants. Accordingly, such surfactants, or any other excipient as set forth herein, may be used to solubilize one or more APIs. In this disclosure, the API is progesterone. The combination of solubilizing agent, surfactant, and other excipients should be designed whereby the one or more APIs are delivered to the target tissue and result the intended effect of the API.

Various ratios of the noted solubilizing agents can be used for suspension or solubilization of progesterone. CAPMUL MCM and a non-ionic surfactant, e.g., GELUCIRE 44/14 (Lauroyl macrogol-32 glycerides EP Lauroyl polyoxyl-32 glycerides NF Lauroyl polyoxylglycerides (USA FDA IIG)), can be used at ratios of about 9:1, 7:3, 6:4, and 6:3 when progesterone is the sole API and at ratios of 65:35, 70:30, 75:25, 80:20, 85:15 and 90:10 with estradiol as the sole API.

Other non-limiting examples include CAPMUL MCM and GELUCIRE 44/14 used in ratios including, for example, and without limitation, 99:1 to 2:1, including, for example and without limitation: 60:40, 65:35, 70:30, 75:25, 80:10, 80:15, 85:20, 90:10, and 98:1; CAPMUL MCM and GELUCIRE 39/01 can be used in ratios including, for example and without limitation, 6:4, 7:3, and 8:2 (one or more API composition); CAPMUL MCM and GELUCIRE 43/01 can be used in ratios including, for example and without limitation, 7:3, and 8:2 (one or more API composition); and CAPMUL MCM and GELUCIRE 50/13 can be used in ratios including, for example and without limitation, 7:3, and 8:2, and 9:1. In other embodiments, CAPMUL MCM and GELUCIRE were used in ratios of up to about 65:1, e.g., 8:1, 22:1, 49:1, 65:1 and 66:1. Thus, useful ratios can be, e.g., 8:1 or greater, e.g., 60 to 70:1.

Combinations of these solubilizing agents can produce solubilized or partially solubilized progesterone, depending upon the desired unit dosage amount of progesterone. The greater the amount of progesterone per unit dosage form, the less progesterone may be solubilized. The upward limit of dosage strength per unit dose it generally limited only by the practical size of the final dosage form.

In illustrative embodiments, solubilizing agents used to suspend, partially solubilize, or fully solubilize progesterone include medium chain fatty acid esters, (e.g., esters of glycerol, ethylene glycol, polyethylene glycol, or propylene glycol) and mixtures thereof. In illustrative embodiments, the medium chain fatty acids are C6 to C14 or C6 to C12 fatty acids. In illustrative embodiments, the medium chain fatty acids are saturated, or predominantly saturated, e.g., greater than about 60% or greater than about 75% saturated. In illustrative embodiments, progesterone is soluble in the oils at room temperature, although it may be desirable to warm certain oils initially during manufacture to improve viscosity. In illustrative embodiments, the oil or oil/surfactant is liquid at between room temperature and about 50° C., e.g., at or below 50° C., at or below 40° C., or at or below 30° C. In illustrative embodiments, GELUCIRE 44/14 is heated to about 65° C. and CAPMUL MCM is heated to about 40° C. to facilitate mixing of the oil and non-ionic surfactant, although such heating is not necessary to dissolve the estradiol or progesterone.

In illustrative embodiments, the solubility of estradiol in the solubilizing agent or combination of solubilizing agents is at least about 0.5 wt %, e.g., 0.8 wt % or higher, or 1.0 wt % or higher. Illustrative examples of mono- and diglycerides of medium chain fatty acids include, among others, CAPMUL MCM, CAPMUL MCM C10 (Glyceryl Monocaprate), CAPMUL MCM C8 (Glyceryl Monocaprylate), and CAPMUL MCM C8 EP (Glyceryl Monocaprylate). These oils are C8 and C10 fatty acid mono- and diglycerides. Illustrative examples of oils that are triglycerides of medium chain fatty acids include, among others, MIGLYOL 810 and MIGLYOL 812.

Illustrative examples of solubilizing agents that are medium chain fatty acid esters of propylene glycol include, among others, CAPMUL PG-8, CAPMUL PG-2L EP/NF (Propylene Glycol Dilaurate), CAPMUL PG-8 NF (Propylene Glycol Monocaprylate), CAPMUL PG-12 EP/NF (Propylene Glycol Monolaurate) and CAPRYOL (Propylene glycol monocaprylate (type II) NF). Other illustrative examples include MIGLYOL 840 (Propylene Glycol Dicaprylate/Dicaprate).

Illustrative examples of solubilizing agents that are medium chain fatty acid esters of polyethylene glycol include, among others, GELUCIRE 44/14 (PEG-32 glyceryl laurate EP), which is polyethylene glycol glycerides composed of mono-, di- and triglycerides and mono- and diesters of polyethylene glycol. Without intending to be bound to any particular mechanism, it appears that at least in formulations comprising small amounts of GELUCIRE, e.g., 10 wt % or less, the primary function of this oil is as a non-ionic surfactant.

These illustrative examples comprise predominantly medium chain length, saturated, fatty acids, specifically predominantly C8 to C12 saturated fatty acids. In particular embodiments, the predominantly C8 to C12 saturated fatty acids comprise not less than 50 wt %, not less than 75 wt %, not less than 85 wt %, not less than 90 wt %, or not less than 95 wt % of the solubilizing agent.

It will be understood that commercially available fatty acid esters of glycerol and other glycols are often prepared from natural oils and therefore may comprise components additional to the fatty acid esters that comprise the predominant (by weight) component(s) and that therefore are used to characterize the product. Such other components may be, e.g., other fatty acid triglycerides, mono- and diesters, free glycerol, or free fatty acids. So, for example, when an oil/solubilizing agent is described herein as a saturated C8 fatty acid mono- or diester of glycerol, it will be understood that the predominant component of the oil, i.e., >50 wt % (e.g., >75 wt %, >85 wt % or >90 wt %) are caprylic monoglycerides and caprylic diglycerides. For example, the Technical Data Sheet by ABITEC for CAPMUL MCM C8 describes CAPMUL MCM C8 as being composed of mono and diglycerides of medium chain fatty acids (mainly caprylic) and describes the alkyl content as <=1% C6, >=95% C8, <=5% C10, and <=1.5% C12 and higher.

By way of further example, MIGLYOL 812 is generally described as a C8-C10 triglyceride because the fatty acid composition is at least about 80% caprylic (C8) acid and capric (C10) acid. However, it can also comprise small amounts of other fatty acids, e.g., less than about 5% of caproic (C6) acid, lauric (C12) acid, and myristic (C14) acid.

Specifically, a product information sheet for MIGLYOL by SASOL provides the composition of fatty acids as follows:

| Tests | 810 | 812 | 818 | 829 | 840 |
|---|---|---|---|---|---|
| Caproic acid (C6:0) | max. 2.0 | max. 2.0 | max. 2 | max. 2 | max. 2 |
| Caprylic acid (C8:0) | 65.0-80.0 | 50.0-65.0 | 45-65 | 45-55 | 65-80 |
| Capric acid (C10:0) | 20.0-35.0 | 30.0-45.0 | 30-45 | 30-40 | 20-35 |
| Lauric acid (C12:0) | max. 2 | max. 2 | max. 3 | max. 3 | max. 2 |
| Myristic acid (C14:0) | max. 1.0 | max. 1.0 | max. 1 | max. 1 | max. 1 |
| Linoleic acid (C18:2) | — | — | 2-5 | — | — |
| Succinic acid | — | — | — | 15-20 | — |

Where certain embodiment of this invention are described as comprising (or consisting essentially of) a capsule shell, estradiol solubilized in C8-C10 triglycerides, and a thickening agent, it will be understood that the fatty acid esters component of the formulation may be, e.g., MIGLYOL 812 or a similar product.

By way of further illustration, GELUCIRE 44/14 is generally described as lauroyl polyoxyl-32 glycerides, i.e., polyoxyethylene 32 lauric glycerides (which is a mixture of mono-, di-, and triesters of glycerol and mono- and diesters of PEGs) because the fatty acid composition is 30 to 50% lauric acid and smaller amounts of other fatty acids, e.g., up to 15% caprylic acid, up to 12% capric acid, up to 25% myristic acid, up to 25% palmitic acid, and up to 35% stearic acid. The product may also contain small amounts of non-esterified glycols.

Similarly, where certain embodiment of this invention are described as comprising (or consisting essentially of) a capsule shell, estradiol solubilized in triglycerides, and a thickening agent that is a non-ionic surfactant comprising PEG-6 stearate, ethylene glycol palmitostearate, and PEG-32 stearate, it will be understood that the thickening agent component of the formulation may be, e.g., TEFOSE 63 (PEG-6 palmitostearate and ethylene glycol palmitostearate) or a similar product.

In illustrative embodiments of the invention, the selected solubilizing agent does not require excessive heating in order to solubilize progesterone. For example, when the formulation comprises medium chain fatty acid mono- and diglycerides (e.g., CAPMUL MCM) and polyethylene glycol glycerides (e.g., GELUCIRE) as a surfactant, the oil or the surfactant can be warmed up, e.g., to about 65 C in the case of the surfactant and less in the case of the oil, to facilitate mixing of the oil and surfactant. The progesterone can be added as the mixture cools, e.g., to below about 40 C or to below about 30 C, even down to room temperature.

In various embodiments, a lubricant is used. Any suitable lubricant may be used, such as, for example and without limitation, lecithin, and in various embodiments, a mixture of polyethylene glycol ("PEG") esters, glycerides, and PEG, such as is commercially available under the trade name GELUCIRE (Gattefosse, FR) may also be used as a lubricant. Suitable lubricants may also comprise calcium stearate, ethyl oleate, ethyl laureate, glycerin, glyceryl palmitostearate, hydrogenated vegetable oil, magnesium, oxide, magnesium stearate, poloxamer, glycols, and phospholipid mixtures. In particular, a mixture of polyethylene glycol esters, glycerides, and PEG such as GELUCIRE 44/14, may be used as a lubricant. GELUCIRE 44/14 is a non-ionic water dispersible surfactant, also known as lauroyl macrogol-32 glycerides EP and lauroyl polyoxyl-32 glycerides NF. In various embodiments, GELUCIRE 44/14 acts as a suspension agent.

In various embodiments, an antioxidant is used. Any suitable antioxidant may be used, such as, for example and without limitation, butylated hydroxytoluene, also commercially referred to as BHT. Butylated hydroxytoluene, a derivative of phenol, is lipophilic and is thus suited to being intermixed with ultra-micronized progesterone and carriers disclosed or contemplated herein.

For example, in various embodiments, a pharmaceutical formulation comprises about 20% to about 80% solubilizing agent by weight, about 0.1% to about 5% lubricant by weight, and about 0.01% to about 0.1% antioxidant by weight.

In certain embodiments, the pharmaceutical composition further comprises at least one thickening agent. Generally, a thickening agent is added when the viscosity of the pharmaceutical composition provides less than desirable absorption following administration. Examples of thickening agents include: hard fats; propylene glycol; a mixture of hard fat EP/NF/JPE, glyceryl ricinoleate, ethoxylated fatty alcohols (ceteth-20, steareth-20) EP/NF (available as OVUCIRE® 3460, GATTEFOSSE, Saint-Priest, France); a mixture of hard fat EP/NF/JPE, glycerol monooleate (type 40) EP/NF (OVUCIRE WL 3264; a mixture of hard fat EP/NF/JPE, glyceryle monooleate (type 40) EP/NF (OVUCIRE WL 2944); and a mixture of various hard fats (WITEP-SOL®, Sasol Germany GmbH, Hamburg, Germany). In certain embodiments, the viscosity of pharmaceutical compositions in accordance with various embodiments may comprise from about 50 cps to about 1000 cps at 25° C. A person of ordinary skill in the art will readily understand and select from suitable thickening agents.

In other embodiments, the thickening agent is a non-ionic surfactant. For example, polyethylene glycol saturated or unsaturated fatty acid ester or diester is the non-ionic surfactant thickening agent. In some embodiments, the non-ionic surfactant comprises a polyethylene glycol long chain (C16-C20) fatty acid ester and further comprises an ethylene glycol long chain fatty acid ester, such as PEG-fatty acid esters or diesters of saturated or unsaturated C16-C18 fatty acids, e.g., oleic, lauric, palmitic, and stearic acids. In embodiments, the non-ionic surfactant comprises a polyethylene glycol long chain saturated fatty acid ester and further comprises an ethylene glycol long chain saturated fatty acid ester, such as PEG- and ethylene glycol-fatty acid esters of saturated C16-C18 fatty acids, e.g., palmitic and stearic acids. Such non-ionic surfactant can comprise PEG-6 stearate, ethylene glycol palmitostearate, and PEG-32 stearate, such as but not limited to TEFOSE 63.

In certain embodiments, the non-ionic surfactant used as a thickening agent is not hydrophilic and has good emulsion properties. An illustrative example of such surfactant is TEFOSE 63, which has a hydrophilic-lipophilic balance (HLB) value of about 9-10.

The selection and amount of hydrophilic polymer may be based on the selection and amount of solubilizing agent. The pharmaceutical composition can include a hydrophilic polymer but optionally excludes a gelling agent. In embodiments having a hydrogel, from about 5% to about 10% of the total mass may comprise the hydrophilic polymer. In further embodiments, hydrogels may be employed. A hydrogel may comprise chitosan, which swell in response to contact with water. In various embodiments, a cream pharmaceutical composition may comprise PEG-90M.

In addition to the above, the pharmaceutical compositions described herein can include one or more thermoreversible gels, typically of the hydrophilic nature including for example and without limitation, hydrophilic sucrose and other saccharide-based monomers (U.S. Pat. No. 6,018,033, which is incorporated herein by reference).

The choice of excipient will depend on factors such as, for example, the effect of the excipient on solubility and stability. Additional excipients used in various embodiments may include colorants, flavoring agents, taste-masking agents and preservatives. In certain embodiments, colorants, comprise about 0.1% to about 2% of the pharmaceutical composition by weight. In certain embodiments, preservatives in the pharmaceutical composition comprise methyl and propyl paraben, in a ratio of about 10:1, and at a proportion of about 0.005% and 0.05% by weight.

Generally, the solubilizing agents, excipients, other additives used in the pharmaceutical compositions described herein, are non-toxic, pharmaceutically acceptable, compatible with each other, and maintain stability of the pharmaceutical composition and the various components with respect to each other. Additionally, the combination of various components that comprise the pharmaceutical compositions will maintain will result in the desired therapeutic effect when administered to a subject.

The choice of excipient will, to a large extent, depend on factors such as the particular mode of administration, the effect of the excipient on solubility and stability, and the nature of the dosage form. Excipients used in various embodiments may include colorants, flavoring agents, preservatives and taste-masking agents. Colorants, for example, may comprise about 0.1% to about 2% by weight. Preservatives may comprise methyl and propyl paraben, for example, in a ratio of about 10:1, and at a proportion of about 0.005% and 0.05% by weight.

As is with all oils, solubilizers, excipients and any other additives used in the formulations described herein, each is to be non-toxic and pharmaceutically acceptable.

As referenced above, the formulations of this disclosure are generally orally administered, typically via, for example, capsules such as soft capsules.

In certain embodiments, a pharmaceutical composition of this disclosure comprises progesterone, (with about 15% or less, and in particular embodiments, about 5% or less of the progesterone being solubilized—the balance being ultra-micronized/suspended as discussed elsewhere herein), and an oil, wherein the oil is medium chain fatty acid mono- and diesters of one or more glycols, with or without surfactant.

Pharmaceutical formulations in accordance with various embodiments comprise ultra-micronized progesterone. In further embodiments, a pharmaceutical formulation comprises ultra-micronized progesterone, a carrier, and a lubricant. In still further embodiments a pharmaceutical formulation comprises ultra-micronized progesterone, a carrier, a lubricant, and optionally an antioxidant. In still further embodiments, a pharmaceutical formulation comprises ultra-micronized progesterone, and a medium chain triglyceride as a carrier. In still further embodiments, a pharmaceutical formulation comprises ultra-micronized progesterone, and mono-, di-, or triglycerides of caprylic/capric acid as a carrier. Various further embodiments also comprise lecithin and optionally butylated hydroxytoluene.

In additional embodiments, a pharmaceutical formulation comprises ultra-micronized progesterone and at least one carrier, a lubricant, optionally an antioxidant, and other pharmaceutically acceptable excipients. For example, in various embodiments, a pharmaceutical formulation comprises about 20% to about 80% carrier by weight, about 0.1% to about 5% lubricant by weight, and about 0.01% to about 0.1% antioxidant by weight.

According to embodiments, a pharmaceutical formulation comprises ultra-micronized progesterone, at least one carrier, and a non-ionic surfactant.

The choice of excipient will, to a large extent, depend on factors such as the particular mode of administration, the effect of the excipient on solubility and stability, and the nature of the dosage form. Excipients used in various embodiments may include colorants, flavoring agents, preservatives, and taste-masking agents. Colorants, for example, may comprise about 0.1% to about 2% by weight. Preservatives may comprise methyl and propyl paraben, for example, in a ratio of about 10:1, and at a proportion of about 0.005% and 0.05% by weight.

In various embodiments, ultra-micronized progesterone is administered in a capsule. Capsules may be prepared using one or more film forming polymers. Suitable film forming polymers include natural polymers, such as gelatin, and synthetic film forming polymers, such as modified celluloses. Suitable modified celluloses include, but are not limited to, hydroxypropyl methyl cellulose, methyl cellulose.

Manufacturing

In certain embodiments, the pharmaceutical composition is prepared by blending progesterone with a pharmaceutically acceptable solubilizing agent, including for example and without limitation, at least one medium chain fatty acid such as medium chain fatty acids consisting of at least one mono-, di-, or triglyceride, or derivatives thereof, or combinations thereof. In particular embodiments, the pharmaceutical composition also comprises at least one glycol or derivatives thereof or combinations thereof or combinations of at least one glyceride and glycol. The glycol(s) may be used as solubilizing agents or to adjust viscosity and, thus, may be considered thickening agents. Other excipients can optionally be included, including, for example and without limitation, anti-oxidants, lubricants, and the like. In some embodiments, the pharmaceutical composition includes sufficient solubilizing agent(s) to fully solubilize the progesterone. It is expressly understood, however, that other volumes of solubilizing agent can be used depending on the level of progesterone solubilization desired. Persons of ordinary skill in the art will know and understand how to determine the volume of solubilizing agent and other excipients depending on the desired percent of progesterone to be solubilized in the pharmaceutical composition.

In illustrative embodiments, GELUCIRE 44/14 (lauroyl macrogol-32 glycerides EP, lauroyl polyoxyl-32 glycerides NF, lauroyl polyoxylglycerides (USA FDA IIG)) is heated to about 45-65° C. and CAPMUL MCM or MIGLYOL 812 is heated to about 40° C. to facilitate mixing of the oil and non-ionic surfactant, although such heating is not necessary to dissolve the progesterone.

Specific Examples disclosed herein provide additional principles and embodiments illustrating processes for manufacturing the pharmaceutical compositions disclosed herein.

Delivery Vehicle

The pharmaceutical compositions described herein can be delivered orally inside of a delivery vehicle, for example a capsule. In certain embodiments, the capsules are soft capsules made of materials well known in the pharmaceutical arts such as gelatin. In other embodiments, the delivery vehicle is integral with the pharmaceutical composition (i.e., the pharmaceutical composition is the delivery vehicle). Hard or soft shell capsules can be used to administer the API. In certain embodiments, capsules may be prepared by forming the two capsule halves, filling one of the halves with a fill solution, and then sealing the capsule halves together to form the finished capsule.

Hard shell capsules may be prepared by combining the "Body" and the "Cap". The "Body" of the capsule is filled with the "fill mass" and then closed with the "Cap". The "Body"/"Cap" interface is then sealed/banded.

Soft gelatin ("softgel") capsules may be prepared using a rotary die encapsulation process, as further described below. Softgel capsules may contain the formulation disclosed herein as a "fill material." The soft gelatin capsule do not contain one or more of the following as the fill material: hydrophilic gel-forming bioadhesive (e.g., mucoadhesive) agents; a lipophilic agent and a gelling agent for the lipophilic agent, or a hydrodispersible agent. In some embodiments, the hydrophilic gel-forming bioadhesive agent is carboxyvinylic acid; hydroxypropylcellulose; carboxymethylcellulose; gelatin; xanthane gum; guar gum; aluminum silicate; or mixtures thereof. In still other embodiments, the lipophilic agent is a liquid triglyceride; solid triglyceride (e.g., with a melting point of about 35° C.); carnauba wax; cocoa butter; or a mixture thereof. In certain embodiments, the gelling agent is a hydrophobic colloidal silica. And in still other embodiments, the hydrodispersible agent can be polyoxyethylene glycol; polyoxyethylene glycol 7-glycerylcocoate; or a mixture thereof.

The softgel capsule itself may comprise a gelatin material in a relatively solid or stiff form. The gel capsule defines an inner volume that contains the fill material. Dissolution of the gelatin material may commence at various points after administration, such as in the digestive tract (mouth, esophagus, stomach and intestines), or in another body cavity, such as the vaginal tract.

Gel capsules may be prepared using one or more film forming polymers. Suitable film forming polymers include, but are not limited to, natural polymers, such as gelatin, and synthetic film forming polymers, such as modified celluloses. Suitable modified celluloses include, but are not limited to, hydroxypropyl methyl cellulose, methyl cellulose.

Suitable shell additives, for either a hard or soft shell capsules, may include plasticizers, opacifiers, colorants, humectants, preservatives, flavorings, and buffering salts and acids, and combinations thereof. The main ingredients of the capsule shell is primarily gelatin (or a gelatin substitute for non-gelatin capsules), plasticizer, and purified water. Hard shell and soft shell capsules differ primarily in the amount of plasticizer present that is used in the capsule shell.

Plasticizers are chemical agents added to gelatin to make the material softer and more flexible. Suitable plasticizers include, but are not limited to, glycerin, sorbitol solutions which are mixtures of sorbitol and sorbitan, and other polyhydric alcohols such as propylene glycol and maltitol or combinations thereof.

Opacifiers are used to opacify the capsule shell when the encapsulated active agents are light-sensitive. Suitable opacifiers include titanium dioxide, zinc oxide, calcium carbonate and combinations thereof.

Colorants can be used for marketing and product identification/differentiation purposes. Suitable colorants include synthetic and natural dyes and combinations thereof.

Flavorings can be used to mask unpleasant odors and tastes of fill formulations. Suitable flavorings include synthetic and natural flavorings. The use of flavorings can be problematic due to the presence of aldehydes which can cross-link gelatin. As a result, buffering salts and acids can be used in conjunction with flavorings that contain aldehydes in order to minimize cross-linking of the gelatin.

In accordance with various embodiments, a softgel dosage form is used.

As the softgel dissolves, the inner volume may come into fluid communication with the digestive system, allowing the fill material to leach outside the softgel. A softgel may also be punctured, cut, or otherwise opened outside a body. The fill material may then be poured or squeezed outside the gel capsule and applied on or in the body, such as within the vaginal cavity.

Humectants can be used to suppress the water activity of the softgel. Suitable humectants include glycerin, sorbitol, propylene glycol, microcrystalline cellulose, silica, mineral oil, and combinations thereof which are often components of the plasticizer composition. Regulated water activity in pharmaceutical compositions and dosage forms, such as capsules, can improve the compatibility and stability of the compositions and forms. This is because when hydrolosis is regulated chemical degradation caused by water is also regulated (or slowed, as is desirable in the present case). Thus, by regulating water in the present compositions, the capsule shells are less likely to soften, dissolve, break, or leak during storage. Moreover, due to the low water activity of dried, properly stored softgels, the greatest risk from microorganisms comes from molds and yeasts. For this reason, preservatives can be incorporated into the capsule shell. Suitable preservatives include alkyl esters of p-hydroxy benzoic acid such as methyl, ethyl, propyl, butyl and heptyl esters (collectively known as "parabens") or combinations thereof.

The fill material may comprise a liquid, such as an oil, a solution, a suspension, or other acceptable forms. The active ingredient or active ingredient may be contained within the liquid.

Hard and softgel capsules can be manufactured according to various techniques known in the art. In particular embodiments, softgel capsules can be prepare using a rotary die encapsulation process. An exemplary process is disclosed in Wilkinson, P. K. et al., 1990, "Softgels: manufacturing considerations." In: Specialized Drug Delivery Systems, P. Tyle (Ed.), pp. 409-449, Marcel Dekker, Inc., New York, the entirety of which is hereby incorporated by reference.

In other embodiments, softgels can be prepared according to the process disclosed in PCT/US2000/005178, the entirety of which is incorporated herein by reference.

Hard shell capsules can also be used as the delivery vehicle. These capsules may be prepared by forming the two capsule halves, filling one half with the fill material, and then sealing the halves together to form the finished capsule. In other embodiments, hard shell capsules may be prepared by combining a "body" and a "cap." The "body" of the capsule is filled with the fill material and then closed with the cap. The body/cap interface is then sealed or banded.

Drawings

Figure 2:
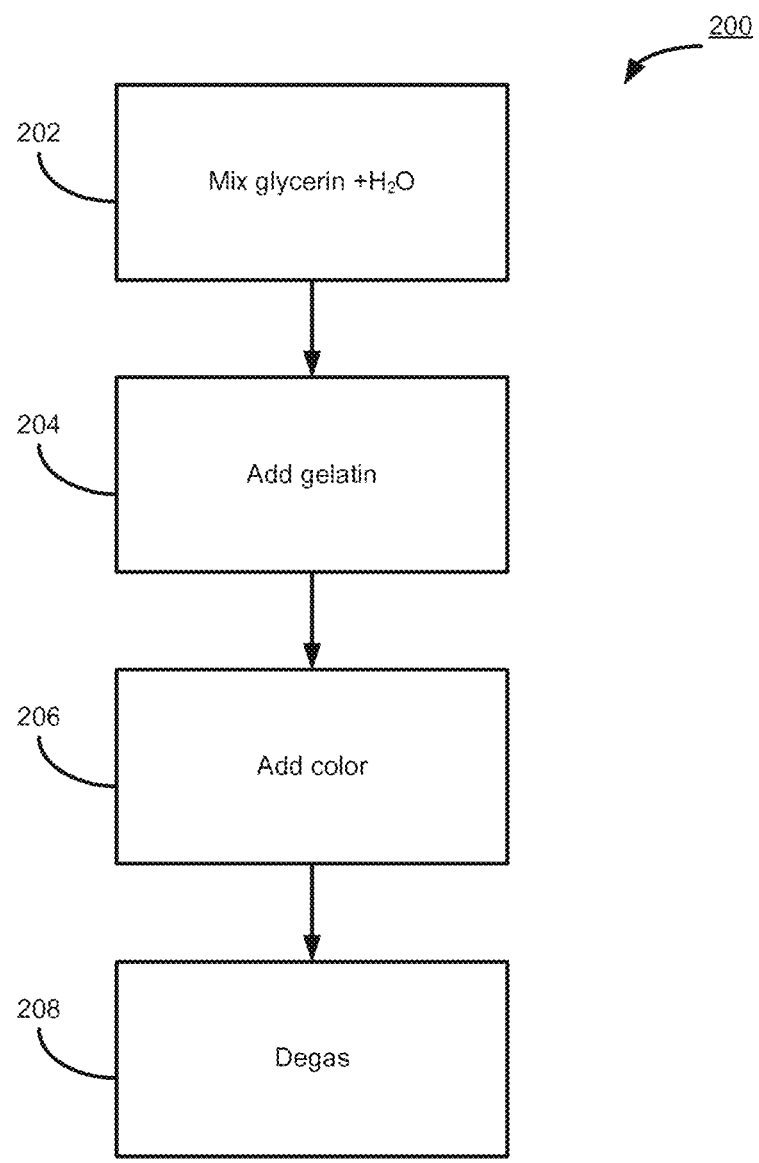
FIG. 2 illustrates a process to produce softgel capsules in accordance with various embodiments.
Figure 3:
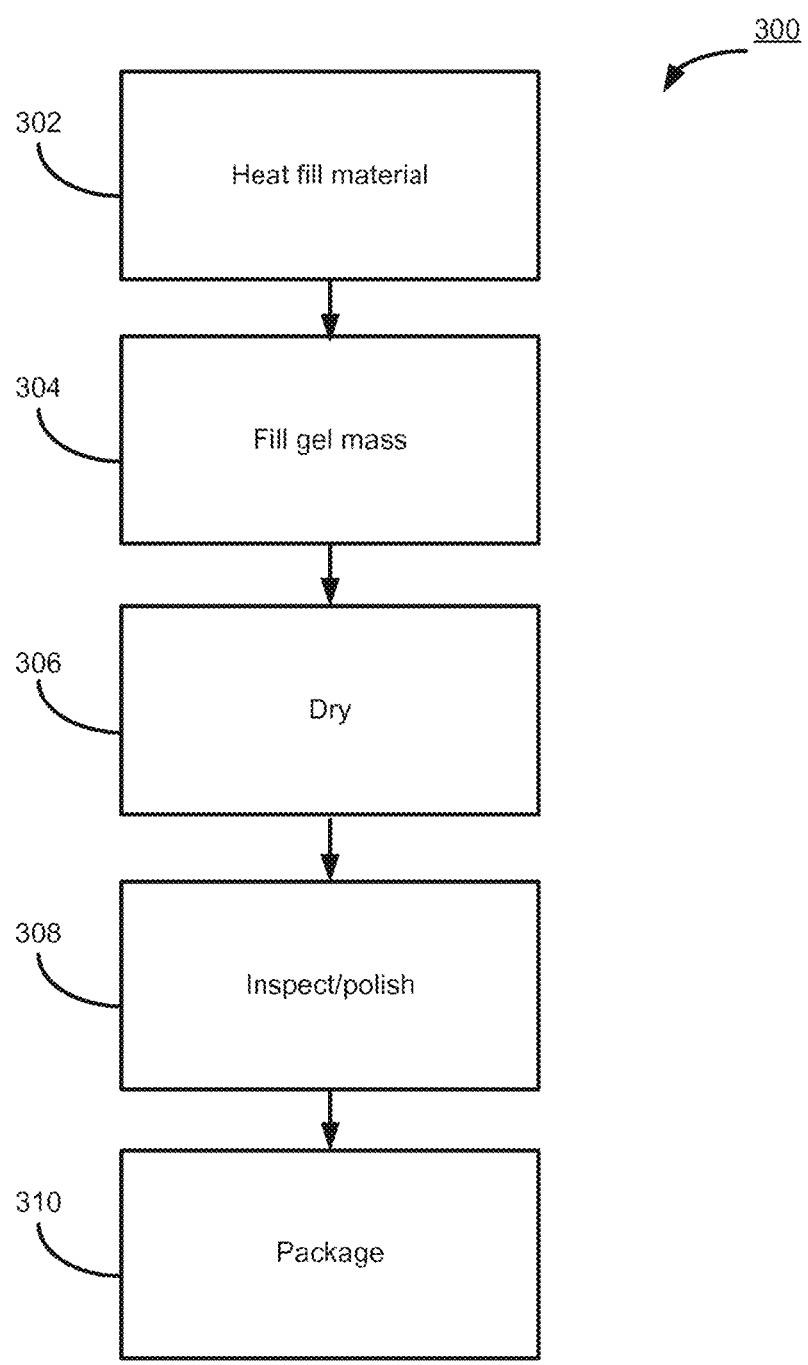
FIG. 3 illustrates a process to produce softgel capsules in accordance with various embodiments.

Methods of manufacture in accordance with various embodiments are shown in FIGS. 1-3. With reference to FIG. 1, method of fill material, i.e. fill mass, preparation 100 is shown. Operation 102 comprises mixing a solubilizing agent, a surfactant (i.e. lubricant), and an antioxidant as described herein. For example, lecithin and butylated hydroxytoluene may be mixed with one or more medium chain mono-, di- or triglycerides, or combinations thereof. Mixing may be facilitated by an impellor, agitator, or other suitable means. Operation 102 may be performed under an inert or relatively inert gas atmosphere, such as nitrogen gas $N_2$. Mixing may be performed in any suitable vessel, such as a stainless steel vessel.

Operation 104 may comprise mixing progesterone (progesterone) into the mixture of the solubilizing agent, the surfactant (i.e. lubricant), and the antioxidant. A pasty substance is thus formed. Mixing may occur in a steel tank or vat. Mixing may be facilitated by an impellor, agitator, or other suitable means. Operation 104 may be performed under an inert or relatively inert gas atmosphere, such as nitrogen gas $N_2$. Operation 106 comprises degasing. The resulting mixture from operation 106 may comprise a pharmaceutical composition suitable for production into a softgel capsule.

With reference to FIG. 2, softgel capsule, i.e., gel mass, production 200 is shown. Operation 202 comprises mixing glyercin with water. The water used in operation 202 may be purified by any suitable means, such as reverse osmosis, ozonation, filtration (e.g., through a carbon column) or the like. Mixing may be facilitated by an impellor, agitator, or other suitable means. Operation 202 may be performed under an inert or relatively inert gas atmosphere, such as nitrogen gas $N_2$. Heating may be performed until the temperature reaches 80°±5° C.

Operation 204 comprises the addition of gelatin to the glycerin water mixture. Mixing may be facilitated by an impellor, agitator, or other suitable means. Operation 204 may be performed under an inert or relatively inert gas atmosphere, such as nitrogen gas $N_2$. A vacuum may be drawn in operation 204 to de-aerate.

Operation 206 comprises addition of an excipient (i.e. coloring agent) such as a dye. A coloring agent may comprise products sold under the trademark OPATINT or the suitable agent. Operation 206 may be performed under an inert or relatively inert gas atmosphere, such as nitrogen gas $N_2$. Operation 208 comprises degasing. The resulting mixture from operation 208 may comprise a gel capsule material suitable for use as a gel capsule in production of a softgel capsule.

With reference to FIG. 3, softgel capsule assembly process 300 is shown. Operation 302 comprises heating the fill material. The pharmaceutical composition may be heated to any suitable temperature. In various embodiments, the pharmaceutical composition is heated to 30° C.+/−3° C. pharmaceutical composition maybe heated in a fill hopper. A fill hopper may comprise a device configured to hold a volume of the pharmaceutical composition or to dispense the pharmaceutical composition in controlled volumes.

Operation 304 comprises filling a gel mass. A gel mass may be taken from the gel capsule material produced in operation 208 of FIG. 2. Filling may be performed by injecting, placing, or otherwise disposing the pharmaceutical composition within a volume defined by the gel capsule material. The filling may occur in an encapsulator. The spreader boxes may be a temperature of 55° C.+/−10° C. The wedge temperature may be 38° C.+/−3° C. The drum cooling temperature may be 4° C.+/−2° C. The encapsulator may be lubricated using MIGLYOL 812. Operation 304 thus produces one or more softgel capsules. Filling may comprise producing a ribbon of thickness 0.85±0.05 mm using spreader box knobs. The pharmaceutical composition may be injected into the gel to produce a fill weight having target weight ±5% (i.e., 650±33 mg and 325±16.3 mg).

Operation 306 comprises drying the softgel capsules. Drying may be performed in a tumble dryer, tray dryer, or combinations thereof. For example, drying may be performed in a tumble drying basket for between about 10 minutes and about 120 minutes. Drying may continue in a drying room for about 24 hours to about 72 hours. Polishing may be performed with isopropyl alcohol.

Design Factors for Encapsulated Pharmaceutical Compositions

In certain embodiments, the pharmaceutical composition is designed to maximize API solubility, and other favorable characteristics without sacrificing efficacy, while simultaneously improving bioavailability in subjects. Other favorable characteristics, besides improving bioavailability as compared to the RLD, include, for example, bioavailability that is bioequivalent to the RLD, improved subject compliance (i.e., ability to easily take the right capsule during the correct period), reducing food and allergy effects due to administration, and reducing required prescribed dosage levels in order to achieve efficacy of the drug product.

In some embodiments, progesterone is fully or partially solubilized. The form of the API (i.e., being in solution), and other factors and conditions, may account for the increased bioavailabilty of progesterone as compared to the RLD.

In some embodiments, the pharmaceutical composition is delivered via a gelatin capsule delivery vehicle. In these embodiments, the pharmaceutical composition is a liquid pharmaceutical composition. Accordingly, the pharmaceutical composition of such embodiments is encapsulated in the gelatin capsule. The inclusion of the capsules in blister packs, as described elsewhere herein, ensures that subjects will receive the right dosage during the correct period of time.

In some embodiments, the gelatin capsules are softgels. Other forms of administration (i.e. injection, intra-muscular, etc.) can cause pain, discomfort, or irritation, especially when frequent administration is required. Softgels eliminate these problems, while minimizing adverse tastes. Softgels can be administered orally or can be administered locally. In some embodiments, the softgel is administered orally.

Through extensive experimentation, various medium chain fatty acid esters of glycerol and propylene glycol demonstrated one or more favorable characteristics for development as a human drug product. In one embodiment, the solubilizing agent was selected from at least one of a solvent or co-solvent. Suitable solvents and co-solvents include any mono-, di-, or triglyceride and glycols, and combinations thereof.

In other embodiments, the solubilizing agent was selected from one or more C6 to C12 fatty acid mono-, di-, or triesters of glycerol, e.g., one or more C6 to C14 triglycerides, e.g., one or more C6 to C12 triglycerides, such as one or more C8-C10 triglycerides. Thus, in certain embodiments, the pharmaceutical composition comprises progesterone that is at least about 75% solubilized in a solubilizing agent comprising one or more C6 to C14 medium chain fatty acid mono-, di-, or triglycericdes and, optionally, a thickening agent.

In still other embodiments, the pharmaceutical composition comprises progesterone that is at least about 75% solubilized one or more C6 to C12 medium chain fatty acid mono-, di-, or triglycerides, e.g., one or more C6 to C14 triglycerides, e.g., one or more C6 to C12 triglycerides, such as one or more C8-C10 triglycerides. These embodiments specifically contemplate the progesterone being at least 85% solubilized, at least 90% solubilized, at least 95% solubilized, and in certain instances, 100% solubilized. In other embodiments, estradiol or a combination of progesterone and estradiol is included in the pharmaceutical compositions as the one or more APIs.

As noted previously herein, liquid pharmaceutical compositions are preferably liquid at room temperature. Accordingly, gels, hard fats, or other solid forms that are not liquid at room or body temperature are less desirable in embodiments of the pharmaceutical composition that are liquid. In certain embodiments, where a non-ionic surfactant such as GELUCIRE or TEFOSE to increase viscosity, the non-ionic surfactant may be solid at room temperature. In those situations, the non-ionic surfactant may require melting to mix with one or more APIs solubilized in a fatty acid-glycol ester. In this embodiment, the resultant composition is advantageously liquid, not solid. However, in these embodiments, the resultant pharmaceutical composition remains liquid, albeit with greater viscosity, although it is still not a solid.

In other embodiments, the pharmaceutical composition comprises progesterone, a medium chain solubilizing agent, and a thickening agent as the only essential ingredients delivered via a softgel delivery vehicle. Non-essential ingredients, e.g., colorants, antioxidants, preservatives, or other excipients may be included as well. Other embodiments comprise one or more APIs.

Additional ingredients can be incorporated in amounts that do not materially change the solubility of the progesterone, the pharmacokinetics of the pharmaceutical composition, or the efficacy of the pharmaceutical composition. Other factors that should be considered when adjusting the ingredients of the pharmaceutical composition include taste, water regulation, and other relevant factors, for example those that would lead to reduced patient compliance.

In softgel embodiments, mucoadhesive agents, gelling agents, dispersing agents, or the like would not be included because of effects some of these ingredients may have on bioavailability of the API(s) in the digestive system.

Methods

Pharmaceutical compositions in different embodiments may be administered alone or combination with one or more other drugs (or as any combination thereof). For example, compositions in accordance with embodiments including one or more other drugs may also comprise estradiol. In such compositions, estradiol is also an API.

In certain embodiments, and as discussed elsewhere herein, the pharmaceutical composition disclosed herein can be administered orally in a softgel. As the softgel dissolves after administration, the inner volume may come into fluid communication with the digestive system such that the progesterone present in the pharmaceutical composition can be absorbed systemically. Oral administration may involve swallowing, so that the pharmaceutical composition enters the gastrointestinal tract. Alternatively, buccal or sublingual administration may be employed such that the pharmaceutical composition enters the bloodstream directly from the mouth.

In embodiments where hard shell capsules are employed, the method of administration is typically oral. Hard capsules or softgels may be arranged in blisters or cartridges or bottles.

In certain embodiments, a 28-day or monthly regimen of capsules can be packaged in a single kit (e.g., a blister pack) having delivery days identified to improve subject compliance. One or more of the capsules may contain no progesterone. A blister pack can have a plurality of scores or perforations separating blister pack into 28 days. Each day may further comprise a single blister or a plurality of blisters. In various embodiments, each dose (e.g., each softgel) may contain solubilized, partially solubilized, or partially suspended progesterone in any of the amounts previously set forth herein, though may, in certain instances, include 100, 150, or 200 mg of progesterone. In addition, kits having other configurations are also contemplated herein. For example, without limitation, kits having such blister packs may contain any number of capsules.

In additional embodiments, progesterone is formulated for intraperitoneal, percutaneous, subcutaneous, intra-muscular, and atomization administration (i.e. such as with nasal mist administration).

In still other embodiments, the pharmaceutical compositions are administered according to other techniques known to those skilled in the art, which may include, but are not limited to: tablets, film-coated tablets, prolonged-release tablets, modified-released tablets, effervescent tablets, orodispersible tablets, sachets, dry powders used to form suspension; or liquid dosage forms.

Compositions in accordance with the various embodiments disclosed herein may be used to treat or prevent endometrial hyperplasia, prevent secondary amenorrhea, or mitigate or treat the effects of estradiol supplementation. In certain embodiments, compositions comprising progesterone may be co-administered with estradiol or co-formulated with estradiol.

In other embodiments, formulations in accordance with various embodiments may be used to treat or prevent preterm delivery in pregnant women, including in certain women having a shortened cervix. In various embodiments, a capsule, for example a softgel capsule, may be opened and the fill material applied in or around the vagina. However, in various embodiments the capsules are taken orally.

In still further embodiments, formulations in accordance with various embodiments may be used to treat menopause-related symptoms, including vasomotor symptoms, for example, in relation to treatment of hypoestrogenism related symptoms including hot flashes and night sweats (vasomotor symptoms), sleep disturbances, mood changes, vulvovaginal atrophy; and osteoporosis and endometrial hyperplasia reduction.

In still further embodiments, formulation in accordance with various embodiments may be used to treat amenorrhea.

Additional objects of this disclosure include: providing increased patient compliance secondary to ease of use; providing increased physician adoption secondary to ease of use/instruction with less worry of side effects from inappropriate usage; providing decreased side-effects from erroneous use (decreased irregular bleeding); providing better efficacy/control of symptoms secondary to appropriate use; reducing the metabolic and vascular side effects of the commonly used synthetic progestins when administered alone or in combination with an estrogen (norethindrone acetate, medroxyprogesterone acetate, etc.) including, for example, stroke, heart attacks, blood clots and breast cancer.

Enhanced Bioavailability

In certain embodiments, the formulations disclosed herein provide enhanced bioavailability of progesterone when compared to conventional progesterone formulations. As a result of this improved bioavailability, certain embodiments of the formulations disclosed herein allow for a reduction in the quantity of progesterone administered to a person in need thereof while still providing the providing the benefits of a dosage form containing the greater amount of progesterone.

As such, and in certain embodiments, a formulation of this disclosure can include less than 200 mg of progesterone while still having an acceptable PK profile. In particular, embodiments, the formulation can include about 175 mg of progesterone, about 170 mg of progesterone, about 165 mg of progesterone, about 160 mg of progesterone, about 159 mg of progesterone, about 158 mg of progesterone, about 157 mg of progesterone, about 156 mg of progesterone, about 155 mg of progesterone, about 154 mg of progesterone, about 153 mg of progesterone, about 152 mg of progesterone, about 151 mg of progesterone, about 150 mg of progesterone, about 149 mg of progesterone, about 148 mg of progesterone, about 147 mg of progesterone, about 146 mg of progesterone, about 145 mg of progesterone, about 170 mg of progesterone, about 140 mg of progesterone, about 135 mg of progesterone, about 170 mg of progesterone, about 130 mg of progesterone, about 125 mg of progesterone, about 120 mg of progesterone, about 115 mg of progesterone, about 110 mg of progesterone, about 105 mg of progesterone, or about 100 mg of progesterone. In still further embodiments, the formulation can have exactly the amounts of progesterone noted above, e.g. exactly 175 mg of progesterone, exactly 170 mg of progesterone, etc.

In certain embodiments, this disclosure provides a formulation including less than 200 mg of progesterone having an $AUC_{0-\infty}$ in (ng/ml)*hr of from about 5 to about 500, from about 5 to about 400, from about 5 to about 300, from about 5 to about 270, from about 20 to about 200, from about 25 to about 150, or from about 25 to about 140. In particular embodiments, the formulation including less than 200 mg progesterone can have an $AUC_{0-\infty}$ of about 137 (ng/ml)*hr±95%. In particular embodiments, the formulation can have about 150 or exactly 150 mg progesterone.

In certain embodiments, this disclosure provides a formulation including less than 200 mg of progesterone having an $AUC_{0-t}$ in (ng/ml)*hr of from about 5 to about 500, from about 5 to about 400, from about 5 to about 300, from about 5 to about 240, from about 20 to about 200, from about 25 to about 150, or from about 25 to about 140. In particular embodiments, the formulation including less than 200 mg progesterone can have an $AUC_{0-t}$ of about 120 (ng/ml)*hr±95%. In particular embodiments, the formulation can have about 150 or exactly 150 mg progesterone.

In certain embodiments, this disclosure provides a formulation including less than 200 mg of progesterone having a $C_{max}$ in ng/ml of from about 3 to about 350, from about 3 to about 325, from about 3 to about 300, from about 3 to about 250, from about 3 to about 240, and from about 3 to about 230. In particular embodiments, the formulation including less than 200 mg progesterone can have a C. of about 75 ng/ml±95%. In particular embodiments, the formulation can have about 150 or exactly 150 mg progesterone.

Although the amount of progesterone is typically less than 200 mg, in certain embodiments, the amount of progesterone can be about 300 mg. In such embodiments, the formulation can have the PK parameters discussed below upon administration.

In certain embodiments, this disclosure provides a formulation including about 300 mg of progesterone having an $AUC_{0-\infty}$ in (ng/ml)*hr of from about 10 to about 1000, from about 10 to about 800, from about 10 to about 600, from about 10 to about 540, from about 40 to about 400, from about 50 to about 300, or from about 50 to about 280. In particular embodiments, the formulation including about 300 mg progesterone can have an $AUC_{0-\infty}$ of about 274 (ng/ml)*hr±95%.

In certain embodiments, this disclosure provides a formulation including about 300 mg of progesterone having an $AUC_{0-t}$ in (ng/ml)*hr of from about 10 to about 1000, from about 10 to about 800, from about 10 to about 600, from about 10 to about 480, from about 40 to about 400, from about 50 to about 300, or from about 50 to about 280. In particular embodiments, the formulation including about 300 mg progesterone can have an $AUC_{0-t}$ of about 240 (ng/ml)*hr±95%.

In certain embodiments, this disclosure provides a formulation including about 300 mg of progesterone having a $C_{max}$ in ng/ml of from about 6 to about 700, from about 6 to about 650, from about 6 to about 600, from about 6 to about 500, from about 6 to about 480, and from about 6 to about 460. In particular embodiments, the formulation including about 300 mg progesterone can have a C. of about 150 ng/ml±95%.

Bioavailability comparisons to commercially available forms, such as tablet forms, may be determined by standard pharmacokinetic techniques.

In accordance with various embodiments, food effects are reduced, e.g., relative to comparative progesterone products.

In accordance with various embodiments, formulations do not include peanut oil. The lack of peanut oil obviates the risk posed to those having peanut-based allergies.

Measurement of Efficacy

Efficacy can be measured using standard techniques known in the art. However in certain embodiments, subjects are administered progesterone. After administration of the progesterone, endometrial biopsies can be performed by a board-certified gynecologist. Procedures, instruments used, and observations are documented in the subject's file.

The resulting biopsy specimens can then processed by a central laboratory. The central laboratory includes a chartered pathology committee of independent pathologists who are experts in the field of endometrial pathology to assess all endometrial biopsy sample.

In certain embodiments, treatment with the pharmaceutical compositions described herein resulted in complete and partial secretory activity. In cases of complete secretory activity, subjects experienced 1) glands with secretory changes, and 2) stromal predecidual changes. In cases of partial secretory activity, subjects experienced 1) glands with secretory changes, or 2) stromal predecidual changes.

In certain embodiments, subjects are administered pharmaceutical compositions as described herein, while other subjects are administered placebos. Exemplary test scenarios are described in the Example section, below. In these embodiments, secretory activity is measured as a proportion of subjects at Cycle 3 Day 24±1 day on active treatment (200 mg progesterone/day, 225 mg progesterone/day, or 300 mg progesterone/day) compared to placebo with complete secretory activity on endometrial biopsy (referenced in the examples as the "primary efficacy endpoint").

In these embodiments, secretory activity is also measured as a proportion of subjects at Cycle 3 Day 24±1 day on active treatment (200 mg progesterone/day, 225 mg progesterone/day, or 300 mg progesterone/day) compared to placebo with total secretory activity (defined as the aggregate of partial and complete secretory activity) on endometrial biopsy. Included in this measurement is an observation of the proportion of subjects reporting withdrawal bleeding at cycle 2 on or after cycle day 21 or within 7 days (including 7th day) after completion of blinded treatment at cycle 2 (this and the secretory measurement of the preceding sentence are referenced in the examples as the "secondary efficacy endpoints").

Statistical Measurements

Pharmacokinetics of the pharmaceutical composition disclosed herein can be calculated using statistical analyses. In particular embodiments, Analysis of Variance ("ANOVA") or Analysis of CoVariance ("ANCOVA") are used to evaluate differences between a subject receiving treatment with a pharmaceutical composition comprising an active pharmaceutical composition (for example, a pharmaceutical composition comprising progesterone) and a subject receiving treatment with a placebo (for example, the same pharmaceutical composition but without progesterone) or a reference drug. A person of ordinary skill in the art will understand how to perform statistical analysis of the data collected.

Among the data collected or calculated are PK parameters for pharmacokinetic evaluation and analysis, including, but not limited to, AUC, $C_{max}$, and $T_{max}$. The pharmacokinetic evaluation was carried out by a research lab using statistical and analytical software, which could include, but is not limited to, WinNonlin® software (version 5.3), and using SAS version 9.2.

SPECIFIC EMBODIMENTS

Through extensive trial-and-error testing of various fatty acid esters of glycerol and other glycols, embodiments of the invention have been invented that have one or more favorable characteristics for development as a human drug product. Such favorable characteristics include those described above, e.g., improved PK properties and reduced inter- and intra-patient variability.

Such embodiments include an encapsulated liquid pharmaceutical formulation for orally administering progesterone to a mammal in need thereof, said formulation comprising: progesterone, as the sole active pharmaceutical ingredient, in ultra-micronized form suspended in a carrier that comprises a medium chain fatty acid-glycol ester or mixtures thereof and a non-ionic surfactant comprising a polyethylene glycol fatty acid ester.

In particular embodiments, the progesterone can be ultra-micronized.

In certain embodiments, the progesterone is suspended or solubilized in one or more solubilizing agents such as one or more C6 to C14 fatty acid mono-, di-, or triesters of glycerol, including, but not limited to, one or more C6 to C14 triglycerides, one or more C6 to C12 triglycerides, or one or more C8-C10 triglycerides, as well as combinations thereof. An example of a solubilizing agent that provides beneficial properties is MIGLYOL, and in particular MIGLYOL 812.

In such general and more specific embodiments, the non-ionic surfactant is a polyethylene glycol saturated or unsaturated fatty acid ester or diester. In certain such embodiments, the non-ionic surfactant comprises C8 to C18 fatty acid esters of glycerol and polyethylene glycol. An example of a non-ionic surfactant that provides beneficial properties is GELUCIRE, e.g., GELUCIRE 44/14.

In certain such embodiments, the non-ionic surfactant has a HLB value of about 15. An illustrative example of such surfactant is GELUCIRE 44/14.

EXAMPLES

The formulations and methods described herein are now further detailed with reference to the following examples. These examples are provided for the purpose of illustration only and the formulations and methods described herein should in no way be construed as being limited to these examples. Rather, the formulations disclosed herein should be construed to encompass any and all variations which become evident as a result of the teaching provided herein.

Example 1

In an exemplary embodiment, a capsule is provided containing a fill material comprising a formulation set forth in one of Tables 2, 2A, or 2B

TABLE 2

| Ingredient | mg/Capsule | % | Function |
| --- | --- | --- | --- |
| Ultra-micronized Progesterone | 200.00 | 30.77 | Active |
| Medium Chain Triglyceride (MIGLYOL 812 or equivalent) | qs | qs | Solubilizing Agent |
| Lecithin Liquid | 1.63 | 0.25 | Lubricant/ Emulsifier |
| Butylated Hydroxytoluene (also referred to as "BHT") | 0.13 | 0.02 | Antioxidant |

TABLE 2A

| Ingredient | mg/Capsule | % | Function |
| --- | --- | --- | --- |
| Progesterone | 150 | 33.3 | Active |
| Medium Chain Triglyceride (MIGLYOL 812 or equivalent) | 292.3 | 65.0 | Solubilizing Agent |

TABLE 2A-continued

| Ingredient | mg/Capsule | % | Function |
|---|---|---|---|
| Lauroyl polyoxyl-32-glycerides (GELUCIRE 44/14 or equivalent) | 7.7 | 1.7 | Lubricant/Emulsifier |

TABLE 2B

| Ingredient | mg/Capsule | % | Function |
|---|---|---|---|
| Progesterone | 75 | 33.3 | Active |
| Medium Chain Triglyceride (MIGLYOL 812 or equivalent) | 146.2 | 65.0 | Solubilizing Agent |
| Lauroyl polyoxyl-32-glycerides (GELUCIRE 44/14 or equivalent) | 3.8 | 1.7 | Lubricant/Emulsifier |

The formulation in Table 2 is prepared as follows: MIGLYOL is heated to about 45° C. GELUCIRE 44/14 is added and mixed until dissolved. BHT is added and mixed until dissolved. Progesterone is suspended and passed through a colloid mill. The resultant fill mass can be used for encapsulation.

The formulations in Tables 2A and 2B are prepared as follows: melt Gelucire 44/14 by heating it to about 45-50° C.; once Gelucire 44/14 is completely melted, add MIGYOL 812 and mix/stir until dissolved; continue mixing/stirring; during the mixing/stirring, slowly add progesterone to the solution; and, after all progesterone has been added, continue mixing for a period of time to ensure proper suspension and near dissolution equilibrium. The suspended progesterone is then passed through a colloid mill. De-gassing and applying a vacuum for complete de-aeration of the fill mass is conducted. The resultant fill mass can be used for encapsulation.

Example 2

In an exemplary embodiment, a capsule is provided containing a fill material comprising:

TABLE 3

| Ingredient | % | mg/Capsule | Function |
|---|---|---|---|
| Ultra-micronized Progesterone | 30.77 | 200.00 | Active |
| Medium Chain Triglyceride (MIGLYOL 812 or equivalent) | 65.93 | 428.55 | Solubilizing Agent |
| Lauroyl polyoxyl-32-glycerides (GELUCIRE 44/14 or equivalent) | 3.00 | 19.50 | Suspending Agent |
| Butylated Hydroxytoluene | 0.03 | 1.95 | Antioxidant |
| Total | 100 | 650 | |

In various embodiments, amounts of MIGLYOL may be present in a range from about 35-95% by weight; GELUCIRE 44/14 from about 0.5-30% by weight; and BHT from about 0.01-0.1% by weight.

Example 3

Progesterone Solubility

In various embodiments, both estradiol and progesterone may be independently dissolved in a solubilizing agent. In various embodiments, the solubility of both estradiol and progesterone will be such that a therapeutically effective dose may be obtained in a reasonably sized mass, generally considered to be between 1 mg and 1200 mg, preferably suitable for encapsulation in a size 3 to 22 oval or oblong capsule. For example, in various embodiments, 50 mg to 100 mg of progesterone may be dissolved in a volume of solubilizing agent; i.e., the solubility would be 50 mg to 100 mg per capsule.

MIGLYOL was attempted, and while it can be considered a good carrier for progesterone, it alone did not provide a desirable level of solubilization of estradiol (e.g., solubility of 12 mg/g may be desirable in various embodiments). Thus, MIGLYOL, including without limitation MIGLYOL 812, may be used in embodiments comprising fully solubilized, partially solubilized, and suspended progesterone.

As can be seen in Table 4, the solubility of progesterone in CAPMUL MCM is ~73 mg/g. Therefore, by suspending 200 mg progesterone in 400 mg of solvent, part of the dose (~14%) is already dissolved and the remaining is still a suspension. In some aspects and embodiments, it is desired to minimize the partial solubility of progesterone in the formulation in order to minimize the possibility of recrystallization. Based on 73 mg/g solubility, the capsule size required to make a capsule of 50 mg solubilized progesterone would be 685 mg. Based on 95 mg/g solubility, a 50 mg progesterone capsule would require a 526 capsule size. The other capsule sizes required based on each respective solubility below includes: 1,799 mg, 579 mg, 709 mg, and 871 mg. Capsule size amounts based on respective solubilities will generally be at least 10% greater than the calculated value in order to ensure the progesterone remains in solution. Thus, a 50 mg progesterone capsule based on 73 mg/g solubility would require a 685 mg capsule, and with the at least 10% addition, it would require approximately a 754 mg sized capsule. Based on each respective solubility listed below, the capsule sizes include (approximately): 579 mg, 1979 mg, 637 mg, 780 mg, and 958 mg respectively. These values, and their corresponding 10% additions are shown in Table 4.

TABLE 4

| Ingredient | Progesterone Solubility (mg/g) |
|---|---|
| CAPMUL MCM | 73.4 |
| CAPMUL PG8 | 95 |
| MIGLYOL 812 | 27.8 |
| CAPMUL MCM:GELUCIRE 44/14 (9:1) | 86.4 |
| CAPMUL MCM:GELUCIRE 44/14 (7:3) | 70.5 |
| CAPMUL MCM:GELUCIRE 44/14 (6:3) | 57.4 |

In addition, it has been found that the solubility of progesterone in a solvent of CAPMUL MCM in combination with GELUCIRE 44/14 in a 9:1 ratio increases the solubility to approximately 86 mg/g. Therefore, in various embodiments, progesterone or estradiol may be dissolved in a CAPMUL MCM and GELUCIRE 44/14 system, wherein the ratio of CAPMUL MCM to GELUCIRE 44/14 is 9:1.

TABLE 5

| Ingredient | Progesterone Solubility (mg/g) |
|---|---|
| CAPMUL MCM: GELUCIRE 44/14 (9:1) | 86.4 |
| CAPMUL MCM: GELUCIRE 44/14 (7:3) | 70.5 |
| CAPMUL MCM: GELUCIRE 44/14 (6:4) | 57.4 |

Example 4

In an exemplary embodiment, a capsule is provided containing a fill material having suspended progesterone comprising:

TABLE 6

| Ingredient | mg/Capsule | % | Function |
|---|---|---|---|
| Micronized Progesterone | 200.00 | 30.77 | Active |
| Medium Chain Triglyceride (MIGLYOL 812 or equivalent) | qs | qs | Solubilizing Agent |
| Lecithin Liquid | 1.63 | 0.25 | Lubricant/Emulsifier |
| Butylated Hydroxytoluene (also referred to as "BHT") | 0.13 | 0.02 | Antioxidant |

The above formulation is prepared as follows: MIGLYOL is heated to about 45° C. GELUCIRE 44/14 is added and mixed until dissolved. BHT is added and mixed until dissolved. Progesterone is suspended and passed through a colloid mill. The resultant fill mass can be used for encapsulation.

In an exemplary embodiment, a capsule is provided containing a fill material having partially solubilized progesterone comprising:

TABLE 7

| Ingredient | Qty/Capsule (mg) | % w/w | Qty/Capsule (mg) | Amount/Batch (kg) |
|---|---|---|---|---|
| Micronized Progesterone, USP | 200.00 | 33.33 | Active | 2.0 |
| Monoglycerides/diglycerides/triglycerides of caprylic/capricacid (CAPMUL MCM) | 394.0 | 65.67 | Solubilizing Agent | 3.94 |
| Lauroyl polyoxyl-32-glycerides (GELUCIRE 44/14 or equivalent) | 6.0 | 1 | Lubricant/Emulsifier | 0.06 |
| Total | 600.00 mg | 100 | | 6.0 kg |

For suspensions of progesterone and partially solubilized progesterone, GELUCIRE 44/14 may be added at 1% to 2% w/w to increase viscosity. The above formulation is prepared as follows: CAPMUL MCM is heated to about 65° C. GELUCIRE 44/14 is added and mixed until dissolved. Heat is removed. Progesterone is added and the mixture is passed through a colloid mill. The resultant fill mass can be used for encapsulation.

Example 5

In particular embodiments, a capsule is provided containing a pharmaceutical composition having fully solubilized, partially solubilized, or suspended progesterone comprising the components according to the formulations specified in Tables 8 and 9:

TABLE 8

| Ingredient | % | mg/Capsule | Function |
|---|---|---|---|
| Micronized Progesterone | 30.77 | 200.00 | Active |
| Medium Chain Triglyceride (MIGLYOL 812 or equivalent) | 65.93 | 428.55 | Carrier |
| Lauroyl polyoxyl-32-glycerides (GELUCIRE 44/14 or equivalent) | 3.00 | 19.50 | Suspending Agent |
| Butylated Hydroxytoluene | 0.03 | 1.95 | Antioxidant |
| Total | 100 | 650 | |

TABLE 9

| Ingredient | mg/Capsule | % | Function |
|---|---|---|---|
| Progesterone | 200.00 | 33.33 | Active |
| Medium Chain Triglyceride (MIGLYOL 812 or equivalent) | 389.60 | 64.93 | Solubilizing Agent |
| Lauroyl polyoxyl-32-glycerides (GELUCIRE 44/14 or equivalent) | 10.00 | 1.67 | Non-ionic Surfactant (suspending agent) |
| Butylated Hydroxytoluene | 0.40 | 0.07 | Antioxidant |
| Total | 600.00 | 100.0 | |

The pharmaceutical composition above can be prepared in accordance with the procedures noted in prior examples.

Example 6

A gel mass can be prepared in order to encapsulate the pharmaceutical compositions of the various Examples herein.

Gel mass compositions were formulated and produced according to the following steps. Purified water (22.2 kg) and glycerin (10.8 kg) were charged into a stainless steel tank with mixing and heated to a temperature of 80±5° C. Hydrolyzed gelatin (1.8 kg) and gelatin 200 bloom limed bone, NF (24.0 kg) were then added to the water/glycerin mixture and were mixed until all solids were completely dissolved. This resulted in the formation of a gel mass. The resulting gel mass was de-gassed under vacuum. Coloring agents OPATINT® white (0.6 kg) and OPATINT® red (0.6 kg) were then added to the gel mass and the resultant was mixed for about 5 minutes. The resultant was then de-gassed under vacuum for a sufficient period of time and ultimately passed to an encapsulation device for preparation of gel capsules of the types disclosed herein.

Example 7

Bioavailability Assessment—Fasted

A randomized single-dose oral bioequivalence study comparing 200 mg ultra-micronized progesterone capsule test product (T) and 200 mg PROMETRIUM® (progesterone) capsules (Abbott Laboratories, Abbott Park, IL) reference product (R) is conducted. Subjects are administered a single 200 mg dose of either test product (T) or the reference product (R) under fasting conditions, for example, subjects fasted at least 10.0 hours prior to dosing. Blood is collected pre-dose and post-dose. Pre-dose samples are collected at approximately −01.00, −00.50, and 00.00 hours. Post-dose samples are collected at approximately 01.00, 02.00, 03.00, 04.00, 05.00, 06.00, 07.00, 08.00, 09.00, 10.00, 12.00, 18.00, 24.00, 36.00 and 48.00 hours. Standard meals are provided at 04.00, 09.00, 13.00, 25.00, 29.00, 33.00 and 37.00 hours post-dose.

Pharmacokinetic measurements are assessed including Cmax, AUC and optionally Tmax. Comparative bioavailability of the test product (T) and reference product are assessed.

Example 8

Bioavailability Assessment—Fed

The procedures for determining bioavailability under fasted conditions are repeated except that subjects are administered a single 200 mg dose of either test product (T) or reference product (R) immediately following a high fat meal, for example, within 30 minutes of dosing. Blood is collected pre-dose and post-dose. Pre-dose samples are collected at approximately −01.00, −00.50, and 00.00 hours. Post-dose samples are collected at approximately 01.00, 02.00, 03.00, 04.00, 05.00, 06.00, 07.00, 08.00, 09.00, 10.00, 12.00, 18.00, 24.00, 36.00 and 48.00 hours. Standard meals are provided at 04.00, 09.00, 13.00, 25.00, 29.00, 33.00 and 37.00 hours post-dose. Pharmacokinetic measurements are assessed including $C_{max}$, AUC and optionally $T_{max}$. Bioavailability of the test product (T) in reference to the reference product is assessed. The effect of food on the comparative bioavailability of the test product (T) and the reference product (R) are also assessed.

Example 9

Method of manufacture in accordance with various embodiments are shown in FIGS. 1-3. With reference to FIG. 1, method of fill material, i.e. fill mass, preparation 100 is shown. Operation 102 comprises mixing a carrier, a lubricant, and an antioxidant as described herein. For example, lecithin and butylated hydroxytoluene may be mixed with one or more medium chain mono-, di- or triglycerides, or combinations thereof. Mixing may be facilitated by an impellor, agitator, or other suitable means. Operation 102 may be performed under an inert or relatively inert gas atmosphere, such as nitrogen gas N2. Mixing may be performed in any suitable vessel, such as a stainless steel vessel.

Operation 104 may comprise mixing ultra-micronized progesterone into the mixture of the carrier, the lubricant, and the antioxidant. A pasty substance is thus formed. Mixing may occur in a steel tank or vat. Mixing may be facilitated by an impellor, agitator, or other suitable means. Operation 104 may be performed under an inert or relatively inert gas atmosphere, such as nitrogen gas N2. Operation 106 comprises degasing. The resulting mixture from operation 106 may comprise a fill material suitable for production into a softgel capsule.

With reference to FIG. 2, softgel capsule, i.e. gel mass, production 200 is shown. Operation 202 comprises mixing glycerin with water. The water used in operation 202 may be purified by any suitable means, such as reverse osmosis, ozonation, filtration (e.g., through a carbon column) or the like. Mixing may be facilitated by an impellor, agitator, or other suitable means. Operation 202 may be performed under an inert or relatively inert gas atmosphere, such as nitrogen gas N2. Heating may be performed until the temperature reaches 80 □±5 □C.

Operation 204 comprises the addition of gelatin to the glycerin water mixture. Mixing may be facilitated by an impellor, agitator, or other suitable means. Operation 204 may be performed under an inert or relatively inert gas atmosphere, such as nitrogen gas $N_2$. A vacuum may be drawn in operation 204 to de-aerate.

Operation 206 comprises addition of a coloring agent such as a dye. A coloring agent may comprise products sold under the trademark OPATINT or other suitable agent. Operation 206 may be performed under an inert or relatively inert gas atmosphere, such as nitrogen gas $N_2$. Operation 208 comprises degasing. The resulting mixture from operation 208 may comprise a gel capsule material suitable for use as a gel capsule in production of a softgel capsule.

With reference to FIG. 3, softgel capsule assembly process 300 is shown. Operation 302 comprises heating the fill material. The fill material may be heated to any suitable temperature. In various embodiments, the fill material is heated to 30° C.+/−3° C. Fill material maybe heated in a fill hopper. A fill hopper may comprise a device configured to hold a volume of the fill material or to dispense the fill material in controlled volumes.

Operation 304 comprises filling a gel mass. A gel mass may be taken from the gel capsule material produced in operation 208 of FIG. 2. Filling may be performed by injecting, placing, or otherwise disposing the fill material within a volume defined by the gel capsule material. The filling may occur in an encapsulator. The spreader boxes may be a temperature of 55° C.+/−10° C. The wedge temperature may be 38° C.+/−3° C. The drum cooling temperature may be 4° C.+/−2° C. The encapsulator may be lubricated using MIGLYOL 812. Operation 304 thus produces one or more softgel capsules. Filling may comprise producing a ribbon of thickness 0.85±0.05 mm using spreader box knobs. The fill material may be injected into the gel to produce a fill weight having target weight ±5% (i.e., 650±33 mg and 325±16.3 mg).

Operation 306 comprises drying the softgel capsules. Drying may be performed in a tumble dryer, tray dryer, or combinations thereof. For example, drying may be performed in a tumble drying basket for between about 10 minutes and about 120 minutes. Drying may continue in a drying room for about 24 hours to about 72 hours. Polishing may be performed with isopropyl alcohol.

Example 10

Stability Study

In accordance with various embodiments, formulations in accordance with various embodiments have an exemplary shelf life of 3 months with storage at 25±2° C./60±5% RH in 75 cc HDPE white, opaque bottles with a 38/400 mm white child resistant cap.

Packaging during testing comprises a 75 cc round HDPE bottle and 33 mm cap. A Brasken FPT 300F resin is associated with the cap. Testing criteria include visual appearance, assay of progesterone, dissolution, content uniformity and microbial limits testing.

Three test groups are created. Test group 1 comprises a test at 40° C./75% RH. Test group 2 comprises a test at 30° C./65% RH. Test group 3 comprises a test at 25° C./60% RH. Test group 1 is tested for visual appearance, assay of ultra-micronized progesterone, and dissolution at months 1, 2, 3, and 6. Test group 2 is tested for visual appearance, assay of ultra-micronized progesterone, and dissolution at months 0, 1, 2, 3, 6, and 12. Test group 3 is tested for visual appearance, assay of ultra-micronized progesterone, and dissolution at months 0, 1, 2, 3, 6, 12 and 24.

Example 11

A particle size analysis is conducted by using a Beckman Coulter LS 13 320 Laser Diffraction Particle Size Analyzer (the "Beckman Device"). The Beckman Device uses laser diffraction to determine particle size. A sample of a formulation in accordance with various embodiments is provided. The Beckman Device particle sensor yields that the sample has an X50 of 6.67 µm, an X75 of 14.78 µm, and an X25 of 2.193 µm.

Example 12

A dissolution study was performed using a formulation in accordance with various embodiments. The results of the dissolution study are shown in FIG. 4.

The dissolution study was performed using a United States Pharmacopoeia dissolution apparatus 3 (reciprocating cylinder) ("USP Apparatus 3"). The USP Apparatus 3 was set to 30 dips per minute. Two hundred fifty mL (250 mL) of a solution of. 1N HCL with 3% sodium lauryl sulfate was used at 37° C.

Figure 4:
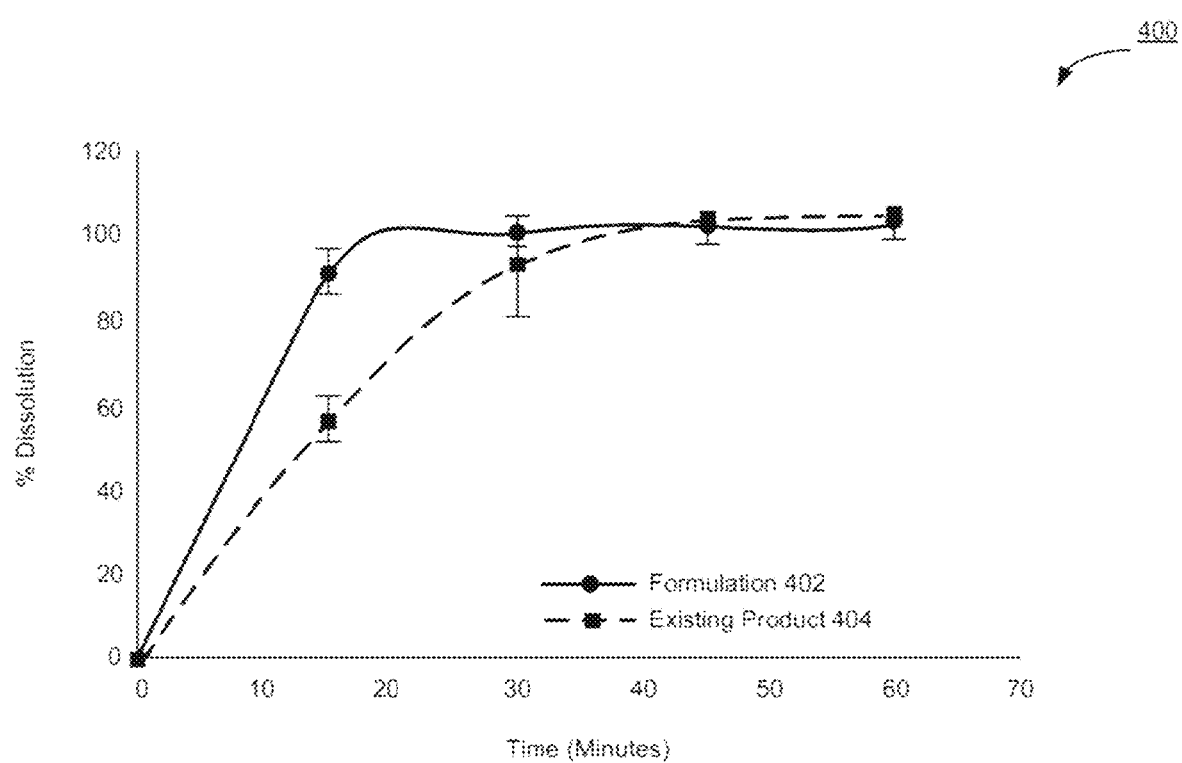
FIG. 4 illustrates a dissolution study of a formulation in accordance with various embodiments.

FIG. 4 shows dissolution percentage in the y axis over time in minutes on the x axis. A formulation in accordance with various embodiments is shown having circular dots, and is labeled formulation 402. An existing commercial pharmaceutical product containing progesterone is shown having square dots and is labeled existing product 404. As shown in FIG. 4, formulation 402 reaches a higher level of dissolution in a shorter time than existing product 404.

Example 13

For the purposes of this Example, a particle size analysis is conducted by using the Beckman Device. A sample API comprising ultra-micronized progesterone in accordance with various embodiments is provided for analysis.

Figure 5:
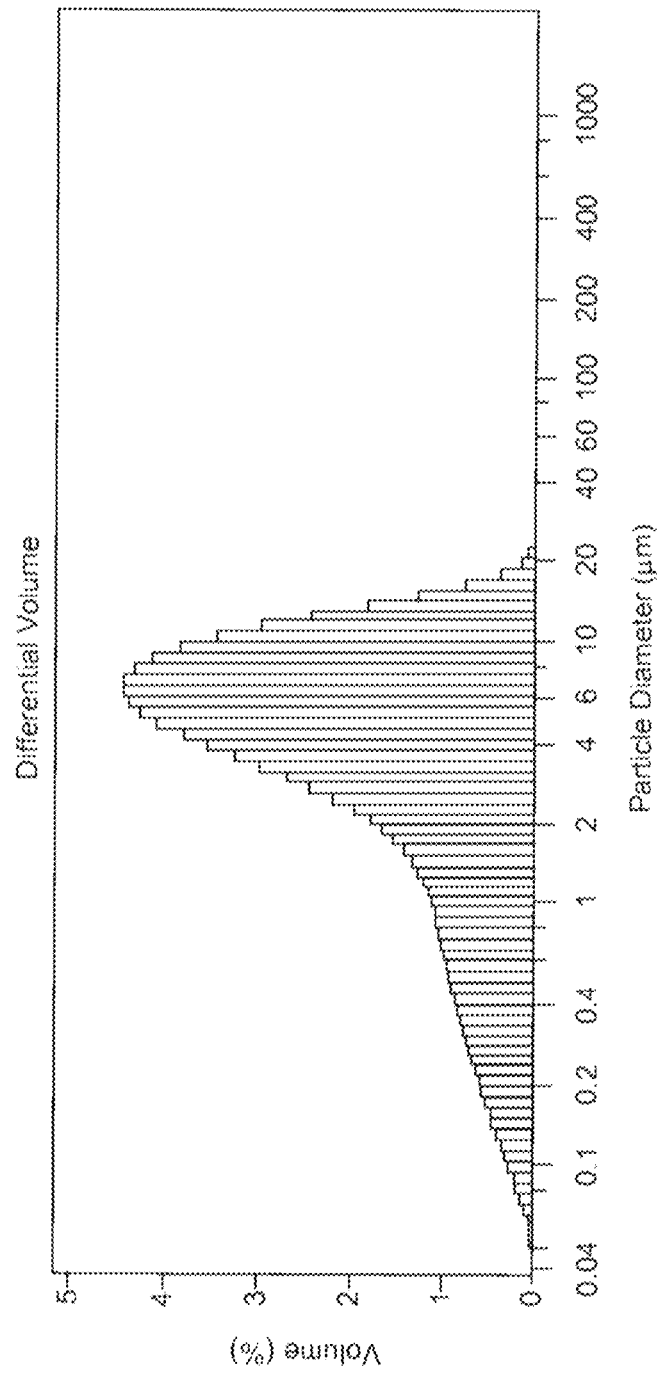
FIG. 5 illustrates a graph of the particle distribution obtained in Example 10.

Approximately 0.01 g of a sample API in accordance with various embodiments was combined with Coulter 1B and 10 mL of deionized water. Sonication was performed for 15 seconds. The Beckman Device, equipped with a ULM, performed analysis for 90 seconds. The Beckman Device was configured to use the Fraunhofer optical model. The Beckman Device yielded that the sample has an X50 of 4.279 µm, an X75 of 7.442 µm, and an X25 of 1.590 µm. The Beckman Device also yielded that the mean particle size is 4.975 µm, the median particle size is 4.279 µm, the mode particle size is 6.453 µm, and the standard deviation is 3.956 µm. A graph of the particle distribution obtained is shown in FIG. 5.

Example 14

Dissolution

Dissolution studies were performed using a formulation of this invention comparing the dissolution of progesterone to the dissolution of PROMETRIUM and comparing the dissolution of estradiol to the dissolution of Estrace. In one study, a formulation of the invention in capsules comprising 200 mg of progesterone and 2 mg estradiol was used. In a second study, a formulation of the invention in capsules comprising 50 mg of progesterone and 2 mg estradiol was used.

The dissolution study was performed using a USP dissolution apparatus (reciprocating cylinder) ("USP Apparatus 3"). The apparatus was set to 30 dips per minute. 250 mL of a solution of 0.1N HCl with 3% sodium lauryl sulfate was used at 37 C.

Figure 6:
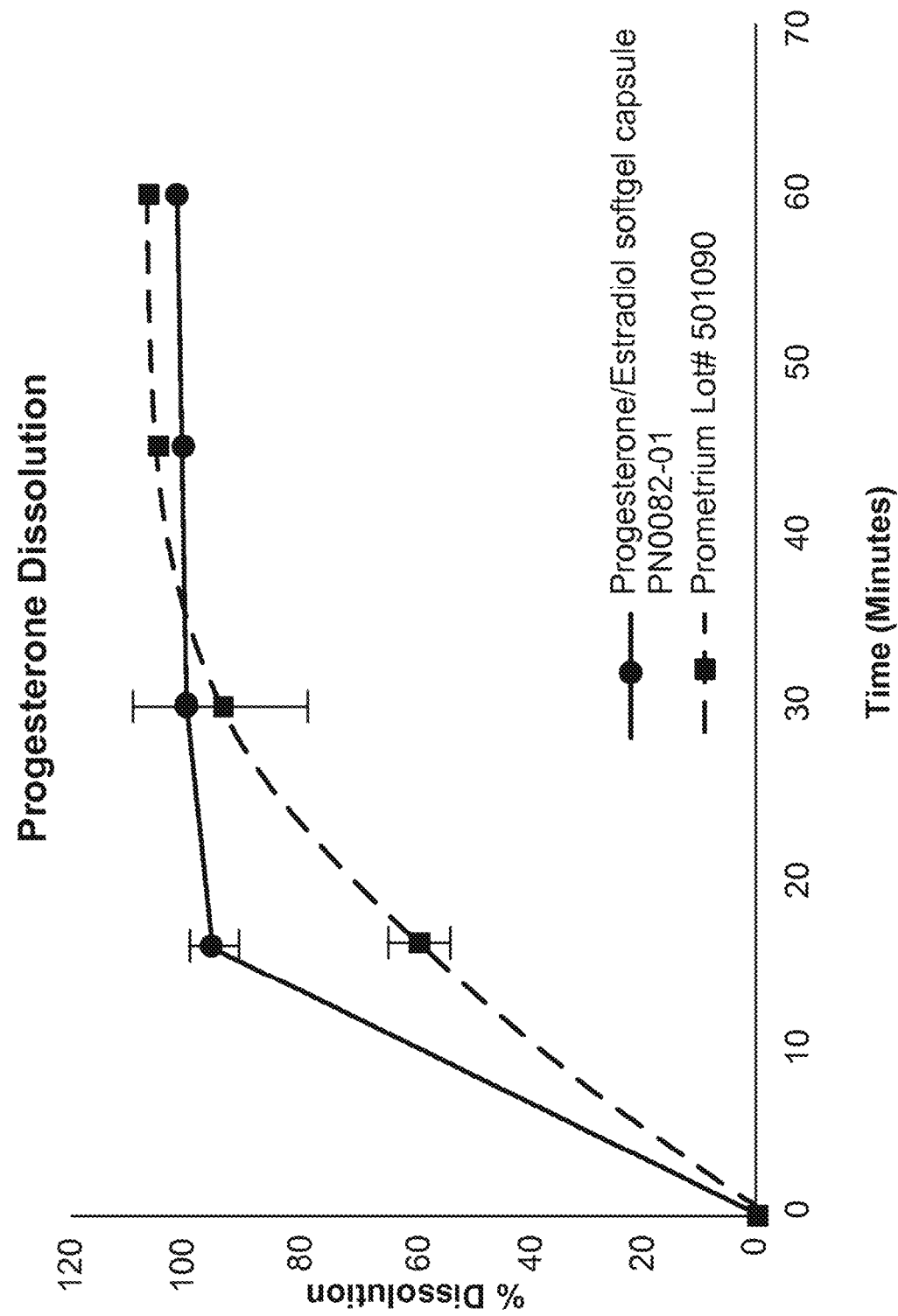
FIG. 6 illustrates a dissolution study of a formulation in accordance with various embodiments of the invention.

In both studies, progesterone was dissolved faster, and with smaller standard deviations, from the capsules of the invention than from PROMETRIUM. Dissolution of estradiol was comparable but marginally slower from the capsules of the invention than from Estrace. For illustrative purposes, a graph showing progesterone dissolution from the 200 mg progesterone capsule of the invention and from PROMETRIUM is attached as FIG. 6.

Both capsules of the invention were stable on storage in white HDPE bottles. Positive stability data were obtained with the 200 mg progesterone formulation over 6 months (>6 months data unavailable) and with the 50 mg progesterone formulation over 3 months (>3 months data unavailable).

Example 15

Bioavailability & Bioequivalence Assessment

This study was conducted to determine bioavailability and bioequivalence of reference product PROMETRIUM "R" (200 mg progesterone) and test product "T" as described in Table 9 herein. T was administered as a softgel capsule.

The study was an open-label, balanced, randomized, single-dose, two-treatment, three-period, three-sequence, crossover, partial replicate, reference-scaled oral bioequivalence study. A total of 72 healthy, adult, human, postmenopausal female subjects were enrolled in the study. Each subject was randomly assigned to a sequence (TRR, RTR, or RRT) such that each subject received T once and R twice during the course of the 32 day study (14 day washout between doses). R was administered twice so that the within subject variance could be calculated for later assessment of bioequivalence of the T and R formulations.

On study days 1, 15, and 29, patients who had been fasting for 10 hours were administered a high fat meal. 30 minutes after the meal, each patient was given a single softgel dose of T or, alternatively, R, in accordance with the patients' randomly assigned sequence. The dosage forms were taken with 240 ml of water. Subjects were housed in a clinical facility for at least 11 hours prior to dosing to at least 24 hours post dose.

A total of 20 (3×8 mL pre-dose and 17×6 mL post dose) blood samples were collected per subject after each dose. Pre-dose samples were collected at −1.00, −0.50, 0 hrs. Post dose samples were collected at 0.25, 0.50, 0.67, 0.83, 1.00, 1.33, 1.67, 2.00, 02.50, 3.00, 4.00, 6.00, 8.00, 12.00 24.00, 36.00 and 48.00 hours after dosing in vacutainers containing $K_2EDTA$. Based on an analysis of the collected blood samples, pharmacokinetic parameters including $C_{max}$, $AUC_{0-t}$, $AUC_{0-\infty}$, and $T_{max}$ were calculated using WinNonlin® version 5.3 (Pharsight Corporation). Although 72 patients were enrolled in the study, only data from the 62 patients who finished the study was used to calculate the values shown in Table 11, below.

TABLE 1

| Treatments (Dose Dosage form, route) +Product ID | | $C_{max}$ (ng/mL) Mean (% CV) | $T_{max}$ (hr) Median (Range) | $AUC_{0-t}$ (ng/mL)*hr Mean (% CV) | $AUC_{0-\infty}$ (ng/mL)*hr Mean (% CV) | $t_{1/2}$(hr) Median (Range) | $K_{el}$ (hrs)$^{-1}$ Mean (% CV) |
|---|---|---|---|---|---|---|---|
| Test product Progesterone Soft gel Capsule 200 mg, (Single dose) Oral | T | 102.5744 ± 139.2924 | 03.00 (0.83- 08.00) | 145.9243 ± 166.3317 | 169.2228 ± 172.1370 | 3.9681 ± 3.6762 | 0.2994 ± 0.1827 |
| Reference product PROMETRIUM ® (Progesterone) soft gel Capsule 200 mg | $R_1$ | 83.8777 ± 142.4315 | 4.00 (01.00- 12.00) | 139.8621 ± 195.2669 | 159.2795 ± 204.2120 | 3.4829 ± 3.0843 | 0.3209 ± 0.1906 |
| (Single dose- 2 × 200 mg), Oral | $R_2$ | 61.7121 ± 97.1097 | 4.00 (01.00- 12.00) | 98.6441 ± 130.9716 | 114.6482 ± 137.7684 | 3.4296 ± 2.9995 | 0.3485 ± 0.2491 |

Bioequivalence Analysis

In this study, the within-subject standard deviation of the reference formulation (SWR) was found to be ≥0.294 for $C_{max}$ and AUC ($AUC_{0-t}$ and $AUC_{0-\infty}$). As a result, the point estimate (test/reference geometric mean ratio) and 95% upper confidence bound for $(\mu_T-\mu_R)^2-(\theta S^2{}_{WR})$ was determined using ln-transformed data using SAS® statistical software version 9.2 from SAS Institute Inc, USA. This methodology (Scaled-Average Bioequivalence ("SABE")) is consistent with FDA guidelines for calculating bioequivalence for highly variable drugs, such as progesterone. Using the SABE methodology, T demonstrated improved bioavailability compared to PROMETRIUM and was considered superior to PROMETRIUM. Supporting data is shown in Tables 12 and 13 below.

TABLE 12

Point of estimate, Within-subject SD ($S_{wr}$) and 95% Upper Confidence Bound of Test product (T) versus Reference product (R) for, Progesterone (Baseline corrected)

| Parameter | Point Estimate (T/R ratio) | Within-Subject SD ($S_{wr}$) | Upper 95% Confidence Bound |
|---|---|---|---|
| $C_{max}$ (ng/mL) | 1.38 | 1.1334 | −0.481956 |
| $AUC_{0-t}$ (ng · hr/mL) | 1.28 | 0.8908 | −0.326613 |
| $AUC_{0-\infty}$ (ng · hr/mL) | 1.28 | 0.7704 | −0.135158 |

TABLE 13

Point of estimate, Within-subject SD (Swr) and 95% Upper Confidence Bound of Test product (T) versus Reference product (R) for, Progesterone (Baseline Uncorrected)

| Parameter | Point of estimate (T/R ratio) | Within-subject SD ($S_{wr}$) | 95% Upper Confidence Bound |
|---|---|---|---|
| $C_{max}$ (ng/mL) | 1.38 | 1.1333729 | −0.481836 |
| $AUC_{0-t}$ (ng · hr/mL) | 1.28 | 0.8907574 | −0.326277 |

TABLE 13-continued

Point of estimate, Within-subject SD (Swr) and 95% Upper Confidence Bound of Test product (T) versus Reference product (R) for, Progesterone (Baseline Uncorrected)

| Parameter | Point of estimate (T/R ratio) | Within-subject SD ($S_{wr}$) | 95% Upper Confidence Bound |
|---|---|---|---|
| $AUC_{0-\infty}$ (ng · hr/mL) | 1.29 | 0.7704431 | −0.134134 |

In view of the data noted above, the appropriate dosage of progesterone in the formulation disclosed herein necessary to achieve bioequivalence to PROMETRIUM was 150 mg. The computed results are shown in Table 14. This suggests that, in certain embodiments, the formulations disclosed herein have nearly 25% greater bioavailability than the current marketed formulation (PROMETRIUM).

TABLE 14

Summary of Evaluations of Baseline-Corrected Progesterone Results for a computed 150 mg Test Capsule vs. a 200 mg PROMETRIUM ® Capsule

| Parameter | Point Estimat | Within-Subject SD ($S_{wr}$) | Upper 95% Confidence |
|---|---|---|---|
| $C_{max}$ (ng/mL) | 1.03 | 1.1334 | −0.746836 |
| $AUC_{0-t}$ (ng · hr/mL) | 0.96 | 0.8908 | −0.465204 |

Example 16

Bioavailability Assessment—Fed #3

The amounts progesterone administered include 225 mg/day and 300 mg/day of progesterone. Progesterone capsule sizes are 75 mg and 150 mg capsules. Subjects taking the progesterone capsules are compared to subjects taking placebos. In both cases subjects are estrogen-primed.

The study includes: approximately a 6-week (42 days) screening period before enrolling into the study; approximately 6 weeks of Estrace®-priming before randomization; 6 weeks of blinded treatment (along with Estrace® treatment); and up to approximately 5 weeks of follow-up. The study is a phase 3, randomized, three-cycle, double-blind, placebo-controlled study to evaluate induction of secretory conversion of endometrium and withdrawal bleeding after administration of progesterone in estrogen-primed women with secondary amenorrhea. In clinical facilities, at the first visit (baseline—Cycle 1, day 1) subjects are estrogen-primed using an oral estradiol (i.e. 1.0 mg Estrace®). This priming takes place for 25 days. Compliance with estrogen-priming is determined (throughout, and at day 28 −3 day to +1 day). Subjects will begin cycle 2 of estrogen-priming (Cycle 2, day 1).

After 12 days (±2 days), subjects return to clinic. A transvaginal ultrasound (TVU) is conducted. Estrogen compliant subjects, and subjects meeting other criteria (i.e. double-walled endometrial thickness of ≥5 mm, ≥80% compliant with Estrace®, and negative urine pregnancy test) are randomized for treatment with progesterone.

Subjects begin blinded administration on day 14 of Cycle 2. Subjects continue both Estrace® and blinded administration through day 25 of Cycle 2. No medication is taken from Cycle 2, Day 26-28.

Estrace® 1.0 mg is re-started at Cycle 3, Day 1 and continued until Day 25. Subjects will return to the clinic at Cycle 2, Day 12 (±2d) for study assessments. At Cycle 3, Day 14, subjects will again begin taking blinded study medication through Day 25.

Subjects return to the clinic day 24 (±1 day) of Cycle 3, at which time an endometrial biopsy is conducted.

Subjects complete their final dose of Estrace® and blinded study medication on Day 25 and return to the clinic for a follow-up visit approximately 10 days later (upon receipt of biopsy results). Final visit assessments are conducted. Subjects whose endometrial biopsy results show proliferative endometrium are prescribed a 14 day course of medroxyprogesterone acetate 10 mg [MPA] as standard-of-care treatment to counterbalance the effect of estrogen-induced endometrial proliferation. These subjects receive a follow up telephone call at 2-4 weeks after completion of the MPA course and queried for the incidence of bleeding and adverse events. Unscheduled visits are allowed as needed.

Example 17

An open-label, balanced, randomized, two-treatment, two-period, two-sequence, single-dose, crossover, oral bioequivalence study was conducted with progesterone soft gel capsules having the formulation disclosed in Table 9 as fill material and PROMETRIUM® soft gel capsule 200 mg in normal healthy, adult human male subjects under fasting conditions.

A total of 25 normal healthy, adult, human male subjects were enrolled into the study. All subjects were housed in the clinical facility for at least 11 hours before dosing through a 24 hours post dose. After an overnight fast of at least 10 hours, a single dose of either test product (T) or reference product (R) (as per a randomization schedule) was administered orally to each subject with 240 mL of water. There was a washout period of 14 days between treatments. 18 blood samples were collected at: −1 hours, −0.5 hours, 0 hours, 0.25 hours, 0.5 hours, 0.67 hours, 0.83 hours, 1.00 hours, 1.33 hours, 1.67 hours, 2.00 hours, 2.50 hours, 3.00 hours, 4.00 hours, 6.00 hours, 8.00 hours, 12.00 hours, and 24.00 hours. The testing indicated that T and R had the following PK parameters:

TABLE 15

Summary of Primary Pharmacokinetic Profile of Test product (T), Progesterone soft gel Capsule 200 mg (Baseline Corrected)

| Pharmacokinetic Parameter | Geometric Mean* | Arithmetic Mean | Standard Deviation |
|---|---|---|---|
| $C_{max}$ (ng/mL) | 0.9701 | 1.1767 | 1.7458 |
| $AUC_{0-t}$ (ng · hr/mL) | 2.4130 | 4.5380 | 8.2350 |
| $AUC_{0-\infty}$ (ng · hr/mL) | 27.2091 | 36.9118 | 27.8580 |

*Estimate of Least Square Mean used to calculate Geometric Mean

TABLE 16

Summary of Primary Pharmacokinetic Profile of Reference product (R), PROMETRIUM ® (Progesterone) soft gel Capsule 200 mg (Baseline Corrected)

| Pharmacokinetic Parameter | Geometric Mean* | Arithmetic Mean | Standard Deviation |
|---|---|---|---|
| $C_{max}$ (ng/mL) | 2.0929 | 2.9877 | 3.1620 |
| $AUC_{0-t}$ (ng · hr/mL) | 4.9870 | 7.6108 | 7.0148 |
| $AUC_{0-\infty}$ (ng · hr/mL) | 13.1050 | 26.8905 | 55.3784 |

*Estimate of Least Square Mean used to calculate Geometric Mean

TABLE 17

T/R Ratio and 90% Confidence Intervals of Test product (T) versus Reference product (R) for, Progesterone (Baseline Corrected)

| Pharmacokinetic Parameter | T/R Ratio % | 90% Confidence Intervals |
|---|---|---|
| $C_{max}$ (ng/mL) | 46.35% | 34.3% to 62.63% |
| $AUC_{0-t}$ (ng · hr/mL) | 48.39% | 25.84% to 90.62% |
| $AUC_{0-\infty}$ (ng · hr/mL) | 207.62% | 72.18% to 597.25% |

This data indicates that T and R are not bioequivalent because the 90% confidence interval of the least square mean of $C_{max}$, $AUC_{0-t}$ and $AUC_{0-\infty}$ were 34.3% to 62.63%, 25.84% to 90.62%, and 72.18% to 597.25% respectively. They were thus not within the limit of 80.00% and 125.00% used by the FDA to demonstrate bioequivalence.

Example 18

An open-label, balanced, randomized, two-treatment, two-period, two-sequence, single-dose, crossover, oral bioequivalence study was conducted with progesterone soft gel capsules having the formulation disclosed in Table 9 as fill material and PROMETRIUM® soft gel capsule 200 mg in normal healthy, adult human male subjects under fed conditions.

A total of 25 normal healthy, adult, human male subjects were enrolled into the study. All subjects were housed in the clinical facility for at least 11 hours before dosing through a 24 hours post dose. After an overnight fast of at least 10 hours, a high fat, high calorie breakfast was served 30 minutes before administering a single dose of either test product (T) or reference product (R) (as per a randomization schedule). Capsules were given to each subject orally with 240 mL of water. There was a washout period of 14 days between treatments. 18 blood samples were collected at: −1 hours, −0.5 hours, 0 hours, 0.25 hours, 0.5 hours, 0.67 hours, 0.83 hours, 1.00 hours, 1.33 hours, 1.67 hours, 2.00 hours, 2.50 hours, 3.00 hours, 4.00 hours, 6.00 hours, 8.00 hours, 12.00 hours, and 24.00 hours. The testing indicated that T and R had the following PK parameters:

TABLE 18

Summary of Primary Pharmacokinetic Profile of Test product (T), Progesterone soft gel Capsule 200 mg (Baseline Corrected)

| Pharmacokinetic Parameter | Geometric Mean* | Arithmetic Mean | Standard Deviation |
|---|---|---|---|
| $C_{max}$ (ng/mL) | 20.8344 | 88.1233 | 165.6133 |
| $AUC_{0-t}$ (ng · hr/mL) | 42.6781 | 124.7467 | 215.4315 |
| $AUC_{0-\infty}$ (ng · hr/mL) | 59.0419 | 150.9140 | 237.6730 |

*Estimate of Least Square Mean used to calculate Geometric Mean

TABLE 19

Summary of Primary Pharmacokinetic Profile of Reference product (R), PROMETRIUM ® (Progesterone) soft gel Capsule 200 mg (Baseline Corrected)

| Pharmacokinetic Parameter | Geometric Mean* | Arithmetic Mean | Standard Deviation |
|---|---|---|---|
| $C_{max}$ (ng/mL) | 12.4661 | 41.5344 | 87.8350 |
| $AUC_{0-t}$ (ng · hr/mL) | 29.9365 | 60.0080 | 105.0084 |
| $AUC_{0-\infty}$ (ng · hr/mL) | 36.9906 | 65.4258 | 109.0883 |

*Estimate of Least Square Mean used to calculate Geometric Mean

TABLE 20

T/R Ratio and 90% Confidence Intervals of Test product (T) versus Reference product (R) for, Progesterone (Baseline Corrected)

| Pharmacokinetic Parameter | T/R Ratio % | 90% Confidence Intervals |
|---|---|---|
| $C_{max}$ (ng/mL) | 167.13% | 79.38% to 351.89% |
| $AUC_{0-t}$ (ng · hr/mL) | 142.56% | 85.01% to 239.08% |
| $AUC_{0-\infty}$ (ng · hr/mL) | 159.61% | 103.59% to 245.94% |

This data indicates that T and R are not bioequivalent because the 90% confidence interval of the least square mean of $C_{max}$, $AUC_{0-t}$ and $AUC_{0-\infty}$ were 79.38% to 351.89%, 85.01% to 239.08%, and 103.59% to 245.94%. They were thus not within the limit of 80.00% and 125.00% used by the FDA to demonstrate bioequivalence. But importantly, and unlike the fasted study, the fed study demonstrated that test product T demonstrated enhanced oral bioavailability vs. PROMETRIUM®.

It will be apparent to those skilled in the art that various modifications and variations can be made in this disclosure without departing from the spirit or scope of the disclosure. Thus, it is intended that this disclosure cover the modifications and variations of this disclosure provided they come within the scope of the appended claims and their equivalents.

Likewise, numerous characteristics and advantages have been set forth in the preceding description, including various alternatives together with details of the structure and function of the devices or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A pharmaceutical composition for orally administering progesterone to a subject in need thereof, the composition comprising:
   progesterone;
   a solubilizing agent; and
   a nonionic surfactant;
   wherein the solubilizing agent comprises predominantly $C_6$-$C_{12}$ fatty acid tri-esters of glycerol;
   wherein the progesterone is present from about 20 to about 50 weight percent of the composition; and
   wherein the nonionic surfactant is lauroyl polyoxyl-32 glycerides.

2. The pharmaceutical composition of claim 1, wherein the solubilizing agent further comprises a $C_6$-$C_{12}$ fatty acid mono-ester of glycerol.

3. The pharmaceutical composition of claim 2, wherein the solubilizing agent further comprises a $C_6$-$C_{12}$ fatty acid di-ester of glycerol.

4. The pharmaceutical composition of claim 1, wherein the tri-ester of glycerol comprises predominantly esters of caprylic fatty acid ($C_8$) and capric fatty acid ($C_{10}$).

5. The pharmaceutical composition of claim 1, wherein the amount of progesterone is from 25 mg to 200 mg.

6. The pharmaceutical composition of claim 1, wherein the amount of progesterone is 75 mg or 150 mg.

7. The pharmaceutical composition of claim 1, wherein the progesterone includes solubilized progesterone and suspended progesterone.

8. The pharmaceutical composition of claim 1, wherein the composition is provided in a gelatin capsule.

9. The pharmaceutical composition of claim 1, wherein the composition has a total mass of less than 500 mg.

10. The pharmaceutical composition of claim 1, wherein the amount of progesterone comprises about 33% by weight of the composition; the solubilizing agent comprises about 65% by weight of the composition, and the non-ionic surfactant comprises about 1.7% by weight of the composition.

11. The pharmaceutical composition of claim 1, wherein the amount of progesterone comprises about 33.33% by weight of the composition; the solubilizing agent comprises about 64.93% by weight of the composition, and the non-ionic surfactant comprises about 1.67% by weight of the composition.

12. The pharmaceutical composition of claim 10, further comprising an antioxidant.

13. The pharmaceutical composition of claim 12, wherein the antioxidant is butylated hydroxy toluene.

14. The pharmaceutical composition of claim 13, wherein the solubilizing agent is medium chain triglycerides of caprylic fatty acid (C8) and capric fatty acid (C10).

* * * * *